(12) United States Patent
Marasco

(10) Patent No.: US 12,024,567 B2
(45) Date of Patent: Jul. 2, 2024

(54) METHOD OF TREATING A TUMOR EXPRESSING CARBONIC ANHYDRASE IX (G250) BY ADMINISTERING A G250-SPECIFIC CHIMERIC ANTIGEN RECEPTOR

(71) Applicant: Dana-Farber Cancer Institute, Inc., Boston, MA (US)

(72) Inventor: Wayne A. Marasco, Wellesley, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 334 days.

(21) Appl. No.: 17/129,369

(22) Filed: Dec. 21, 2020

(65) Prior Publication Data

US 2021/0221906 A1   Jul. 22, 2021

Related U.S. Application Data

(62) Division of application No. 15/537,780, filed as application No. PCT/US2015/067178 on Dec. 21, 2015, now Pat. No. 10,870,705.

(60) Provisional application No. 62/094,596, filed on Dec. 19, 2014.

(51) Int. Cl.
| | |
|---|---|
| C07K 16/30 | (2006.01) |
| A61K 35/17 | (2015.01) |
| A61K 38/20 | (2006.01) |
| A61K 39/00 | (2006.01) |
| C07K 14/705 | (2006.01) |
| C07K 14/725 | (2006.01) |
| C07K 16/40 | (2006.01) |
| C12N 5/0783 | (2010.01) |
| C12N 9/88 | (2006.01) |

(52) U.S. Cl.
CPC .............. *C07K 16/30* (2013.01); *A61K 35/17* (2013.01); *A61K 38/2013* (2013.01); *A61K 39/0011* (2013.01); *C07K 14/7051* (2013.01); *C07K 14/70521* (2013.01); *C07K 16/40* (2013.01); *C12N 5/0637* (2013.01); *C12N 5/0638* (2013.01); *C12N 9/88* (2013.01); *C12Y 402/01001* (2013.01); *A61K 2039/505* (2013.01); *C07K 2317/51* (2013.01); *C07K 2317/515* (2013.01); *C07K 2317/565* (2013.01); *C07K 2317/60* (2013.01); *C07K 2317/622* (2013.01); *C07K 2319/03* (2013.01); *C07K 2319/33* (2013.01); *C07K 2319/74* (2013.01); *C12N 2510/00* (2013.01)

(58) Field of Classification Search
CPC .... C07K 16/30; C07K 16/40; C07K 2317/51; C07K 2317/515; C07K 2317/565; C07K 2317/622; C07K 2319/03; A61K 39/0011; A61K 2039/505
See application file for complete search history.

(56) References Cited

U.S. PATENT DOCUMENTS

| | | | |
|---|---|---|---|
| 4,683,202 | A | 7/1987 | Mullis |
| 4,797,368 | A | 1/1989 | Carter et al. |
| 5,139,941 | A | 8/1992 | Muzyczka et al. |
| 5,928,906 | A | 7/1999 | Koester et al. |
| 5,994,136 | A | 11/1999 | Naldini et al. |
| 6,013,516 | A | 1/2000 | Verma et al. |
| 8,466,263 | B2 | 6/2013 | Marasco et al. |

FOREIGN PATENT DOCUMENTS

| | | |
|---|---|---|
| WO | 065027 | 6/2007 |
| WO | 100615 | 6/2014 |
| WO | 165707 | 10/2014 |
| WO | 100980 | 6/2016 |

OTHER PUBLICATIONS

Sadelain M, et al. (Apr. 2013) Cancer Discov. 3(4): 388-398. (doi:10.1158/2159-8290.CD-12-0548).*
Irving BA and Weiss A. (Mar. 8, 1991) Cell. 64:891-901.*
Shirasu N and Kuroki M (2012) Anticancer Research 32: 2377-2384.*
**Lo et al., "Regression of established renal cell carcinoma in nude mice using lentivirus-transduced human T cells expressing a human anti-CAIX chimeric antigen receptor", Oncolytics, (2014), pp. 1-12.
**Lo, Agnes SY, et al. "Anti-GD3 chimeric sFv-CD28/T-cell receptor .zeta. designer T cells for treatment of metastatic melanoma and other neuroectodermal tumors." Clinical Cancer Research 16.10 (2010): 2769-2780.
Lokich J., "Spontaneous regression of metastatic renal cancer. Case report and literature review", Am J Clin Oncol, (1997), vol. 20, No. 4, pp. 416-418.
**Loncaster, Juliette A., et al. "Carbonic anhydrase (CA IX) expression, a potential new intrinsic marker of hypoxia correlations with tumor oxygen measurements and prognosis in locally advanced carcinoma of the cervix." Cancer research61.17 (2001): 6394-6399.
**Loskog, Angelica, et al. "Addition of the CD28 signaling domain to chimeric T-cell receptors enhances chimeric T-cell resistance to T regulatory cells." Leukemia 20.10 (2006): 1819.
**Maher, John, et al. "Human T-lymphocyte cytotoxicity and proliferation directed by a single chimeric TCR.zeta./CD28 receptor." Nature biotechnology 20.1 (2002): 70.
**Mansour, Suzanne L., Kirk R. Thomas, and Mario R. Capecchi. "Disruption of the proto-oncogene int-2 in mouse embryo-derived stem cells: a general strategy for targeting mutations to non-selectable genes." Nature 336.6197 (1988): 348.
**McLaughlin et al. Adeno-associated virus general transduction vectors: analysis of proviral structures. J Virol. 1988; 62:1963-73.
**Miller et al. Gene Transfer by Retrovirus Vectors Occurs Only in Cells That Are Actively Replicating at the Time of Infection. Molecular and Cellular Biology. 1990; 10(8): 4239-4242.

(Continued)

*Primary Examiner* — Robert S Landsman
(74) *Attorney, Agent, or Firm* — Baker, Donelson, Bearman, Caldwell & Berkowitz, P.C.

(57) ABSTRACT

The present invention provides chimeric antigen receptor cells specific for carbonic anhydrase IX (CAIX) and methods of using same for treatment of CAIX expressing cancers such as renal cell carcinoma.

14 Claims, 18 Drawing Sheets

Specification includes a Sequence Listing.

(56) References Cited

OTHER PUBLICATIONS

**Milone, Michael C., et al. "Chimeric receptors containing CD137 signal transduction domains mediate enhanced survival of T cells and increased antileukemic efficacy in vivo." Molecular Therapy 17.8 (2009): 1453-1464.
**Miotti, Silvia, et al. "Level of anti-mouse-antibody response induced by bi-specific monoclonal antibody OC/TR in ovarian-carcinoma patients is associated with longer survival." International journal of cancer 84.1 (1999): 62-68.
**Mirzabekov, Tajib, et al. "Paramagnetic proteoliposomes containing a pure, native, and oriented seven-transmembrane segment protein, CCR5." Nature biotechnology 18.6 (2000): 649.
**Mor, Felix, and Irun R. Cohen. "IL-2 rescues antigen-specific T cells from radiation or dexamethasone-induced apoptosis. Correlation with induction of Bcl-2." The Journal of Immunology 156.2 (1996): 515-522.
**Murugaiyan, Gopal, and Bhaskar Saha. "Protumor vs antitumor functions of IL-17." The Journal Immunology183.7 (2009): 4169-4175.
Oosterwijk E; Ruiter DJ; Hoedemaker PJ; Pauwels EK; Jonas U; Zwartendijk J et al., "Monoclonal antibody G 250 recognizes a determinant present in renal-cell carcinoma and absent from normal kidney", International Journal of Cancer, (1986), vol. 38, No. 4, pp. 489-494.
Pastorekova S. Carbonic anhydrase IX (CA IX) as a potential target for cancer therapy. Cancer Therapy 2004; 2: 245-262.
**Pastorekova, S. I. L. V. I. A., et al. "Carbonic anhydrase IX, MN/CA IX: analysis of stomach complementary DNA sequence and expression in human and rat alimentary tracts." Gastroenterology 112.2 (1997): 398-408.
**Pegram, Hollie J., Jae H. Park, and Ranier J. Brentjens. "CD28z cars and armored cars." Cancer journal (Sudbury, Mass.) 20.2 (2014): 127.
**Saamio, Juha, et al. "Immunohistochemistry of carbonic anhydrase isozyme IX (MN/CA IX) in human gut reveals polarized expression in the epithelial cells with the highest proliferative capacity." Journal of Histochemistry Cytochemistry 46.4 (1998): 497-504.
**Sadelain, Michel, Renier Brentjens, and Isabelle Riviere. "The promise and potential pitfalls of chimeric antigen receptors." Current opinion in immunology 21.2 (2009): 215-223.
**Savoldo et al., "CD2 costimulation improves expansion and persistence of chimeric antigen receptor-modified T cells in lymphoma patients", The Journal of Clinical Investigation, vol. 121, No. 5, May 2011. 1822-1826.
**Schaft, Niels, et al. "Peptide fine specificity of anti-glycoprotein 100 CTL is preserved following transfer of engineered TCR.alpha..beta. genes into primary human T lymphocytes." The Journal of Immunology 170.4 (2003): 2186-2194.
**Schwarzer, Adrian, et al. "Regulatory T-cells and associated pathways in metastatic renal cell carcinoma (mRCC) patients undergoing DC-vaccination and cytokine-therapy." PLOS One7.10 (2012): e46600.
**Song, De-Gang, et al. "In vivo persistence, tumor localization, and antitumor activity of CAR-engineered T cells is enhanced by costimulatory signaling through CD137 (4-1BB)." Cancer research 71.13 (2011): 4617-4627.
**Sui, Jianhua, et al. "Broadening of neutralization activity to directly block a dominant antibody-driven SARS-coronavirus evolution pathway." PLOS pathogens 4.11 (2008): e1000197.
**Thomas, Kirk R., and Mario R. Capecchi. "Site-directed mutagenesis by gene targeting in mouse embryo-derived stem cells." Cell 51.3 (1987): 503-512.
**Tratschin, J. D., Irving L. Miller, and Barrie J. Carter. "Genetic analysis of adeno-associated virus: properties of deletion mutants constructed in vitro and evidence for an adeno-associated virus replication function." Journal of virology 51.3 (1984): 611-619.

**Varghese, Frency, et al. "IHC Profiler: an open source plugin for the quantitative evaluation and automated scoring of immunohistochemistry images of human tissue samples." PloS one 9.5 (2014): e96801.
**Wald, Ori, et al. "IFN-.gamma. acts on T cells to induce NK cell mobilization and accumulation in target organs." The Journal of Immunology 176.8 (2006): 4716-4729.
**Wilkie, Scott, et al. "Retargeting of human T cells to tumor-associated MUC1: the evolution of a chimeric antigen receptor." The Journal of Immunology 180.7 (2008): 4901-4909.
Written Opinion of the International Searching Authority for PCT/US2015/067178, dated Apr. 11, 2016.
**Xu et al., "Unique Biological Properties of Catalytic Domain Directed Human Anti-CAIX Antibodies Discovered through Phage-Display Technology" Plos One, Mar. 2010, vol. 5, Issue 3, pp. 1-13.
**Zavada, J., et al. "Soluble form of carbonic anhydrase IX (CA IX) in the serum and urine of renal carcinoma patients." British journal of cancer 89.6 (2003): 1067.
**Zeytin, Hasan, et al. "Targeted Delivery of Murine IFN- gamma. Using a Recombinant Fowlpox Virus: NK Cell Recruitment to Regional Lymph Nodes and Priming of Tumor-Specific Host Immunity." Journal of Interferon & Cytokine Research 28.2 (2008): 73-87.
** Atkins, Michael, et al. "Carbonic anhydrase IX expression predicts outcome of interleukin 2 therapy for renal cancer." Clinical cancer research 11.10 (2005): 3714-3721.
Bailey A; McDermott DF., "Immune checkpoint inhibitors as novel targets for renal cell carcinoma therapeutics", Cancer J, (2013), vol. 19, No. 4, pp. 348-352.
**Bar, Eva, et al. "IL-17 regulates systemic fungal immunity by controlling the functional competence of NK cells." Immunity40.1 (2014): 117-127.
Bedke J; Stenzl A., "Immunotherapeutic strategies for the treatment of renal cell carcinoma: where are we now?", Expert Review of Anticancer Therapy, (2013), vol. 13, No. 12, pp. 1399-1408.
**Blomer, Ulrike, et al. "Highly efficient and sustained gene transfer in adult neurons with a lentivirus vector." Journal of virology 71.9 (1997): 6641-6649.
**Bridgeman et al., "The second cellular therapy of cancer symposium" Cancer Immunol Immunother (2010) 59:971-974.
Bubenik J., "Mhc class I down-regulation: tumour escape from immune surveillance? (review)", International Journal of Oncology, (2004), vol. 25, No. 2, pp. 487-491.
**Carpenito, Carmine, et al. "Control of large, established tumor xenografts with genetically retargeted human T cells containing CD28 and CD137 domains." Proceedings of the National Academy of Sciences 106.9 (2009): 3360-3365.
Chang AE; Li Q; Jiang G; Sayre DM; Braun TM; Redman BG., "Phase II trial of autologous tumor vaccination, anti-CD3-activated vaccine-primed lymphocytes, and interleukin-2 in stage IV renal cell cancer", J Clin Oncol, (2003), vol. 21, No. 5, pp. 884-890.
**Cotten, Matt, et al. "High-efficiency receptor-mediated delivery of small and large (48 kilobase gene constructs using the endosome-disruption activity of defective or chemically inactivated adenovirus particles." Proceedings of the National Academy of Sciences 89.13 (1992): 6094-6098.
** Dudley M E, Wunderlich J R, Robbins P F, Yang J C, Hwu P, Schwartzentruber D J et al. Cancer regression and autoimmunity in patients after clonal repopulation with antitumor lymphocytes. Science 2002; 298(5594): 850-4.
** Frigola, Xavier, et al. "Identification of a soluble form of B7-H1 that retains immunosuppressive activity and is associated with aggressive renal cell carcinoma." Clinical Cancer Research17.7 (2011): 1915-1923.
Gajewski TF; Meng Y; Blank C; Brown I; Kacha A; Kline J et al., "Immune resistance orchestrated by the tumor microenvironment", Immunological Reviews, (2006), vol. 213, pp. 131-145.
**GenBank accession No. GQ903548; referenced in Xu, Chen, et al. "Unique biological properties of catalytic domain directed human anti-CAIX antibodies discovered through phage-display technology." PloS one 5.3 (2010): e9625.
**GenBank accession No. GQ903549; referenced in Xu, Chen, et al. "Unique biological properties of catalytic domain directed human

(56) References Cited

OTHER PUBLICATIONS anti-CAIX antibodies discovered through phage-display technology." PloS one 5.3 (2010): e9625.
**GenBank accession No. GQ903550; referenced in Xu, Chen, et al. "Unique biological properties of catalytic domain directed human anti-CAIX antibodies discovered through phage-display technology." PloS one 5.3 (2010): e9625.
**GenBank accession No. GQ903551; referenced in Xu, Chen, et al. "Unique biological properties of catalytic domain directed human anti-CAIX antibodies discovered through phage-display technology." PloS one 5.3 (2010): e9625.
**GenBank accession No. GQ903552; referenced in Xu, Chen, et al. "Unique biological properties of catalytic domain directed human anti-CAIX antibodies discovered through phage-display technology." PloS one 5.3 (2010): e9625.
**GenBank accession No. GQ903553; referenced in Xu, Chen, et al. "Unique biological properties of catalytic domain directed human anti-CAIX antibodies discovered through phage-display technology." PloS one 5.3 (2010): e9625.
**GenBank accession No. GQ903554; referenced in Xu, Chen, et al. "Unique biological properties of catalytic domain directed human anti-CAIX antibodies discovered through phage-display technology." PloS one 5.3 (2010): e9625.
**GenBank accession No. GQ903555; referenced in Xu, Chen, et al. "Unique biological properties of catalytic domain directed human anti-CAIX antibodies discovered through phage-display technology." PloS one 5.3 (2010): e9625.
**GenBank accession No. GQ903556; referenced in Xu, Chen, et al. "Unique biological properties of catalytic domain directed human anti-CAIX antibodies discovered through phage-display technology." PloS one 5.3 (2010): e9625.
**GenBank accession No. GQ903557; referenced in Xu, Chen, et al. "Unique biological properties of catalytic domain directed human anti-CAIX antibodies discovered through phage-display technology." PloS one 5.3 (2010): e9625.
**GenBank accession No. GQ903558; referenced in Xu, Chen, et al. "Unique biological properties of catalytic domain directed human anti-CAIX antibodies discovered through phage-display technology." PloS one 5.3 (2010): e9625.
**GenBank accession No. GQ903559; referenced in Xu, Chen, et al. "Unique biological properties of catalytic domain directed human anti-CAIX antibodies discovered through phage-display technology." PloS one 5.3 (2010): e9625.
**GenBank accession No. GQ903560; referenced in Xu, Chen, et al. "Unique biological properties of catalytic domain directed human anti-CAIX antibodies discovered through phage-display technology." PloS one 5.3 (2010): e9625.
**GenBank accession No. GQ903561; referenced in Xu, Chen, et al. "Unique biological properties of catalytic domain directed human anti-CAIX antibodies discovered through phage-display technology." PloS one 5.3 (2010): e9625.
**Gill, Saar, et al. "Efficacy against human acute myeloid leukemia and myeloablation of normal hematopoiesis in a mouse model using chimeric antigen receptor-modified T cells." Blood (2014): blood-2013.
**Grepin, Renaud, et al. "The CXCL7/CXCR1/2 axis is a key driver in the growth of clear cell renal cell carcinoma." Cancer research 74.3 (2014): 873-883.
**Hilvo, Mika, et al. "Biochemical characterization of Ca Ix, one of the most active carbonic anhydrase isozymes." Journal of Biological Chemistry 283.41 (2008): 27799-27809.
**Hinrichs, Christian S., et al. "Type 17 CD8+ T cells display enhanced antitumor immunity." Blood 114.3 (2009): 596-599.

**Hombach, A., et al. "A chimeric receptor that selectively targets membrane-bound carcinoembryonic antigen (mCEA) In the presence of soluble CEA." Gene therapy 6.2 (1999): 300.
**Hombach, Andreas A., et al. "OX40 costimulation by a chimeric antigen receptor abrogates CD28 and IL-2 induced L-10 secretion by redirected CD4+ T cells." Oncoimmunology1.4 (2012): 458-466.
**Hombach, Andreas A., Gunter Rappl, and Hinrich Abken. "Arming cytokine-induced killer cells with chimeric antigen receptors: CD28 outperforms combined CO28-OX40 "super-stimulation"." Molecular Therapy 21.12 (2013): 2268-2277.
**Horwich et al. Synthesis of Hepadnavirus Particles That Contain Replication—Defective Duck Hepatitis B Virus Genomes in Cultured HuH7 Cells. J Virol. 1990; 64(2): 642-50.
**Inouye et al. Up-promoter mutations in the Ipp gene of *Escherichia coli*. Nucleic Acids Res. 1985; 13(9): 3101-3110.
International Search Report for PCT/US2015/067178, dated Apr. 11, 2016.
**Isakov, Noah, and Amnon Altman. "PKC-theta-mediated signal delivery from the TCR/CD28 surface receptors." Frontiers in immunology 3 (2012): 273.
**Ivanov, Sergey, et al. "Expression of hypoxia-inducible cell-surface transmembrane carbonic anhydrases in human cancer." The American journal of pathology 158.3 (2001): 905-919.
Joyner, Alexandra L., William C. Skarnes, and Janet Rossant. "Production of a mutation in mouse En-2 gene by homologous recombination in embryonic stem cells." Nature 338.6211 (1989): 153-156.
**Kalos, Michael, et al. "T cells with chimeric antigen receptors have potent antitumor effects and can establish memory in patients with advanced leukemia." Science translational medicine 3.95 (2011): 95ra73-95ra73.
**Kershaw, Michael H., et al. "A phase I study on adoptive immunotherapy using gene-modified T cells for ovarian cancer." Clinical Cancer Research 12.20 (2006): 6106-6115.
**Lamers et al., "Process validation and clinical evaluation of a protocol to generate gene-modified T lymphocytes for imunogene therapy for metastatic renal cell carcinoma: GMP-controlled transduction and expansion of patient's T lymphocytes using a carboxy anhydrase IX-specific scFv transgene" Cytotherapy (2006) vol. 8, Nn. 6, 542-553.
**Lamers, Cor HJ, et al. "Immune responses to transgene and retroviral vector in patients treated with ex vivo-engineered T cells." Blood 117.1 (2011): 72-82.
**Lamers, Cor HJ, et al. "Long-term stability of T-cell activation and transduction components critical to the processing of clinical batches of gene-engineered T cells." Cytotherapy 15.5 (2013): 620-626.
**Lamers, Cor HJ, et al. "Treatment of metastatic renal cell carcinoma with CAIX CAR-engineered T cells: clinical evaluation and management of on-target toxicity." Molecular therapy 21.4 (2013): 904-912.
**Laughlin et al. Latent infection of KB cells with adeno-associated virus type 2. J Virol. 1986; 8(10): 515-524.
**Lebkowski, Jane S., et al. "Adeno-associated virus: a vector system for efficient introduction and integration of DNA into a variety of mammalian cell types." Molecular and cellular biology 8.10 (1988): 3988-3996.
**Liao, Shu Y., et al. "Identification of the MN antigen as a diagnostic biomarker of cervical intraepithelial squamous and glandular neoplasia and cervical carcinomas." The American journal of pathology 145.3 (1994): 598.
**Liao, Shu-Yuan, et al. "Identification of the MN/CA9 protein as a reliable diagnostic biomarker of clear cell carcinoma of the kidney." Cancer research 57.14 (1997): 2827-2831.

* cited by examiner

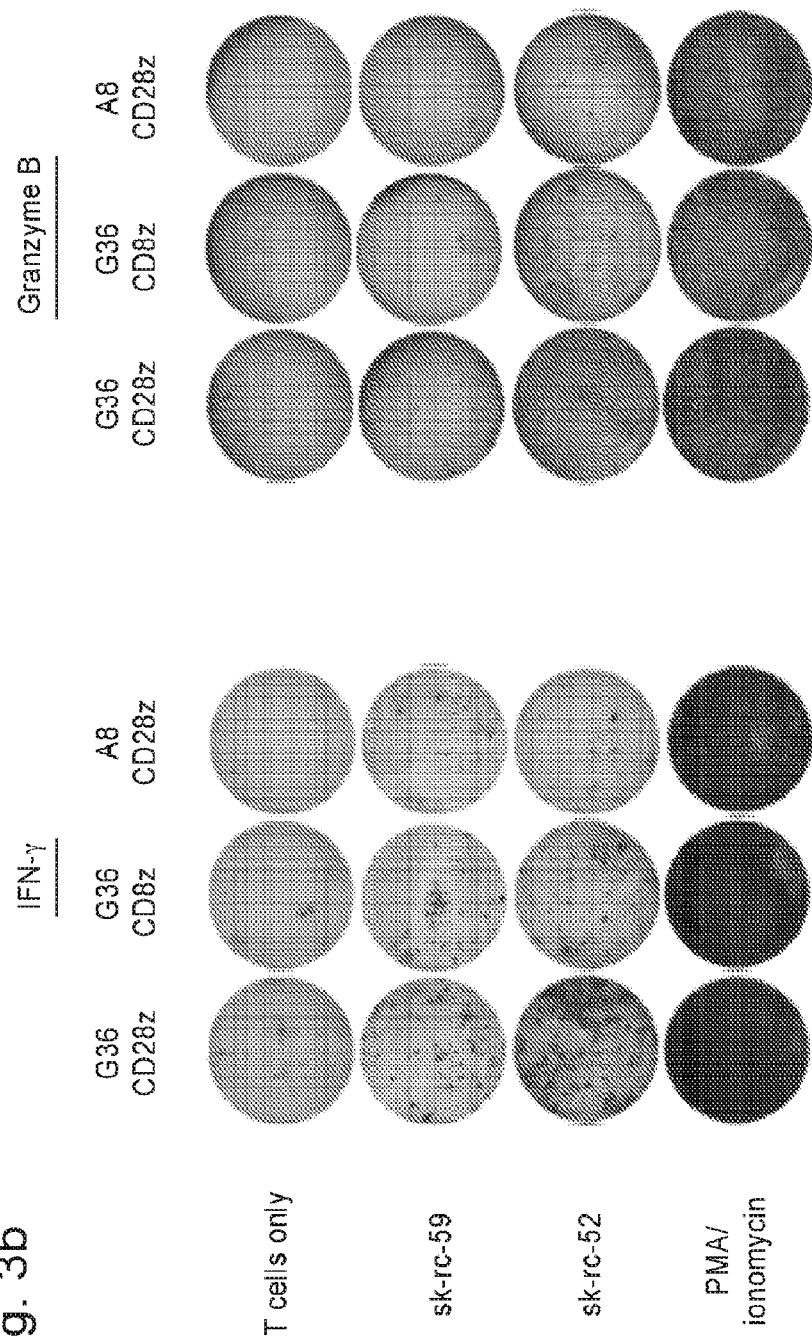

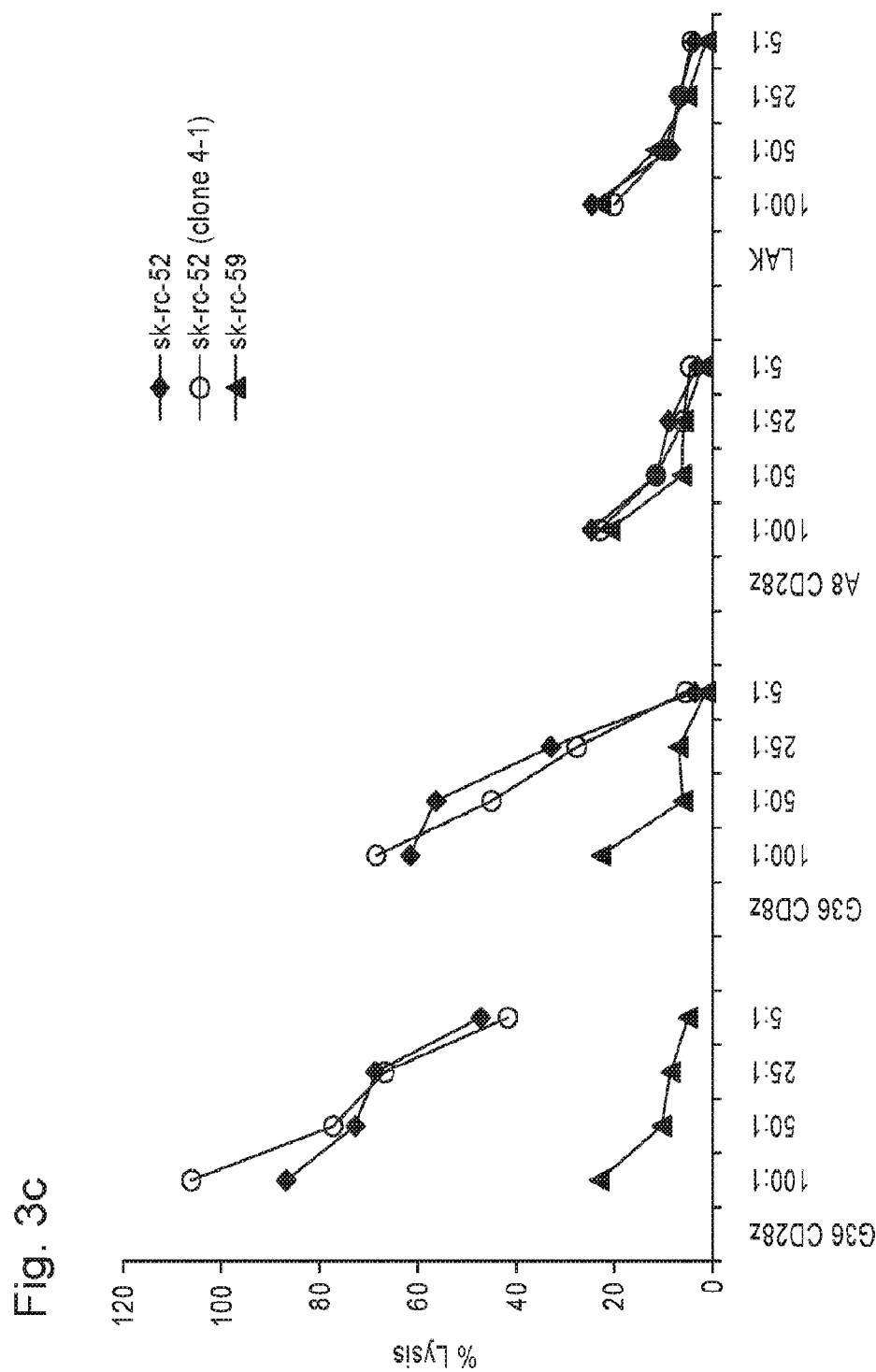

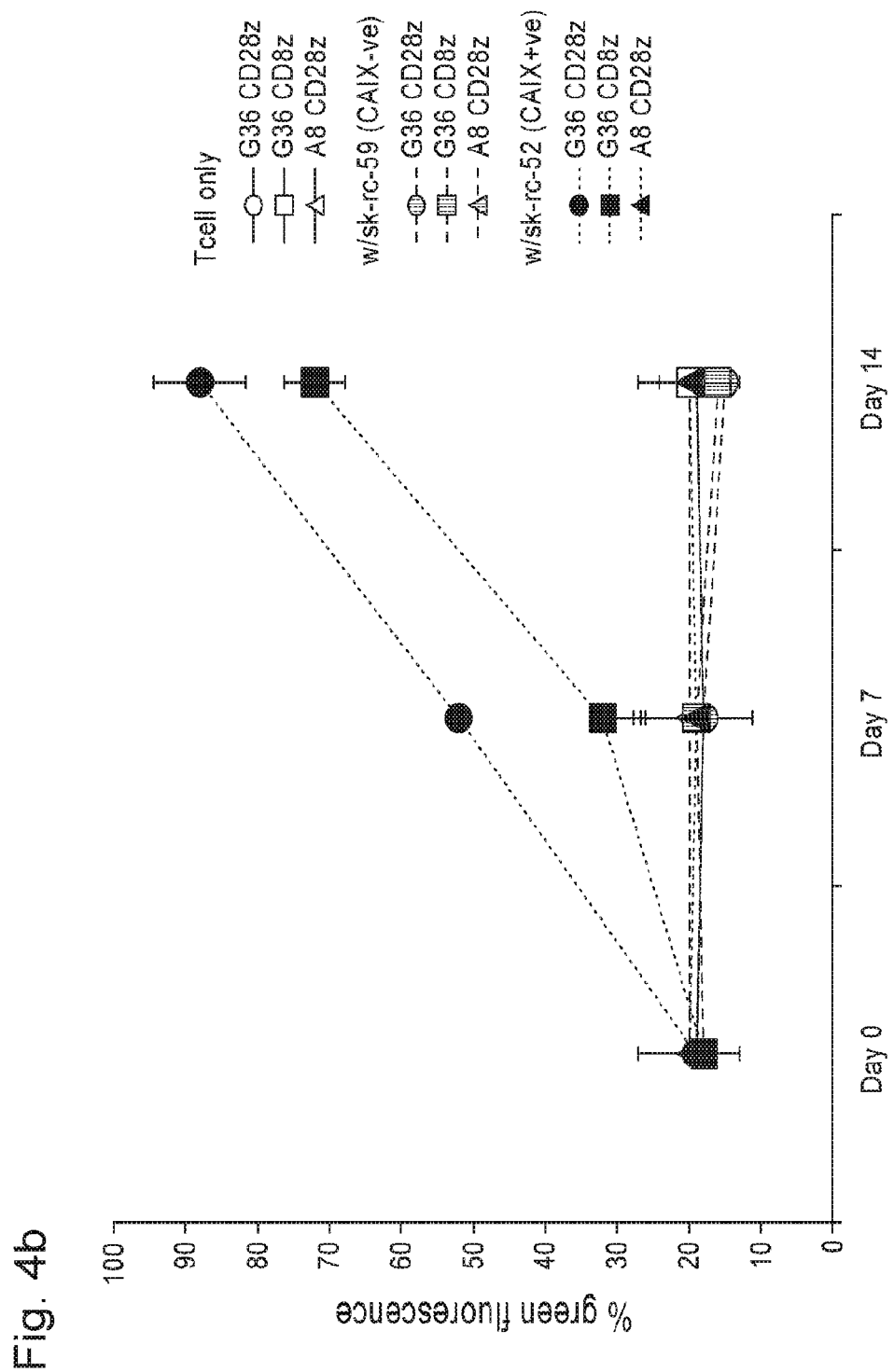

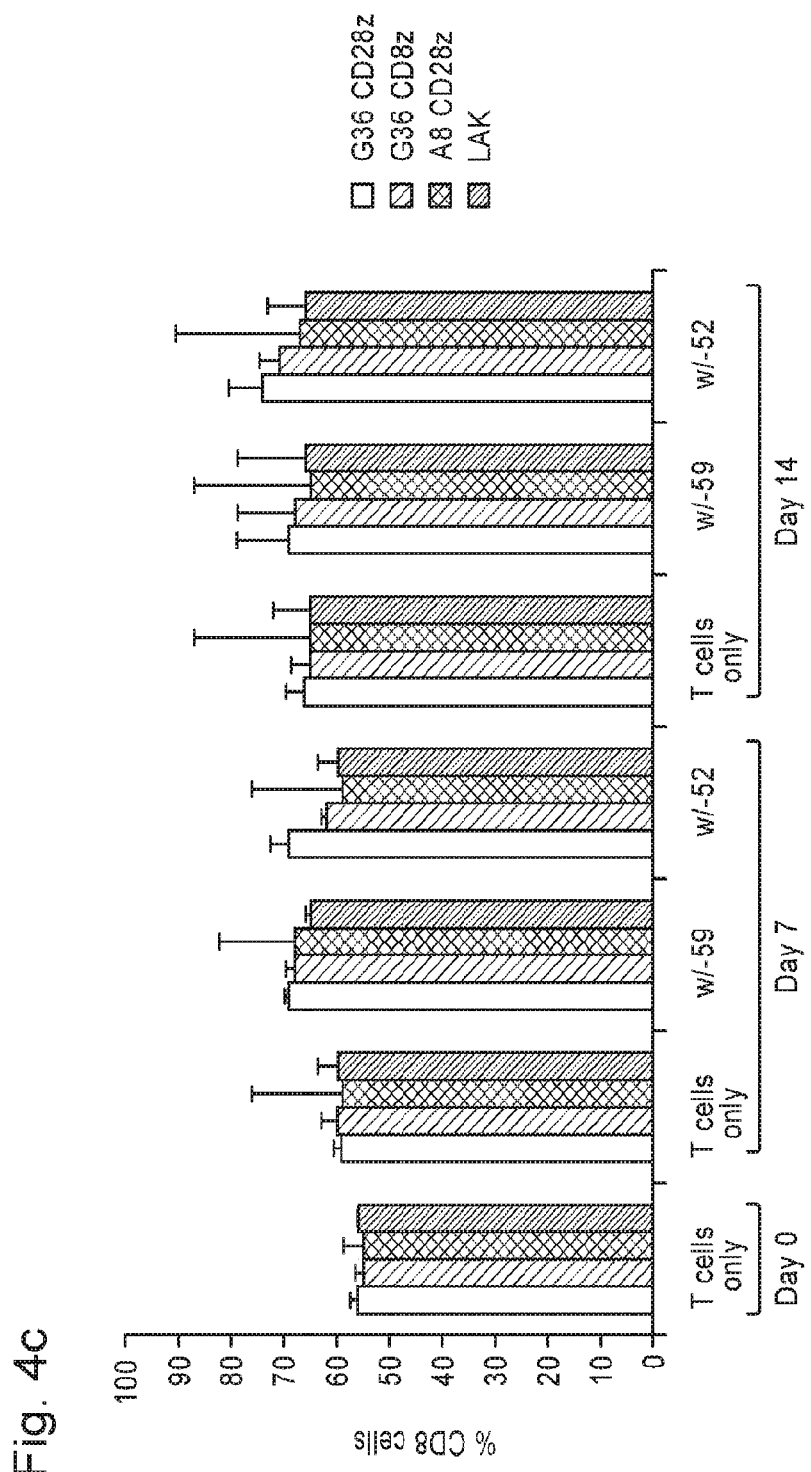

Experiment 1

Experiment 2

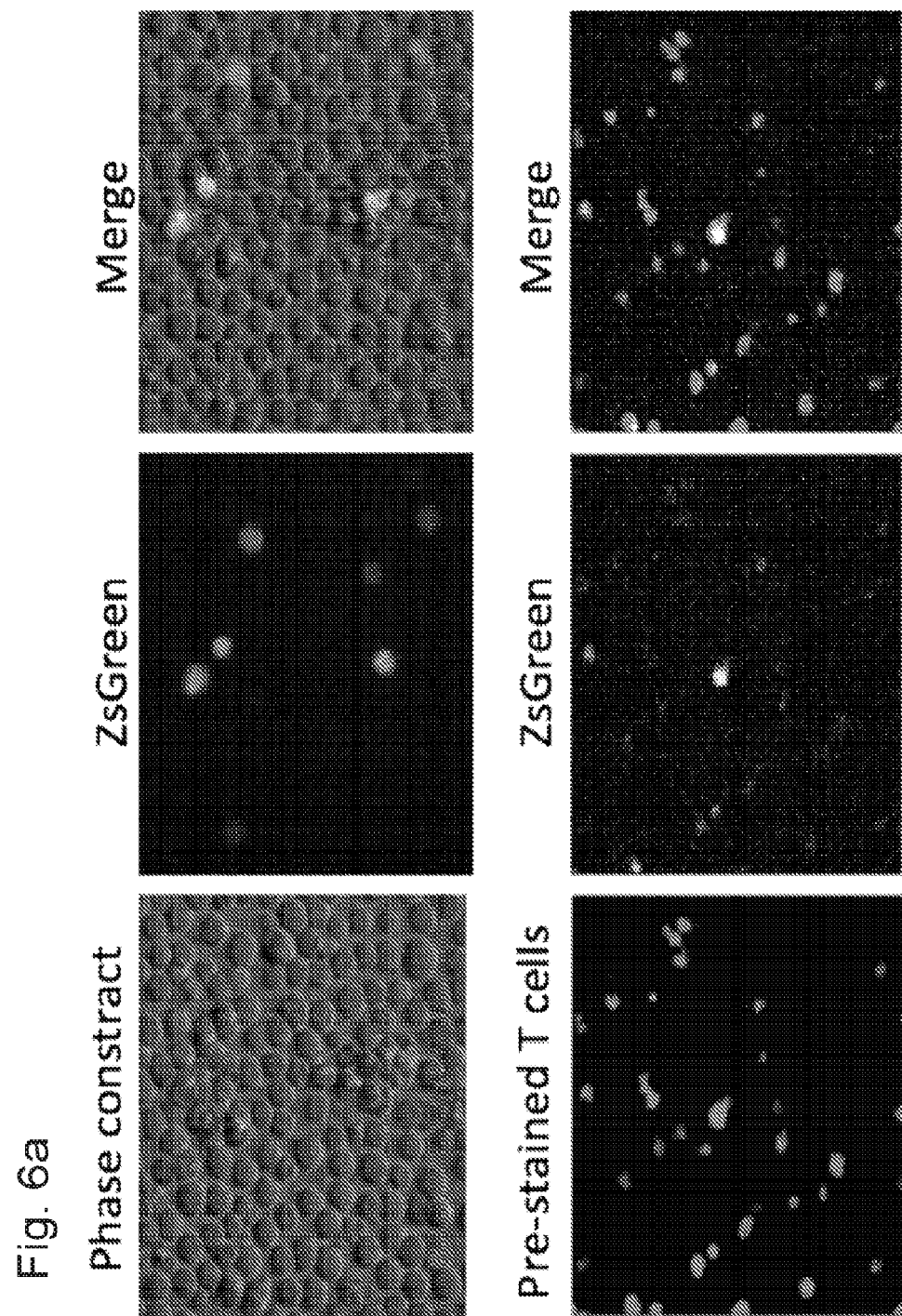

40x 200x

SEQUENCE LISTING

```
<160> NUMBER OF SEQ ID NOS: 110

<210> SEQ ID NO 1
<211> LENGTH: 121
<212> TYPE: PRT
<213> ORGANISM: Homo sapiens

<400> SEQUENCE: 1

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Gly Asn Tyr Arg Gly Ser Leu Ala Phe Asp Ile Trp Gly
            100                 105                 110
```

```
Gln Gly Thr Leu Val Thr Val Ser Ser
        115                 120

<210> SEQ ID NO 2
<211> LENGTH: 113
<212> TYPE: PRT
<213> ORGANISM: Homo sapiens

<400> SEQUENCE: 2

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Asn Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Trp Val Val Phe Gly Gly Gly Thr Lys Leu Thr Val Leu
            100                 105                 110

Gly

<210> SEQ ID NO 3
<211> LENGTH: 119
<212> TYPE: PRT
<213> ORGANISM: Homo sapiens

<400> SEQUENCE: 3

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Ala Asn Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 4
<211> LENGTH: 119
<212> TYPE: PRT
<213> ORGANISM: Homo sapiens

<400> SEQUENCE: 4

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30
```

```
Ala Met Ser Trp Val Arg Gln Ala Pro Gly Lys Gly Leu Glu Trp Val
         35                   40                  45

Ser Ala Ile Ser Ala Asn Gly Gly Thr Thr Tyr Tyr Ala Asp Ser Val
    50                   55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Asn Asn Gly Asn Tyr Arg Gly Ala Phe Asp Ile Trp Gly Gln Gly
            100                 105                 110

Thr Met Val Thr Val Ser Ser
        115
```

<210> SEQ ID NO 5
<211> LENGTH: 119
<212> TYPE: PRT
<213> ORGANISM: Homo sapiens

<400> SEQUENCE: 5

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
             20                  25                  30

Ala Met Ser Trp Val Arg Gln Ala Pro Gly Lys Gly Leu Glu Trp Val
         35                   40                  45

Ser Ala Ile Ser Ala Asn Gly Gly Thr Thr Tyr Tyr Ala Asp Ser Val
    50                   55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Asn Asn Gly Asn Tyr Arg Gly Ala Phe Asp Ile Trp Gly Gln Gly
            100                 105                 110

Thr Met Val Thr Val Ser Ser
        115
```

<210> SEQ ID NO 6
<211> LENGTH: 119
<212> TYPE: PRT
<213> ORGANISM: Homo sapiens

<400> SEQUENCE: 6

```
Gln Val Gln Leu Val Gln Ser Gly Gly Gly Leu Val Gln Pro Gly Gly
1               5                   10                  15

Ser Leu Arg Leu Ser Cys Ala Ala Ser Glu Phe Thr Phe Gly Thr Tyr
             20                  25                  30

Ala Met Thr Trp Val Arg Gln Ala Pro Gly Lys Gly Leu Glu Trp Val
         35                   40                  45

Ser Ala Val Ser Gly Ser Gly Gly Ser Thr Tyr Tyr Ala Asp Ser Val
    50                   55                  60

Lys Gly Arg Phe Thr Ile Ser Arg Asp Asn Ser Arg Asn Thr Leu Tyr
65                   70                  75                  80

Leu Gln Met Asn Ser Leu Arg Ala Asp Asp Thr Ala Val Tyr Tyr Cys
                 85                  90                  95

Ala Arg Gly Pro Val Leu Arg Tyr Gly Phe Asp Ile Trp Gly Gln Gly
            100                 105                 110
```

```
Thr Met Val Thr Val Ser Ser
        115

<210> SEQ ID NO 7
<211> LENGTH: 119
<212> TYPE: PRT
<213> ORGANISM: Homo sapiens

<400> SEQUENCE: 7

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 8
<211> LENGTH: 118
<212> TYPE: PRT
<213> ORGANISM: Homo sapiens

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser Ala Tyr Ser Gly Tyr Asp Leu Trp Gly Gln Gly Thr
            100                 105                 110

Leu Val Thr Val Ser Ser
        115

<210> SEQ ID NO 9
<211> LENGTH: 119
<212> TYPE: PRT
<213> ORGANISM: Homo sapiens

<400> SEQUENCE: 9

Gln Val Gln Leu Val Gln Ser Gly Gly Gly Leu Val Arg Pro Gly Gly
1               5                   10                  15
```

```
Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Thr Val Thr Val Ser Ser
            115
```

<210> SEQ ID NO 10
<211> LENGTH: 119
<212> TYPE: PRT
<213> ORGANISM: Homo sapiens

<400> SEQUENCE: 10

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
            115
```

<210> SEQ ID NO 11
<211> LENGTH: 119
<212> TYPE: PRT
<213> ORGANISM: Homo sapiens

<400> SEQUENCE: 11

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Asn Asn Gly Asn Tyr Arg Gly Ala Phe Asp Ile Trp Gly Gln Gly
                100                 105                 110

Thr Thr Val Thr Val Ser Ser
            115

<210> SEQ ID NO 12
<211> LENGTH: 116
<212> TYPE: PRT
<213> ORGANISM: Homo sapiens

<400> SEQUENCE: 12

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Gly Phe Asp Tyr Trp Gly Gln Gly Thr Leu Val
                100                 105                 110

Thr Val Ser Ser
        115

<210> SEQ ID NO 13
<211> LENGTH: 119
<212> TYPE: PRT
<213> ORGANISM: Homo sapiens

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Arg Tyr Ser Ser Leu Gly Tyr Trp Gly Gln Gly
                100                 105                 110

Thr Leu Val Thr Val Ser Ser
        115

<210> SEQ ID NO 14
<211> LENGTH: 122
<212> TYPE: PRT
<213> ORGANISM: Homo sapiens

<400> SEQUENCE: 14

Gln Val Gln Leu Val Gln Ser Gly Gly Gly Val Val Gln Pro Gly Arg
```

```
                1               5                   10                  15
            Ser Leu Arg Leu Ser Cys Ala Ala Ser Gly Phe Thr Phe Ser Ser Tyr
                        20                  25                  30
            Gly Met His Trp Val Arg Gln Ala Pro Gly Lys Gly Leu Glu Trp Val
                        35                  40                  45
            Ala Val Ile Ser Tyr Asp Gly Ser Asn Lys Tyr Tyr Ala Asp Ser Val
                        50                  55                  60
            Lys Gly Arg Phe Thr Ile Ser Arg Asp Asn Ser Lys Asn Thr Leu Tyr
             65                 70                  75                  80
            Leu Gln Met Asn Ser Leu Arg Ala Glu Asp Thr Ala Val Tyr Tyr Cys
                        85                  90                  95
            Ala Arg Glu Ala Pro Tyr Ser Ser Leu Asp Ala Phe Asp Ile Trp
                        100                 105                 110
            Gly Gln Gly Thr Met Val Thr Val Ser Ser
                        115                 120

<210> SEQ ID NO 15
<211> LENGTH: 118
<212> TYPE: PRT
<213> ORGANISM: Homo sapiens

<400> SEQUENCE: 15

Gln Val Gln Leu Gln Glu Ser Gly Gly Gly Leu Val Gln Pro Gly Gly
             1               5                   10                  15
            Ser Leu Arg Leu Ser Cys Ala Ala Ser Gly Phe Thr Phe Ser Ser Tyr
                        20                  25                  30
            Ala Met Ser Trp Val Arg Gln Ala Pro Gly Lys Gly Leu Glu Trp Val
                        35                  40                  45
            Ser Ala Ile Ser Gly Ser Gly Gly Ser Thr Tyr Tyr Ala Asp Ser Val
                        50                  55                  60
            Lys Gly Arg Phe Thr Ile Ser Arg Asp Asn Ser Lys Asn Thr Leu Tyr
             65                 70                  75                  80
            Leu Gln Met Asn Ser Leu Arg Ala Glu Asp Thr Ala Val Tyr Tyr Cys
                        85                  90                  95
            Ala Arg Ser His Ser Ser Gly Gly Phe Asp Tyr Trp Gly Gln Gly Thr
                        100                 105                 110
            Leu Val Thr Val Ser Ser
                        115

<210> SEQ ID NO 16
<211> LENGTH: 118
<212> TYPE: PRT
<213> ORGANISM: Homo sapiens

<400> SEQUENCE: 16

Gln Val Gln Leu Gln Glu Ser Gly Gly Gly Leu Val Gln Pro Gly Gly
             1               5                   10                  15
            Ser Leu Arg Leu Ser Cys Ala Ala Ser Gly Phe Thr Phe Ser Ser Tyr
                        20                  25                  30
            Ala Met Ser Trp Val Arg Gln Ala Pro Gly Lys Gly Leu Glu Trp Val
                        35                  40                  45
            Ser Ala Ile Ser Gly Ser Gly Gly Ser Thr Tyr Tyr Ala Asp Ser Val
                        50                  55                  60
            Lys Gly Arg Phe Thr Ile Ser Arg Asp Asn Ser Lys Asn Thr Leu Tyr
             65                 70                  75                  80
            Leu Gln Met Asn Ser Leu Arg Ala Glu Asp Thr Ala Val Tyr Tyr Cys
```

```
                    85                  90                  95
Ala Arg Ser His Ser Ser Gly Gly Phe Asp Tyr Trp Gly Gln Gly Thr
                100                 105                 110
Leu Val Thr Val Ser Ser
            115

<210> SEQ ID NO 17
<211> LENGTH: 116
<212> TYPE: PRT
<213> ORGANISM: Homo sapiens

<400> SEQUENCE: 17

Gln Val Thr Leu Lys Glu Ser Gly Gly Val Val Gln Pro Gly Thr
1               5                   10                  15
Ser Leu Arg Leu Ser Cys Ala Ala Ser Gly Phe Thr Phe Ser Asn Tyr
                20                  25                  30
Ala Met Thr Trp Val Arg Gln Ala Pro Gly Lys Gly Leu Glu Trp Val
            35                  40                  45
Gly Leu Ile Ser Tyr Asp Gly Ser Val Thr His Tyr Thr Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Thr Leu Arg Ala Asp Asp Thr Ala Val Tyr Tyr Cys
                85                  90                  95
Ala Arg Gly Ser Gly Tyr Gln Glu His Trp Gly Gln Gly Thr Leu Val
                100                 105                 110
Thr Val Ser Ser
            115

<210> SEQ ID NO 18
<211> LENGTH: 118
<212> TYPE: PRT
<213> ORGANISM: Homo sapiens

<400> SEQUENCE: 18

Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Thr Tyr Gly Asp Tyr Gly Ser Leu Asp Tyr Trp Gly Gln Gly Thr
                100                 105                 110
Leu Val Thr Val Ser Ser
            115

<210> SEQ ID NO 19
<211> LENGTH: 122
<212> TYPE: PRT
<213> ORGANISM: Homo sapiens

<400> SEQUENCE: 19
```

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Val Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Tyr Cys Ser Ser Thr Ser Cys Tyr Arg Gly Met Asp Val Trp
            100                 105                 110

Gly Lys Gly Thr Leu Val Thr Val Ser Ser
            115                 120

<210> SEQ ID NO 20
<211> LENGTH: 119
<212> TYPE: PRT
<213> ORGANISM: Homo sapiens

<400> SEQUENCE: 20

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Arg Ala Ala Arg Pro Pro Phe Asp Tyr Trp Gly Gln Gly
            100                 105                 110

Thr Leu Val Thr Val Ser Ser
            115

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 22
<211> LENGTH: 121
<212> TYPE: PRT
<213> ORGANISM: Homo sapiens

<400> SEQUENCE: 22

Gln Val Gln Leu Val Gln Ser Gly Gly Gly Leu Val Gln Pro Gly Gly
1               5                   10                  15

Ser Leu Arg Leu Ser Cys Ala Ala Pro Glu Phe Thr Phe Ser Lys Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Arg Ser Gly Tyr Phe Leu Pro Leu Asp Tyr Trp Gly
            100                 105                 110

Gln Gly Thr Leu Val Thr Val Ser Ser
        115                 120

<210> SEQ ID NO 23
<211> LENGTH: 118
<212> TYPE: PRT
<213> ORGANISM: Homo sapiens

<400> SEQUENCE: 23

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Val Thr Gly Gly Phe Asp Pro Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Homo sapiens -continued

<400> SEQUENCE: 24

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Ser Arg
                85                  90                  95

Leu Ser Ala Trp Val Phe Gly Gly Gly Thr Lys Leu Thr Val Leu Gly
            100                 105                 110

<210> SEQ ID NO 25
<211> LENGTH: 111
<212> TYPE: PRT
<213> ORGANISM: Homo sapiens

<400> SEQUENCE: 25

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Ser Ser Ala Ser Leu Ala Ile Thr Gly Leu
65                  70                  75                  80

Gln Ala Glu Asp Glu Ala His Tyr Tyr Cys Gln Ser Tyr Asp Arg Ser
                85                  90                  95

Leu Ser Trp Val Phe Gly Gly Gly Thr Lys Leu Thr Val Leu Gly
            100                 105                 110

<210> SEQ ID NO 26
<211> LENGTH: 112
<212> TYPE: PRT
<213> ORGANISM: Homo sapiens

<400> SEQUENCE: 26

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Ala Asp Asp Glu Ala Asp Tyr Tyr Cys Gln Ser Tyr Asp Ser Thr
                85                  90                  95

```
Leu Arg Val Trp Met Phe Gly Gly Gly Thr Lys Leu Thr Val Leu Gly
                100                 105                 110
```

<210> SEQ ID NO 27
<211> LENGTH: 112
<212> TYPE: PRT
<213> ORGANISM: Homo sapiens

<400> SEQUENCE: 27

```
Gln Ser Val Leu Thr Gln Pro Pro Ser Val Ser Gly Ala Pro Gly Gln
1               5                   10                  15

Arg Ile Thr Ile Ser Cys Thr Gly Ser Arg Ser Asn Ile Gly Ala Asp
                20                  25                  30

Tyr Asp Val His Trp Tyr Gln Gln Leu Pro Gly Thr Ala Pro Lys Leu
            35                  40                  45

Leu Ile Tyr Ala Asn Asn Asn Arg Pro Ser Gly Val Pro Gly Arg Phe
        50                  55                  60

Ser Ala Ser Lys Ser Gly Thr Ser Ala Ser Leu Ala Ile Ser Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
                100                 105                 110
```

<210> SEQ ID NO 28
<211> LENGTH: 112
<212> TYPE: PRT
<213> ORGANISM: Homo sapiens

<400> SEQUENCE: 28

```
Gln Ser Val Leu Thr Gln Pro Pro Ser Val Ser Gly Ala Pro Gly Gln
1               5                   10                  15

Arg Ile Thr Ile Ser Cys Thr Gly Ser Arg Ser Asn Ile Gly Ala Asp
                20                  25                  30

Tyr Asp Val His Trp Tyr Gln Gln Leu Pro Gly Thr Ala Pro Lys Leu
            35                  40                  45

Leu Ile Tyr Ala Asn Asn Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Gly
                100                 105                 110
```

<210> SEQ ID NO 29
<211> LENGTH: 111
<212> TYPE: PRT
<213> ORGANISM: Homo sapiens

<400> SEQUENCE: 29

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
                20                  25                  30

Tyr Asn Val His Trp Tyr Gln Gln Leu Pro Gly Thr Ala Pro Lys Leu
            35                  40                  45

Leu Ile Tyr Asp Asn Thr Asn Arg Pro Ser Gly Val Pro Ala Arg Phe
```

```
                    50                  55                  60
Ser Gly Ser Lys Ser Ala Thr Ser Ala Ser Leu Thr Ile Thr Gly Leu
 65                  70                  75                  80

Gln Ala Asp Asp Glu Ala Asp Tyr Tyr Cys Gln Ser Tyr Asp Ser Gly
                     85                  90                  95

Leu Arg Trp Val Phe Gly Gly Gly Thr Lys Leu Thr Leu Leu Gly
                100                 105                 110
```

<210> SEQ ID NO 30
<211> LENGTH: 111
<212> TYPE: PRT
<213> ORGANISM: Homo sapiens

<400> SEQUENCE: 30

```
Gln Ser Val Leu Thr Gln Pro Pro Ser Val Ser Gly Ala Pro Gly Gln
  1               5                  10                  15

Arg Ile Thr Ile Ser Cys Thr Gly Ser Ser Asn Ile Gly Ala Gly
                 20                  25                  30

Tyr Asp Val His Trp Tyr Gln Gln Val Pro Gly Lys Ala Pro Lys Val
                 35                  40                  45

Val Ile Tyr Gly Asn Asn Asn Arg Pro Ser Gly Val Pro Asp Arg Phe
             50                  55                  60

Ser Gly Ser Lys Ser Gly Ala Ser Ala Ser Leu Ala Ile Thr Gly Leu
 65                  70                  75                  80

Gln Thr Glu Asp Glu Ala Asp Tyr Tyr Cys Gln Ser Tyr Asp Lys Ser
                     85                  90                  95

Leu Thr Trp Val Phe Gly Gly Gly Thr Lys Val Thr Val Leu Gly
                100                 105                 110
```

<210> SEQ ID NO 31
<211> LENGTH: 111
<212> TYPE: PRT
<213> ORGANISM: Homo sapiens

<400> SEQUENCE: 31

```
Gln Ser Val Leu Thr Gln Pro Pro Ser Val Ser Gly Ala Pro Gly Gln
  1               5                  10                  15

Arg Ile Thr Ile Ser Cys Thr Gly Thr Ser Asn Ile Gly Ala Gly
                 20                  25                  30

Tyr Asp Val His Trp Tyr Gln Gln Leu Pro Gly Ala Ala Pro Arg Val
                 35                  40                  45

Leu Ile Tyr Gly Asn Asn Asn Arg Pro Ser Gly Val Pro Asp Arg Phe
             50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Gln Ser Tyr Asp Lys Ser
                     85                  90                  95

Leu Ser Trp Val Phe Gly Gly Gly Thr Lys Leu Thr Val Leu Arg
                100                 105                 110
```

<210> SEQ ID NO 32
<211> LENGTH: 112
<212> TYPE: PRT
<213> ORGANISM: Homo sapiens

<400> SEQUENCE: 32

```
Gln Ser Val Leu Thr Gln Pro Pro Ser Val Ser Gly Ala Pro Gly Gln
  1               5                  10                  15
```

-continued

Arg Val Thr Ile Ser Cys Thr Gly Ser Ser Asn Ile Gly Ala Gly
            20                  25                  30

Phe Asp Val His Trp Tyr Gln Gln Leu Pro Gly Thr Ala Pro Arg Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Arg
            100                 105                 110

<210> SEQ ID NO 33
<211> LENGTH: 112
<212> TYPE: PRT
<213> ORGANISM: Homo sapiens

<400> SEQUENCE: 33

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Asp Asp Thr Asn Arg Pro Ser Gly Val Pro His Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
            100                 105                 110

<210> SEQ ID NO 34
<211> LENGTH: 111
<212> TYPE: PRT
<213> ORGANISM: Homo sapiens

<400> SEQUENCE: 34

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Asp Asn Thr Asn Arg Pro Ser Gly Val Pro Ala Arg Phe
    50                  55                  60

Ser Gly Ser Lys Ser Ala Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Gly
                85                  90                  95

Leu Arg Trp Val Phe Gly Gly Gly Thr Lys Leu Thr Leu Leu Arg
            100                 105                 110

<210> SEQ ID NO 35

```
<211> LENGTH: 111
<212> TYPE: PRT
<213> ORGANISM: Homo sapiens

<400> SEQUENCE: 35

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Arg Gly
            20                  25                  30

Tyr Asn Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Ser Ser Gly Asn Thr Ala Ser Leu Thr Ile Thr Gly Ala
65                  70                  75                  80

Gln Ala Glu Asp Glu Ala Asp Tyr Tyr Cys His Ser Arg Asp Asn Asn
                85                  90                  95

Gly His His Ile Phe Gly Gly Gly Thr Lys Leu Thr Val Leu Ser
            100                 105                 110

<210> SEQ ID NO 36
<211> LENGTH: 112
<212> TYPE: PRT
<213> ORGANISM: Homo sapiens

<400> SEQUENCE: 36

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
            35                  40                  45

Leu Ile Tyr Gly Asn Thr Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Gly Asp Tyr Tyr Cys Gln Ser Tyr Asp Ser Ser
                85                  90                  95

Leu Ser Ala Trp Val Phe Gly Gly Gly Thr Lys Leu Thr Val Leu Gly
            100                 105                 110

<210> SEQ ID NO 37
<211> LENGTH: 112
<212> TYPE: PRT
<213> ORGANISM: Homo sapiens
<220> FEATURE:
<221> NAME/KEY: misc_feature
<222> LOCATION: (83)..(83)
<223> OTHER INFORMATION: Xaa can be any naturally occurring amino acid

<400> SEQUENCE: 37

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
            35                  40                  45

Leu Ile Tyr Gly Asn Thr Asn Arg Pro Ser Gly Val Pro Asp Arg Phe
50                  55                  60
```

```
Ser Gly Ser Lys Ser Gly Thr Ser Ala Ser Leu Ala Ile Thr Gly Leu
65                  70                  75                  80

Gln Ala Xaa Asp Glu Gly Asp Tyr Tyr Cys Gln Ser Tyr Asp Ser Ser
                85                  90                  95

Leu Ser Ala Trp Val Phe Gly Gly Gly Thr Lys Leu Thr Val Leu Gly
            100                 105                 110

<210> SEQ ID NO 38
<211> LENGTH: 110
<212> TYPE: PRT
<213> ORGANISM: Homo sapiens

<400> SEQUENCE: 38

Leu Pro Val Leu Thr Gln Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

His Val Val Phe Gly Gly Gly Thr Lys Leu Thr Val Leu Gly
            100                 105                 110

<210> SEQ ID NO 39
<211> LENGTH: 112
<212> TYPE: PRT
<213> ORGANISM: Homo sapiens

<400> SEQUENCE: 39

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Tyr Asp Ser Ser
                85                  90                  95

Leu Arg Ala Trp Val Phe Gly Gly Gly Thr Lys Leu Ala Val Leu Gly
            100                 105                 110

<210> SEQ ID NO 40
<211> LENGTH: 112
<212> TYPE: PRT
<213> ORGANISM: Homo sapiens

<400> SEQUENCE: 40

Gln Ser Val Leu Thr Gln Pro Pro Ser Val Ser Gly Ala Pro Gly Gln
1               5                   10                  15
```

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Ala Asn Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
                100                 105                 110

<210> SEQ ID NO 41
<211> LENGTH: 111
<212> TYPE: PRT
<213> ORGANISM: Homo sapiens

<400> SEQUENCE: 41

Gln Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Pro
                35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Arg
                100                 105                 110

<210> SEQ ID NO 42
<211> LENGTH: 112
<212> TYPE: PRT
<213> ORGANISM: Homo sapiens

<400> SEQUENCE: 42

Gln Ser Val Leu Thr Gln Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln His Leu Pro Gly Thr Ala Pro Lys Leu
                35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Gly
                100                 105                 110

<210> SEQ ID NO 43
<211> LENGTH: 109

```
<212> TYPE: PRT
<213> ORGANISM: Homo sapiens

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asn Ser Leu Arg Tyr Tyr Tyr Pro
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Thr Gln Ala Glu
65                  70                  75                  80

Asp Glu Ala Asp Tyr Tyr Cys Ser Ser Arg Asp Asn Thr Asp Asn Arg
                85                  90                  95

Val Val Phe Gly Gly Gly Thr Lys Leu Thr Val Leu Gly
            100                 105

<210> SEQ ID NO 44
<211> LENGTH: 109
<212> TYPE: PRT
<213> ORGANISM: Homo sapiens

<400> SEQUENCE: 44

Gln Pro Gly Leu Thr Gln Pro Pro Ser Val Ser Val Ala Pro Gly Gln
1               5                   10                  15

Thr Ala Arg Ile Thr Cys Gly Gly Asp Asn Ile Gly Arg Lys Ser Val
            20                  25                  30

His Trp Tyr Gln Gln Arg Pro Gly Gln Ala Pro Ile Leu Val Ile Arg
        35                  40                  45

Asp Asp Arg Asp Arg Pro Ser Gly Ile Pro Glu Arg Phe Ser Gly Ser
    50                  55                  60

Ser Ser Val Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Lys His
                85                  90                  95

Tyr Val Phe Gly Pro Gly Thr Lys Val Thr Ala Leu Gly
            100                 105

<210> SEQ ID NO 45
<211> LENGTH: 458
<212> TYPE: PRT
<213> ORGANISM: Homo sapiens

<400> SEQUENCE: 45

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Met Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
```

```
            85                  90                  95
Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
            115                 120                 125

Ala His Arg Asp Lys Glu Gly Asp Asp Gln Ser His Trp Arg Tyr Gly
            130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                    165                 170                 175

Leu Arg Pro Leu Glu Leu Leu Gly Phe Gln Leu Pro Pro Leu Pro Glu
                    180                 185                 190

Leu Arg Leu Arg Asn Asn Gly His Ser Val Gln Leu Thr Leu Pro Pro
            195                 200                 205

Gly Leu Glu Met Ala Leu Gly Pro Gly Arg Glu Tyr Ala Leu Gln Leu
            210                 215                 220

His Leu His Trp Gly Ala Ala Gly Arg Pro Gly Ser Glu His Thr Val
225                 230                 235                 240

Glu Gly His Arg Phe Pro Ala Glu Ile His Val Val His Leu Ser Thr
                    245                 250                 255

Ala Phe Ala Arg Val Asp Glu Ala Leu Gly Arg Pro Gly Gly Leu Ala
                    260                 265                 270

Val Leu Ala Ala Phe Leu Glu Glu Gly Pro Glu Glu Asn Ser Ala Tyr
            275                 280                 285

Glu Gln Leu Leu Ser Arg Leu Glu Glu Ile Ala Glu Glu Gly Ser Glu
            290                 295                 300

Thr Gln Val Pro Gly Leu Asp Ile Ser Ala Leu Leu Pro Ser Asp Phe
305                 310                 315                 320

Ser Arg Tyr Phe Gln Tyr Glu Gly Ser Leu Thr Thr Pro Pro Cys Ala
                    325                 330                 335

Gln Gly Val Ile Trp Thr Val Phe Asn Gln Thr Val Met Leu Ser Ala
                    340                 345                 350

Lys Gln Leu His Thr Leu Ser Asp Thr Leu Trp Gly Pro Gly Asp Ser
            355                 360                 365

Arg Leu Gln Leu Asn Phe Arg Ala Thr Gln Pro Leu Asn Gly Arg Val
            370                 375                 380

Ile Glu Ala Ser Phe Pro Ala Gly Val Asp Ser Ser Pro Arg Ala Ala
385                 390                 395                 400

Glu Pro Val Gln Leu Asn Ser Cys Leu Ala Ala Gly Asp Ile Leu Ala
                    405                 410                 415

Leu Val Phe Gly Leu Leu Phe Ala Val Thr Ser Val Ala Phe Leu Val
                    420                 425                 430

Gln Met Arg Arg Gln His Arg Arg Gly Thr Lys Gly Gly Val Ser Tyr
            435                 440                 445

Arg Pro Ala Glu Val Ala Glu Thr Gly Ala
            450                 455

<210> SEQ ID NO 46
<211> LENGTH: 437
<212> TYPE: PRT
<213> ORGANISM: Mus musculus

<400> SEQUENCE: 46
```

```
Met Ala Ser Leu Gly Pro Ser Pro Trp Ala Pro Leu Ser Thr Pro Ala
1               5                   10                  15

Pro Thr Ala Gln Leu Leu Leu Phe Leu Leu Gln Val Ser Ala Gln
            20                  25                  30

Pro Gln Gly Leu Ser Gly Met Gln Gly Glu Pro Ser Leu Gly Asp Ser
            35                  40                  45

Ser Ser Gly Glu Asp Glu Leu Gly Val Asp Val Leu Pro Ser Glu Glu
    50                  55                  60

Asp Ala Pro Glu Glu Ala Asp Pro Asp Gly Glu Asp Pro Pro Glu
65                  70                  75                  80

Val Asn Ser Glu Asp Arg Met Glu Glu Ser Leu Gly Leu Glu Asp Leu
                85                  90                  95

Ser Thr Pro Glu Ala Pro Glu His Ser Gln Gly Ser His Gly Asp Glu
            100                 105                 110

Lys Gly Gly Gly His Ser His Trp Ser Tyr Gly Gly Thr Leu Leu Trp
            115                 120                 125

Pro Gln Val Ser Pro Ala Cys Ala Gly Arg Phe Gln Ser Pro Val Asp
    130                 135                 140

Ile Arg Leu Glu Arg Thr Ala Phe Cys Arg Thr Leu Gln Pro Leu Glu
145                 150                 155                 160

Leu Leu Gly Tyr Glu Leu Gln Pro Leu Pro Glu Leu Ser Leu Ser Asn
                165                 170                 175

Asn Gly His Thr Val Gln Leu Thr Leu Pro Pro Gly Leu Lys Met Ala
            180                 185                 190

Leu Gly Pro Gly Gln Glu Tyr Arg Ala Leu Gln Leu His Leu His Trp
            195                 200                 205

Gly Thr Ser Asp His Pro Gly Ser Glu His Thr Val Asn Gly His Arg
210                 215                 220

Phe Pro Ala Glu Ile His Val Val His Leu Ser Thr Ala Phe Ser Glu
225                 230                 235                 240

Leu His Glu Ala Leu Gly Arg Pro Gly Gly Leu Ala Val Leu Ala Ala
            245                 250                 255

Phe Leu Gln Glu Ser Pro Glu Glu Asn Ser Ala Tyr Glu Gln Leu Leu
            260                 265                 270

Ser His Leu Glu Glu Ile Ser Glu Glu Gly Ser Lys Ile Glu Ile Pro
    275                 280                 285

Gly Leu Asp Val Ser Ala Leu Leu Pro Ser Asp Phe Ser Arg Tyr Tyr
    290                 295                 300

Arg Tyr Glu Gly Ser Leu Thr Thr Pro Pro Cys Ser Gln Gly Val Ile
305                 310                 315                 320

Trp Thr Val Phe Asn Glu Thr Val Lys Leu Ser Ala Lys Gln Leu His
                325                 330                 335

Thr Leu Ser Val Ser Leu Trp Gly Pro Arg Asp Ser Arg Leu Gln Leu
            340                 345                 350

Asn Phe Arg Ala Thr Gln Pro Leu Asn Gly Arg Thr Ile Glu Ala Ser
            355                 360                 365

Phe Pro Ala Ala Glu Asp Ser Ser Pro Glu Pro Val His Val Asn Ser
370                 375                 380

Cys Phe Thr Ala Gly Asp Ile Leu Ala Leu Val Phe Gly Leu Leu Phe
385                 390                 395                 400

Ala Val Thr Ser Ile Ala Phe Leu Leu Gln Leu Arg Arg Gln His
                405                 410                 415

His Arg Ser Gly Thr Lys Asp Arg Val Ser Tyr Ser Pro Ala Glu Met
```

Thr Glu Thr Gly Ala
    435

<210> SEQ ID NO 47
<211> LENGTH: 38
<212> TYPE: DNA
<213> ORGANISM: Artificial sequence
<220> FEATURE:
<223> OTHER INFORMATION: Chemically synthesized primer

<400> SEQUENCE: 47
atcgacgcgt gcctgagcga ggtgcagctg gtgcagtc                             38

<210> SEQ ID NO 48
<211> LENGTH: 32
<212> TYPE: DNA
<213> ORGANISM: Artificial sequence
<220> FEATURE:
<223> OTHER INFORMATION: Chemically synthesized primer

<400> SEQUENCE: 48
caatggtcac cgtctcttca gctagcacca gg                                   32

<210> SEQ ID NO 49
<211> LENGTH: 35
<212> TYPE: DNA
<213> ORGANISM: Artificial sequence
<220> FEATURE:
<223> OTHER INFORMATION: Chemically synthesized primer

<400> SEQUENCE: 49
atcccaagct taagccagtc tgtgctgact cagcc                                35

<210> SEQ ID NO 50
<211> LENGTH: 31
<212> TYPE: DNA
<213> ORGANISM: Artificial sequence
<220> FEATURE:
<223> OTHER INFORMATION: Chemically synthesized primer

<400> SEQUENCE: 50
ggagggacca aattgaccgt cctaggtcag c                                    31

<210> SEQ ID NO 51
<211> LENGTH: 41
<212> TYPE: DNA
<213> ORGANISM: Artificial sequence
<220> FEATURE:
<223> OTHER INFORMATION: Chemically synthesized primer

<400> SEQUENCE: 51
tagggcacgc gtgtgctgag cgaggtgcag ctggtgcagt c                         41

<210> SEQ ID NO 52
<211> LENGTH: 32
<212> TYPE: DNA
<213> ORGANISM: Artificial sequence
<220> FEATURE:
<223> OTHER INFORMATION: Chemically synthesized primer

<400> SEQUENCE: 52
tctagtgcta gctgaagaga cggtgaccat tg                                   32

<210> SEQ ID NO 53

```
<211> LENGTH: 35
<212> TYPE: DNA
<213> ORGANISM: Artificial sequence
<220> FEATURE:
<223> OTHER INFORMATION: Chemically synthesized primer

<400> SEQUENCE: 53
ctagcaagct tatcccagtc tgtgctgact cagcc                            35

<210> SEQ ID NO 54
<211> LENGTH: 26
<212> TYPE: DNA
<213> ORGANISM: Artificial sequence
<220> FEATURE:
<223> OTHER INFORMATION: Chemically synthesized primer

<400> SEQUENCE: 54
atagcaccta ggacggtcag cttggt                                      26

<210> SEQ ID NO 55
<211> LENGTH: 5
<212> TYPE: PRT
<213> ORGANISM: Artificial sequence
<220> FEATURE:
<223> OTHER INFORMATION: Portion of CDR1 heavy chain sequence

<400> SEQUENCE: 55

Ser Tyr Ala Met Ser
1               5

<210> SEQ ID NO 56
<211> LENGTH: 5
<212> TYPE: PRT
<213> ORGANISM: Artificial sequence
<220> FEATURE:
<223> OTHER INFORMATION: Portion of CDR1 heavy chain sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 56

Xaa Tyr Ala Met Xaa
1               5

<210> SEQ ID NO 57
<211> LENGTH: 5
<212> TYPE: PRT
<213> ORGANISM: Artificial sequence
<220> FEATURE:
<223> OTHER INFORMATION: Portion of CDR1 heavy chain sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 57

Ser Tyr Xaa Met Xaa
1               5

<210> SEQ ID NO 58
```

```
<211> LENGTH: 17
<212> TYPE: PRT
<213> ORGANISM: Artificial sequence
<220> FEATURE:
<223> OTHER INFORMATION: Portion of CDR2 heavy chain sequence
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 58

Ala Ile Ser Xaa Xaa Gly Gly Xaa Thr Xaa Xaa Ala Asp Ser Val Lys
1               5                   10                  15

Gly

<210> SEQ ID NO 59
<211> LENGTH: 17
<212> TYPE: PRT
<213> ORGANISM: Artificial sequence
<220> FEATURE:
<223> OTHER INFORMATION: Portion of CDR2 heavy chain sequence

<400> SEQUENCE: 59

Ala Ile Ser Gly Ser Gly Gly Ser Thr Thr Thr Ala Asp Ser Val Lys
1               5                   10                  15

Gly

<210> SEQ ID NO 60
<211> LENGTH: 13
<212> TYPE: PRT
<213> ORGANISM: Artificial sequence
<220> FEATURE:
<223> OTHER INFORMATION: Portion of CDR3 heavy chain sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 60

Asn Gly Asn Tyr Arg Gly Ser Leu Xaa Ala Phe Asp Ile
1               5                   10

<210> SEQ ID NO 61
<211> LENGTH: 14
<212> TYPE: PRT
<213> ORGANISM: Artificial sequence
<220> FEATURE:
<223> OTHER INFORMATION: Portion of CDR1 light chain sequence

<400> SEQUENCE: 61

Thr Gly Ser Ser Ser Asn Ile Gly Ala Gly Tyr Asp Val His
1               5                   10

<210> SEQ ID NO 62
<211> LENGTH: 7
<212> TYPE: PRT
<213> ORGANISM: Artificial sequence
<220> FEATURE:
<223> OTHER INFORMATION: Portion of CDR2 light chain sequence

<400> SEQUENCE: 62
```

```
Gly Asn Asn Asn Arg Pro Ser
1               5

<210> SEQ ID NO 63
<211> LENGTH: 12
<212> TYPE: PRT
<213> ORGANISM: Artificial sequence
<220> FEATURE:
<223> OTHER INFORMATION: Portion of CDR3 light chain sequence

<400> SEQUENCE: 63

Gln Ser Tyr Asp Ser Ser Leu Ser Ala Trp Val Val
1               5                   10

<210> SEQ ID NO 64
<211> LENGTH: 6
<212> TYPE: PRT
<213> ORGANISM: Artificial sequence
<220> FEATURE:
<223> OTHER INFORMATION: Consensus sequence

<400> SEQUENCE: 64

Glu Glu Asp Leu Pro Glu
1               5

<210> SEQ ID NO 65
<211> LENGTH: 10
<212> TYPE: PRT
<213> ORGANISM: Artificial Sequence
<220> FEATURE:
<223> OTHER INFORMATION: Portion of the CDR3 heavy chain sequence

<400> SEQUENCE: 65

Asn Gly Asn Tyr Arg Gly Ala Phe Asp Ile
1               5                   10

<210> SEQ ID NO 66

<400> SEQUENCE: 66

000

<210> SEQ ID NO 67
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 67

Ala Ile Ser Ala Asn Gly Gly Thr Thr Tyr Tyr Ala Asp Ser Val Lys
1               5                   10                  15

Gly

<210> SEQ ID NO 68
<211> LENGTH: 14
<212> TYPE: PRT
<213> ORGANISM: Artificial Sequence
<220> FEATURE:
<223> OTHER INFORMATION: Synthetic Oligopeptide

<400> SEQUENCE: 68

Thr Gly Ser Ser Ser Asn Ile Gly Ala Gly Phe Asp Val His
1               5                   10
```

```
<210> SEQ ID NO 69
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 69

Gly Asn Thr Asn Arg Pro Ser
1               5

<210> SEQ ID NO 70
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 70

Gln Ser Tyr Asp Ser Arg Leu Ser Ala Trp Val
1               5                   10

<210> SEQ ID NO 71
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 71
tagggcgcgg ccgcaaccga gaccagccag gtggcgcccg ccgggggagg aggcagcccc      60
accacgacgc cagcgccgcg a                                                81

<210> SEQ ID NO 72
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 72

Gly Asn Ser Asn Arg Pro Ser
1               5

<210> SEQ ID NO 73
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 73

Gln Ser Tyr Asp Arg Ser Leu Ser Trp Val
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 74

Gln Ser Tyr Asp Ser Thr Leu Arg Val Trp Met
1               5                   10
```

<210> SEQ ID NO 75
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 75
tagggcgcgg ccgcaaccga gaccagccag gtggcgcccg ccggcggagg aggcagcatt        60
gaagttatgt atcctcctcc t                                                  81

<210> SEQ ID NO 76
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 76

Gln Ser Tyr Asp Lys Ser Leu Thr Trp Val
1               5                   10

<210> SEQ ID NO 77
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 77
ctagccttaa ttaattagcg aggaggggc agggcctgca t                             41

<210> SEQ ID NO 78
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 78

Thr Glu Thr Ser Gln Val Gln Pro Gln
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 79

Gly Gly Gly Gly Ser
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 80

Gln Ser Tyr Asp Lys Ser Leu Ser Trp Val
1               5                   10

<210> SEQ ID NO 81

```
<211> LENGTH: 14
<212> TYPE: PRT
<213> ORGANISM: Artificial Sequence
<220> FEATURE:
<223> OTHER INFORMATION: Synthetic Oligopeptide

<400> SEQUENCE: 81

Thr Gly Ser Ser Ser Asn Ile Gly Ala Gly Phe Asp Val His
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 82

Gln Ser Tyr Asp Ser Ser Leu Ser Ala Trp Val
1               5                   10

<210> SEQ ID NO 83
<211> LENGTH: 735
<212> TYPE: DNA
<213> ORGANISM: Artificial Sequence
<220> FEATURE:
<223> OTHER INFORMATION: Synthetic Polynucleotide

<400> SEQUENCE: 83
caggtgcagc tggtgcagtc tgggggaggc ttggtacagc ctggggggtc cctgagactc      60
tcctgtgcag cctctggatt ccccttttagc agctatgcca tgagctgggt ccgccaggct    120
ccagggaagg ggctggagtg ggtctcagct attagtgcta atggtggtac acatactac      180
gcagactccg tgaagggccg gttcaccatc tccagagaca attccaagaa cacgctgtat    240
ctgcaaatga acagcctgag agccgaggac acggccgtat attactgtgc gaataatggg    300
aactatcgcg gtgcttttga tatctggggc caagggacaa tggtcaccgt ctcttcaggt    360
ggcggcggtt ccggaggtgg tggttctggc ggtggtggca gccagtctgt gctgactcag    420
ccacccctcag tgtctggggc cccagggcag agggtcacca tctcctgcac tgggagcagc    480
tccaacatcg gggcaggtta tgatgtacac tggtaccagc agcttccagg aacagccccc    540
aaactcctca tctatggtaa cagcaatcgg ccctcagggg tccctgaccg attctctggc    600
tccaagtctg gctcctcagc ctccctggcc atcactgggc tccaggctga ggatgaggct    660
cattattact gccagtcata tgacagaagc ctgtcttggg tgttcggcgg agggaccaaa    720
ttgaccgtcc taggt                                                     735

<210> SEQ ID NO 84
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 84

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
                20                  25                  30

Ala Met Ser Trp Val Arg Gln Ala Pro Gly Lys Gly Leu Glu Trp Val
            35                  40                  45
```

Ser Ala Ile Ser Ala Asn Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Asn Gly Asn Tyr Arg Gly Ala Phe Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Ser Gln Ser Val Leu Thr Gln Pro Pro Ser Val
130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Ser Ser Ala Ser
        195                 200                 205

Leu Ala Ile Thr Gly Leu Gln Ala Glu Asp Glu Ala His Tyr Tyr Cys
210                 215                 220

Gln Ser Tyr Asp Arg Ser Leu Ser Trp Val Phe Gly Gly Gly Thr Lys
225                 230                 235                 240

Leu Thr Val Leu Gly
            245

<210> SEQ ID NO 85
<211> LENGTH: 732
<212> TYPE: DNA
<213> ORGANISM: Artificial Sequence
<220> FEATURE:
<223> OTHER INFORMATION: Synthetic Oligonucleotide

<400> SEQUENCE: 85
caggtgcagc tgcaggagtc ggggggaggc ttggtacagc ctgggggtc cctgagactc      60 tcctgtgcag cctctggatt cacctttagc atctatgcca tgagctgggt ccgccaggct    120
ccagggaagg gctggagtg gtctcagct attagtggta gtggtggtgg cacataccac     180
gcagactccg tgaagggccg gttcaccatc tccagagaca attccaagaa cacgctgtat    240
ctgcaaatga acagcctgag agccgaggac acggccgtct attactgtgc gaaattctct    300
gcgtatagtg ctacgatttt gtggggccag ggaaccctgg tcaccgtctc ctcaggtggc    360
ggcggttccg gaggtggtgg ttctggcggt ggtggcagcc agtctgtgct gactcagcca    420
ccctcagtgt ctggggcccc agggcagagg gtcacaatct cctgcactgg gagcagctcc    480
aacatcggga gaggttataa tgtacactgg taccagcagc ttccaggaac agcccccaaa    540
ctcctcatct atgataacac gaatcggccc tcaggggtcc ctgcccgatt ctctggctcc    600
aagtctgcca cgtcagcctc cctgaccatc actgggctcc aggctgacga tgaggctgat    660
tattactgcc agtcgtatga cagcggcctg agtgggtgt tcggcggagg gaccaagctg    720
accctcctag gt                                                        732

<210> SEQ ID NO 86
<211> LENGTH: 244
<212> TYPE: PRT

<213> ORGANISM: Artificial Sequence
<220> FEATURE:
<223> OTHER INFORMATION: Synthetic Polypeptide

<400> SEQUENCE: 86

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser Ala Tyr Ser Gly Tyr Asp Leu Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Gly Ala Pro Gly Gln Arg Val Thr Ile Ser Cys Thr Gly Ser Ser Ser
145                 150                 155                 160

Asn Ile Gly Arg Gly Tyr Asn Val His Trp Tyr Gln Gln Leu Pro Gly
                165                 170                 175

Thr Ala Pro Lys Leu Leu Ile Tyr Asp Asn Thr Asn Arg Pro Ser Gly
            180                 185                 190

Val Pro Ala Arg Phe Ser Gly Ser Lys Ser Ala Thr Ser Ala Ser Leu
        195                 200                 205

Thr Ile Thr Gly Leu Gln Ala Asp Asp Glu Ala Asp Tyr Tyr Cys Gln
    210                 215                 220

Ser Tyr Asp Ser Gly Leu Arg Trp Val Phe Gly Gly Gly Thr Lys Leu
225                 230                 235                 240

Thr Leu Leu Gly

<210> SEQ ID NO 87
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 87
gaggtgcagc tggtgcagtc tgggggaggc ttggtacagc cggggggtc cctgagactc        60 tcctgtgcag cctctggatt cacctttagc agctatgcca tgagctgggt ccgccaggct      120
ccagggaagg ggctggagtg gtctcagct attagtgcta atggtggtac cacatactac      180
gcagactccg tgaagggccg gttcaccatc tccagagaca attccaagaa cacgctgtat      240
ctgcaaatga acagcctgag agccgaggac acggccgtat attactgtgc gaataatggg      300
aactatcgcg gtgcttttga tatctggggc caagggacca cggtcaccgt ctcctcaggt      360
ggcggcggtt ccgaggtgg tggttctggc ggtggtggca gccagtctgt gctgactcag      420
ccaccctcag tgtctggggc cccagggcag agggtcacca tctcctgcac tgggagcagc      480

```
tccaacatcg gggcaggttt tgatgtacac tggtaccagc aacttccagg aacagccccc    540
agactcctca tctatggtaa caacaatcgg ccctcagggg tccctgaccg attctctggc    600
tccaagtctg gcacctcagc ctccctggcc atcactgggc tccaggctga ggatgagact    660
gattatttct gccagtccta tgacagcagc ctgagtgctt gggtattcgg cggagggacc    720
aaggtgaccg tcctacgt                                                  738
```

<210> SEQ ID NO 88
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 88

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Gly Ala Pro Gly Gln Arg Val Thr Ile Ser Cys Thr Gly Ser Ser
145                 150                 155                 160

Ser Asn Ile Gly Ala Gly Phe Asp Val His Trp Tyr Gln Gln Leu Pro
                165                 170                 175

Gly Thr Ala Pro Arg Leu Leu Ile Tyr Gly Asn Asn Asn Arg Pro Ser
            180                 185                 190

Gly Val Pro Asp Arg Phe Ser Gly Ser Lys Ser Gly Thr Ser Ala Ser
        195                 200                 205

Leu Ala Ile Thr Gly Leu Gln Ala Glu Asp Glu Thr Asp Tyr Phe Cys
    210                 215                 220

Gln Ser Tyr Asp Ser Ser Leu Ser Ala Trp Val Phe Gly Gly Gly Thr
225                 230                 235                 240

Lys Val Thr Val Leu Arg
                245
```

<210> SEQ ID NO 89
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 89

```
caggtgcagc tggtgcagtc tggggggaggc ttggtacagc ctggggggtc cctgagactc    60
```

```
tcctgtgcag cctctggatt cccctttagc agctatgcca tgagctgggt ccgccaggct    120
ccagggaagg ggctggagtg ggtctcagct attagtgcta atggtggtac cacatactac    180
gcagactccg tgaagggccg gttcaccatc tccagagaca attccaagaa cacgctgtat    240
ctgcaaatga acagcctgag agccgaggac acggccgtat attactgtgc gaataatggg    300
aactatcgcg gtgcttttga tatctggggc caagggacaa tggtcaccgt ctcttcaggt    360
ggcggcggtt ccgaggtggt ggttctggc ggtggtggca tccagtctgt gctgactcag    420 ccacccctcag tgtctggggc cccagggcag agggtcacca tctcctgcac tgggagcagc    480
tccaacatcg ggcaggtta tgatgtacac tggtaccagc agcttccagg aacagccccc    540
aaactcctca tctatggtaa caccaatcgg ccctcagggg tccctgaccg attctctggc    600
tccaagtctg gcacctcagc ctccctggcc atcattgggc tccaggctga cgatgaggct    660
gattattact gccagtccta tgacagcacc ctgagggtct ggatgttcgg cggagggacc    720
aagctgaccg tccttggt                                                  738
```

<210> SEQ ID NO 90
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 90

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ile Gln Ser Val Leu Thr Gln Pro Pro Ser Val
    130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Gly Asn Thr Asn Arg Pro Ser
            180                 185                 190

Gly Val Pro Asp Arg Phe Ser Gly Ser Lys Ser Gly Thr Ser Ala Ser
        195                 200                 205

Leu Ala Ile Ile Gly Leu Gln Ala Asp Asp Glu Ala Asp Tyr Tyr Cys
    210                 215                 220

Gln Ser Tyr Asp Ser Thr Leu Arg Val Trp Met Phe Gly Gly Gly Thr
225                 230                 235                 240
```

Lys Leu Thr Val Leu Gly
            245

<210> SEQ ID NO 91
<211> LENGTH: 726
<212> TYPE: DNA
<213> ORGANISM: Artificial Sequence
<220> FEATURE:
<223> OTHER INFORMATION: Synthetic Polynucleotide

<400> SEQUENCE: 91

| | | | | | |
|---|---|---|---|---|---|
| gaggtgcagc | tggtggagtc | tgggggaggc | gtggtccagc | ctgggaggtc | cctgagactc | 60 |
| tcctgtgcag | cctctggatt | caccttcagt | agctatggca | tgcactgggt | ccgccaggct | 120 |
| ccagggaagg | gctggagtg | gtctcagct | attagtggta | gtggtggtag | cacatactac | 180 |
| gcagactccg | tgaagggccg | attcaccatc | tccagagaca | acgccaagaa | cacgctgtat | 240 |
| ctgcaaatga | acagtctgag | agccgaggac | acggctgtgt | attactgtgc | aagagccgcg | 300 |
| gtaacaggag | gcttcgaccc | ctggggccag | ggcaccctgg | tcaccgtctc | ctcaggtggc | 360 |
| ggcggttccg | gaggtggtgg | ttctggcggt | ggtggcagcc | agcctgggct | gactcagcca | 420 |
| ccctcggtgt | cagtggcccc | aggacagacg | gccaggatta | cctgtggggg | agacaatatt | 480 |
| ggaagaaaaa | gtgtgcactg | gtaccaacag | aggccaggcc | aggcccctat | tctagtcatc | 540 |
| cgtgatgata | gggatcggcc | ctcagggatc | cctgagcgat | tctctggctc | cagctctgtg | 600 |
| aatacggcca | ccctgatcat | cagcagggtc | gaagccggag | atgaggccga | ctattattgt | 660 |
| caggtgtggg | atagtagtag | taaacattat | gtcttcggac | cagggaccaa | ggtcaccgcc | 720 |
| ctaggt | | | | | 726 |

<210> SEQ ID NO 92
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 92

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Val Thr Gly Gly Phe Asp Pro Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Gln Pro Gly Leu Thr Gln Pro Pro Ser Val Ser
    130                 135                 140

Val Ala Pro Gly Gln Thr Ala Arg Ile Thr Cys Gly Gly Asp Asn Ile
145                 150                 155                 160

-continued

Gly Arg Lys Ser Val His Trp Tyr Gln Gln Arg Pro Gly Gln Ala Pro
            165                 170                 175

Ile Leu Val Ile Arg Asp Asp Arg Pro Ser Gly Ile Pro Glu
            180                 185                 190

Arg Phe Ser Gly Ser Ser Val Asn Thr Ala Thr Leu Ile Ile Ser
        195                 200                 205

Arg Val Glu Ala Gly Asp Glu Ala Asp Tyr Tyr Cys Gln Val Trp Asp
    210                 215                 220

Ser Ser Ser Lys His Tyr Val Phe Gly Pro Gly Thr Lys Val Thr Ala
225                 230                 235                 240

Leu Gly

<210> SEQ ID NO 93
<211> LENGTH: 723
<212> TYPE: DNA
<213> ORGANISM: Artificial Sequence
<220> FEATURE:
<223> OTHER INFORMATION: Synthetic Polynucleotide

<400> SEQUENCE: 93
caggtcacct tgaaggagtc tgggggaggc gtggtccagc ctgggacgtc cctgagactc      60
tcctgtgcag cctctggatt cacctttagc aactatgcca tgacgtgggt ccgccaggct     120
ccagggaagg ggctggagtg ggtgggtcta atatcttatg atggaagtgt acacactac     180 acagactccg tgaagggccg attcaccatc tccagagaca acgccaagaa ctcactgtat     240
ttgcaaatga acaccctgag agccgacgac acggctgtgt attattgtgc gagaggctcc     300
ggctaccaag aacactgggg ccagggaacc ctggtcaccg tctcctcagg tggcggcggt     360
tccggaggtg tggttctggc ggtggtggc agcctgcctg tgctgactca gccaccctcg     420
gtgtcagtgg ccccaggaca gacggccagg attacctgtg ggggaaacaa cattggaagt     480
aaaagtgtgc actggtacca gcagaagcca ggccaggccc ctgtgctggt catctattat     540
gatagcgacc ggccctcagg gatccctgag cgattctctg gctccaactc tgggaacacg     600
gccaccctga ccatcagcag ggtcgaagcc ggggatgagg ccgactatta ctgtcaggtg     660
tgggatagta gtagtgatca tcatgtggta ttcggcggag ggaccaagct gaccgtccta     720
ggt                                                                    723

<210> SEQ ID NO 94
<211> LENGTH: 241
<212> TYPE: PRT
<213> ORGANISM: Artificial Sequence
<220> FEATURE:
<223> OTHER INFORMATION: Synthetic Polypeptide

<400> SEQUENCE: 94

Gln Val Thr Leu Lys Glu Ser Gly Gly Gly Val Val Gln Pro Gly Thr
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Gly Leu Ile Ser Tyr Asp Gly Ser Val His Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Asp Asp Thr Ala Val Tyr Tyr Cys
            85                  90                  95

Ala Arg Gly Ser Gly Tyr Gln Glu His Trp Gly Gln Gly Thr Leu Val
        100                 105                 110

Thr Val Ser Ser Gly Gly Gly Ser Gly Gly Gly Ser Gly Gly
        115                 120                 125

Gly Gly Ser Leu Pro Val Leu Thr Gln Pro Pro Ser Val Ser Val Ala
    130                 135                 140

Pro Gly Gln Thr Ala Arg Ile Thr Cys Gly Gly Asn Asn Ile Gly Ser
145                 150                 155                 160

Lys Ser Val His Trp Tyr Gln Gln Lys Pro Gly Gln Ala Pro Val Leu
                165                 170                 175

Val Ile Tyr Tyr Asp Ser Asp Arg Pro Ser Gly Ile Pro Glu Arg Phe
            180                 185                 190

Ser Gly Ser Asn Ser Gly Asn Thr Ala Thr Leu Thr Ile Ser Arg Val
        195                 200                 205

Glu Ala Gly Asp Glu Ala Asp Tyr Tyr Cys Gln Val Trp Asp Ser Ser
    210                 215                 220

Ser Asp His His Val Val Phe Gly Gly Gly Thr Lys Leu Thr Val Leu
225                 230                 235                 240

Gly

<210> SEQ ID NO 95
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 95
gaggtgcagc tggtgcagtc tgggggaggc gtggtacagc ctggggggtc cctgagactc      60
tcctgtgcag cctctggatt cccctttagc agctatgcca tgagctgggt ccgccaggct     120
ccagggaagg gctggagtg gtctcagct attagtgcta atggtggtac cacatactac       180
gcagactccg tgaagggccg gttcaccatc tccagagaca attccaagaa cacgctgtat     240
ctgcaaatga acagcctgag agccgaggac acggccgtat attactgtgc gaataatggg    300
aactatcgcg gtgcttttga tatctggggc caagggacaa tggtcaccgt ctcttcaggt    360
ggcggcggtt ccggaggtgg tggttctggc ggtggtggca gccagtctgt gctgactcag    420
ccacctcag tgtctggggc ccagggcag agggtcacca tctcctgcac tgggagcagc     480
tccaacatcg gggcaggttt tgatgtacac tggtaccagc agcttccagg aacagccccc    540
aaactcctca tctacggtaa caccaatcga ccctcagggg tccctgaccg attctctggc    600
tccaagtctg gcacctcagc ctccctggcc atcactgggc tccaggctga ggatgagact    660
gattattact gccagtccta tgacagtaga ctgagtgctt gggtgttcgg cggagggacc    720
aagctgaccg tcctaggt                                                   738

<210> SEQ ID NO 96
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 96

Glu Val Gln Leu Val Gln Ser Gly Gly Gly Val Val Gln Pro Gly Gly

```
                1               5                  10                 15
              Ser Leu Arg Leu Ser Cys Ala Ala Ser Gly Phe Pro Phe Ser Tyr
                             20                 25                 30
              Ala Met Ser Trp Val Arg Gln Ala Pro Gly Lys Gly Leu Glu Trp Val
                             35                 40                 45
              Ser Ala Ile Ser Ala Asn Gly Gly Thr Thr Tyr Tyr Ala Asp Ser Val
                             50                 55                 60
              Lys Gly Arg Phe Thr Ile Ser Arg Asp Asn Ser Lys Asn Thr Leu Tyr
               65                 70                 75                 80
              Leu Gln Met Asn Ser Leu Arg Ala Glu Asp Thr Ala Val Tyr Tyr Cys
                             85                 90                 95
              Ala Asn Asn Gly Asn Tyr Arg Gly Ala Phe Asp Ile Trp Gly Gln Gly
                            100                105                110
              Thr Met Val Thr Val Ser Ser Gly Gly Gly Ser Gly Gly Gly
                            115                120                125
              Ser Gly Gly Gly Gly Ser Gln Ser Val Leu Thr Gln Pro Pro Ser Val
                            130                135                140
              Ser Gly Ala Pro Gly Gln Arg Val Thr Ile Ser Cys Thr Gly Ser Ser
              145                150                155                160
              Ser Asn Ile Gly Ala Gly Phe Asp Val His Trp Tyr Gln Gln Leu Pro
                            165                170                175
              Gly Thr Ala Pro Lys Leu Leu Ile Tyr Gly Asn Thr Asn Arg Pro Ser
                            180                185                190
              Gly Val Pro Asp Arg Phe Ser Gly Ser Lys Ser Gly Thr Ser Ala Ser
                            195                200                205
              Leu Ala Ile Thr Gly Leu Gln Ala Glu Asp Glu Thr Asp Tyr Tyr Cys
                            210                215                220
              Gln Ser Tyr Asp Ser Arg Leu Ser Ala Trp Val Phe Gly Gly Gly Thr
              225                230                235                240
              Lys Leu Thr Val Leu Gly
                            245
```

<210> SEQ ID NO 97
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 97

```
caggtgcagc tggtgcagtc tggggagagc gtggtacagc ctgggggtc cctgagactc        60
tcctgtgcag cctctggatt cccctttagc agctatgcca tgagctgggt ccgccaggct      120
ccagggaagg gctggagtg gtctcagct attagtgcta atggtggtac cacatactac        180
gcagactccg tgaagggccg gttcaccatc tccagagaca attccaagaa cacgctgtat      240
ctgcaaatga acagcctgag agccgaggac acggccgtat attactgtgc gaataatggg      300
aactatcgcg gtgcttttga tatctggggc caagggacaa tggtcaccgt ctcttcaggt      360
ggcggcggtt ccggaggtgg tggttctggc ggtggtggca gccagtctgt gctgactcag      420
ccaccctcag tgtctggggc cccagggcag agggtcacca tctcctgcac tgggagcagc      480
tccaacatcg ggcaggtta tgatgttcac tggtaccagc acttccagg aacagccccc       540
aaactcctca tctatggtaa tagcaatcga ccctcaggag tccctgaccg attctctggc      600
tccaagtctg gcacctcagc ctccctggcc atcactgggc tccaggctga ggatgagact      660
```

```
gattatttct gccagtccta tgacagcagc ctgagtgctt gggtattcgg cggagggacc    720
aaggtgaccg tcctaggt                                                  738
```

<210> SEQ ID NO 98
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 98

```
Gln Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln His Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Thr Gly Leu Gln Ala Glu Asp Glu Thr Asp Tyr Phe Cys
    210                 215                 220

Gln Ser Tyr Asp Ser Ser Leu Ser Ala Trp Val Phe Gly Gly Gly Thr
225                 230                 235                 240

Lys Val Thr Val Leu Gly
                245
```

<210> SEQ ID NO 99
<211> LENGTH: 735
<212> TYPE: DNA
<213> ORGANISM: Artificial Sequence
<220> FEATURE:
<223> OTHER INFORMATION: Synthetic Polynucleotide

<400> SEQUENCE: 99

```
caggtgcagc tgcaggagtc gggggggaggc ttggtacagc ctggggggtc cctgagactc     60
tcctgtgcag cctctggatt cacctttagc agctatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
```

```
ctgcaaatga acagcctgag agccgaggac acggccgtat attactgtgc gaaaattgga 300
cggtatagca gcagcttggg gtactggggc cagggcaccc tggtcaccgt ctcctcaggt 360
ggcggcggtt ccggaggtgg tggttctggc ggtggtggca gccagtctgt gctgactcag 420
ccaccctcag tgtctggggc cccagggcag agggtcacaa tctcctgcac tgggagcagc 480
```

```

tccaacatcg ggagaggtta taatgtacac tggtaccagc agcttccagg aacagccccc 540
aaactcctca tctatgataa cacgaatcgg ccctcagggg tccctgcccg attctctggc 600
tccaagtctg ccacgtcagc ctccctggcc atcactgggc tccaggctga cgatgaggct 660
gattattact gccagtcgta tgacagcggc ctgagatggg tgttcggcgg ggggaccaag 720
ctgaccctcc tacgt 735
```

<210> SEQ ID NO 100
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 100

```
Gln Val Gln Leu Gln Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ile Gly Arg Tyr Ser Ser Ser Leu Gly Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Ser Val Leu Thr Gln Pro Pro Ser Val
130 135 140

Ser Gly Ala Pro Gly Gln Arg Val Thr Ile Ser Cys Thr Gly Ser Ser
145 150 155 160

Ser Asn Ile Gly Arg Gly Tyr Asn Val His Trp Tyr Gln Gln Leu Pro
165 170 175

Gly Thr Ala Pro Lys Leu Leu Ile Tyr Asp Asn Thr Asn Arg Pro Ser
180 185 190

Gly Val Pro Ala Arg Phe Ser Gly Ser Lys Ser Ala Thr Ser Ala Ser
195 200 205

Leu Ala Ile Thr Gly Leu Gln Ala Asp Asp Glu Ala Asp Tyr Tyr Cys
210 215 220

Gln Ser Tyr Asp Ser Gly Leu Arg Trp Val Phe Gly Gly Gly Thr Lys
225 230 235 240

Leu Thr Leu Leu Arg
245
```

<210> SEQ ID NO 101

<211> LENGTH: 735
<212> TYPE: DNA
<213> ORGANISM: Artificial Sequence
<220> FEATURE:
<223> OTHER INFORMATION: Synthetic Polynucleotide

<400> SEQUENCE: 101

```
caggtgcagc tggtgcagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gacgtacggt     300
gactacggca gcctcgacta ctggggccag ggcaccctgg tcaccgtctc ctcaggtggc     360
ggcggttccg gaggtggtgg ttctcgcggt ggtggcagcc agtctgtgct gactcagcca     420
ccctcagtgt ctggggcccc agggcagagg gtcaccatct cctgcactgg gagcagctcc     480
aacatcgggg caggttatga tgtacactgg taccagcagc ttccaggaac agcccccaaa     540
ctcctcatct atgctaacaa caatcggccc tcaggggtcc ctgaccgatt ctctggctcc     600
aagtctggca cctcagcctc cctggccatc actgggctcc aggctgagga tgaggctgat     660
tattactgcc agtcctatga cagcagcctg agggcttggg tgttcggcgg agggaccaag     720
ctggccgtcc tgggt                                                       735
```

<210> SEQ ID NO 102
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 102

```
Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Tyr Gly Asp Tyr Gly Ser Leu Asp Tyr Trp Gly Gln Gly Thr
            100                 105                 110

Leu Val Thr Val Ser Ser Gly Gly Gly Ser Gly Gly Gly Gly Ser
        115                 120                 125

Arg Gly Gly Gly Ser Gln Ser Val Leu Thr Gln Pro Pro Ser Val Ser
    130                 135                 140

Gly Ala Pro Gly Gln Arg Val Thr Ile Ser Cys Thr Gly Ser Ser Ser
145                 150                 155                 160

Asn Ile Gly Ala Gly Tyr Asp Val His Trp Tyr Gln Gln Leu Pro Gly
                165                 170                 175

Thr Ala Pro Lys Leu Leu Ile Tyr Ala Asn Asn Asn Arg Pro Ser Gly
            180                 185                 190
```

Val Pro Asp Arg Phe Ser Gly Ser Lys Ser Gly Thr Ser Ala Ser Leu
            195                 200                 205

Ala Ile Thr Gly Leu Gln Ala Glu Asp Glu Ala Asp Tyr Tyr Cys Gln
            210                 215                 220

Ser Tyr Asp Ser Ser Leu Arg Ala Trp Val Phe Gly Gly Gly Thr Lys
225                 230                 235                 240

Leu Ala Val Leu Gly
            245

<210> SEQ ID NO 103
<211> LENGTH: 735
<212> TYPE: DNA
<213> ORGANISM: Artificial Sequence
<220> FEATURE:
<223> OTHER INFORMATION: Synthetic Polynucleotide

<400> SEQUENCE: 103

| | | | | | |
|---|---|---|---|---|---|
| caggtgcagc | tggtgcagtc | tggggggaggc | ttggtacagc | ctgggggtc | cctgagactc | 60 |
| tcctgtgcag | cctctggatt | cccctttagc | agctatgcca | tgagctgggt | ccgccaggct | 120 |
| ccagggaagg | ggctggagtg | ggtctcagct | attagtgcta | atggtggtac | cacatactac | 180 |
| gcagactccg | tgaagggccg | gttcaccatc | tccagagaca | attccaagaa | cacgctgtat | 240 |
| ctgcaaatga | acagcctgag | agccgaggac | acggccgtat | attactgtgc | gaataatggg | 300 |
| aactatcgcg | gtgcttttga | tatctggggc | caagggacaa | tggtcaccgt | ctcttcaggt | 360 |
| ggcggcggtt | ccggaggtgg | tggttctggc | ggtggtggca | gccagtctgt | gctgactcag | 420 |
| ccacccctcag | tgtctggggc | cccagggcag | aggatcacca | tctcctgcac | tgggaccagc | 480 |
| tccaacatcg | gggcaggtta | tgatgtacac | tggtaccagc | aacttccagg | agcagccccc | 540 |
| agagtcctca | tctatggtaa | caacaatcgg | ccctcagggg | tccctgaccg | attctctggc | 600 |
| tccaagtctg | gcacctcagc | ctccctggcc | atcactgggc | tccagtctga | ggatgaggct | 660 |
| gattattact | gtcagtccta | tgacaagagt | ctgagttggg | tgttcggcgg | agggaccaag | 720 |
| ctgaccgtcc | tacgt | | | | | 735 |

<210> SEQ ID NO 104
<211> LENGTH: 245
<212> TYPE: PRT
<213> ORGANISM: Artificial Sequence
<220> FEATURE:
<223> OTHER INFORMATION: Synthetic Polynucleotide

<400> SEQUENCE: 104

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Asn Asn Gly Asn Tyr Arg Gly Ala Phe Asp Ile Trp Gly Gln Gly
            100                 105                 110

```
Thr Met Val Thr Val Ser Ser Gly Gly Gly Ser Gly Gly Gly
            115                 120                 125

Ser Gly Gly Gly Ser Gln Ser Val Leu Thr Gln Pro Pro Ser Val
        130                 135                 140

Ser Gly Ala Pro Gly Gln Arg Ile Thr Ile Ser Cys Thr Gly Thr Ser
145                 150                 155                 160

Ser Asn Ile Gly Ala Gly Tyr Asp Val His Trp Tyr Gln Gln Leu Pro
                165                 170                 175

Gly Ala Ala Pro Arg Val Leu Ile Tyr Gly Asn Asn Asn Arg Pro Ser
                180                 185                 190

Gly Val Pro Asp Arg Phe Ser Gly Ser Lys Ser Gly Thr Ser Ala Ser
                195                 200                 205

Leu Ala Ile Thr Gly Leu Gln Ser Glu Asp Glu Ala Asp Tyr Tyr Cys
                210                 215                 220

Gln Ser Tyr Asp Lys Ser Leu Ser Trp Val Phe Gly Gly Gly Thr Lys
225                 230                 235                 240

Leu Thr Val Leu Arg
                245

<210> SEQ ID NO 105
<211> LENGTH: 747
<212> TYPE: DNA
<213> ORGANISM: Artificial Sequence
<220> FEATURE:
<223> OTHER INFORMATION: Synthetic Polynucleotide

<400> SEQUENCE: 105
caggtgcagc tggtgcagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtgttag cacatactac     180
gcagactccg tgaagggccg cttcaccatc tccagagaca attccaagaa cacgctgtat     240
ttgcaaatga acagcctgag agccgaggac acggccgtat attactgtgc gaaatattgt     300
agtagtacca gctgctatcg cggtatggac gtctggggca aaggcacccct ggtcaccgtc     360
tcctcaggtg gcggcggttc cggaggtggt ggttctcgcg gtggtggcag ccagtctgtg     420
ctgactcagc accctcagt gtctggggcc cagggcaga gggtcaccat ctcctgcact     480
gggagcagct ccaacatcgg ggcaggttat gatgtacact ggtaccagca gcttccagga     540
acagccccca aactcctcat ctatgctaac aacaatcggc cctcaggggt ccctgaccga     600
ttctctggct ccaagtctgg cacctcagcc tccctggcca tcactgggct ccaggctgag     660
gatgaggctg attattactg ccagtcctat gacagcagcc tgagggcttg gtgttcggc     720
ggagggacca agctggccgt cctgggt                                        747

<210> SEQ ID NO 106
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 106

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Ala Ile Ser Gly Ser Gly Val Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Cys Ser Ser Thr Ser Cys Tyr Arg Gly Met Asp Val Trp
            100                 105                 110

Gly Lys Gly Thr Leu Val Thr Val Ser Ser Gly Gly Gly Ser Gly
            115                 120                 125

Gly Gly Ser Arg Gly Gly Gly Ser Gln Ser Val Leu Thr Gln Pro
            130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Asp Val His Trp Tyr Gln
                165                 170                 175

Gln Leu Pro Gly Thr Ala Pro Lys Leu Leu Ile Tyr Ala Asn Asn Asn
            180                 185                 190

Arg Pro Ser Gly Val Pro Asp Arg Phe Ser Gly Ser Lys Ser Gly Thr
            195                 200                 205

Ser Ala Ser Leu Ala Ile Thr Gly Leu Gln Ala Glu Asp Glu Ala Asp
            210                 215                 220

Tyr Tyr Cys Gln Ser Tyr Asp Ser Ser Leu Arg Ala Trp Val Phe Gly
225                 230                 235                 240

Gly Gly Thr Lys Leu Ala Val Leu Gly
            245

<210> SEQ ID NO 107
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 107
caggtgcagc tggtgcagtc tggggaggc ttggtacagc ctgggggtc cctgagactc     60 tcctgtgcag cctctgaatt caccttggt acctatgcca tgacctgggt ccgccaggct    120
ccagggaagg gctggagtg gtctcggct gttagtggta gtggtggtag cacatactac    180
gcagactccg tgaagggccg gttcaccatc tccagagaca attccaggaa cacgctgtat    240
ctgcaaatga acagcctgag agccgatgac acggccgtgt attactgtgc aagaggcccg    300
gtattacgat atggctttga tatctggggc caagggacaa tggtcaccgt ctcttcaggt    360
ggcggcggtt ccggaggtgg tggttctggc ggtggtggca gccagtctgt gctgactcag    420
ccaccctcag tctctggggc cccagggcag aggatcacca tctcctgcac tgggagcagg    480
tccaacatcg gggcagatta tgatgtacac tggtaccagc agcttccagg aacagccccc    540
aaactcctca tctatgctaa caacaatcgg ccctcagggg tcctggtcg attctctgcc    600 tccaagtctg gcacctcagc tccctggcc atcagtgggc tccaggctga ggatgaggct    660
gattattact gccagtcgta tgacagcagc ctgagggctt gggtgttcgg cggagggacc    720
aagctggccg tcctgggt                                                  738

<210> SEQ ID NO 108
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 108

```
Gln Val Gln Leu Val Gln Ser Gly Gly Gly Leu Val Gln Pro Gly Gly
 1               5                  10                  15

Ser Leu Arg Leu Ser Cys Ala Ala Ser Glu Phe Thr Phe Gly Thr Tyr
            20                  25                  30

Ala Met Thr Trp Val Arg Gln Ala Pro Gly Lys Gly Leu Glu Trp Val
        35                  40                  45

Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Pro Val Leu Arg Tyr Gly Phe Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Gly Ala Pro Gly Gln Arg Ile Thr Ile Ser Cys Thr Gly Ser Arg
145                 150                 155                 160

Ser Asn Ile Gly Ala Asp Tyr Asp Val His Trp Tyr Gln Gln Leu Pro
                165                 170                 175

Gly Thr Ala Pro Lys Leu Leu Ile Tyr Ala Asn Asn Asn Arg Pro Ser
            180                 185                 190

Gly Val Pro Gly Arg Phe Ser Ala Ser Lys Ser Gly Thr Ser Ala Ser
        195                 200                 205

Leu Ala Ile Ser Gly Leu Gln Ala Glu Asp Glu Ala Asp Tyr Tyr Cys
    210                 215                 220

Gln Ser Tyr Asp Ser Ser Leu Arg Ala Trp Val Phe Gly Gly Gly Thr
225                 230                 235                 240

Lys Leu Ala Val Leu Gly
                245
```

<210> SEQ ID NO 109
<211> LENGTH: 735
<212> TYPE: DNA
<213> ORGANISM: Artificial Sequence
<220> FEATURE:
<223> OTHER INFORMATION: Synthetic Polynucleotide

<400> SEQUENCE: 109

```
caggtgcagc tgcaggagtc ggggggaggc ttggtccagc ctgggggtc cctgagactc      60 tcctgtgcag cctctggatt caccttagc agctatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtat attactgtgc gaggtcccat    300
agcagtggag gatttgacta ctggggccag ggaaccctgg tcaccgtctc ctcaggtggc    360
```

```
ggcggttccg gaggtggtgg ttctggcggt ggtggcagcc agtctgtgct gactcagcca    420
ccctcagtgt ctggggcccc agggcagagg gtcacaatct cctgcactgg gagcagctcc    480
aacatcggga gaggttataa tgtacactgg taccagcagc ttccaggaac agcccccaaa    540
ctcctcatct atggtaacac caatcggccc tcagggtcc ctgaccgatt ctctggctcc    600
aagtctggca cctcagcctc cctggccatc actgggctcc aggctgagga tgagggtgat    660
tattactgcc agtcctatga cagcagcctg agtgcttggg tgttcggcgg ggggaccaag    720
ctgaccgtcc taggt                                                     735
```

<210> SEQ ID NO 110
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 110

```
Gln Val Gln Leu Gln Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser His Ser Gly Gly Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Gly Ala Pro Gly Gln Arg Val Thr Ile Ser Cys Thr Gly Ser Ser Ser
145                 150                 155                 160

Asn Ile Gly Arg Gly Tyr Asn Val His Trp Tyr Gln Gln Leu Pro Gly
                165                 170                 175

Thr Ala Pro Lys Leu Leu Ile Tyr Gly Asn Thr Asn Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Ala Glu Asp Glu Gly Asp Tyr Tyr Cys Gln
    210                 215                 220

Ser Tyr Asp Ser Ser Leu Ser Ala Trp Val Phe Gly Gly Gly Thr Lys
225                 230                 235                 240

Leu Thr Val Leu Gly
                245
```

METHOD OF TREATING A TUMOR EXPRESSING CARBONIC ANHYDRASE IX (G250) BY ADMINISTERING A G250-SPECIFIC CHIMERIC ANTIGEN RECEPTOR

RELATED APPLICATIONS

This application is a division of U.S. patent application Ser. No. 15/537,780, now U.S. Pat. No. 10,870,705, which is a national stage entry of International Application No. PCT/US2015/067178, which claims priority to, and the benefit of U.S. Provisional Application No. 62/094,596, filed on Dec. 19, 2014, the contents of which are hereby incorporated by reference in their entireties.

GOVERNMENT INTEREST

This invention was made with government support under grant number DK072282 awarded by the National Institutes of Health. The government has certain rights in the invention.

INCORPORATION-BY-REFERENCE OF SEQUENCE LISTING

The contents of the text file named, "5031461-33-US2.txt", which is 109,718 bytes in size and was created on Nov. 13, 2017, are hereby incorporated by reference in their entirety.

FIELD OF THE INVENTION

The present invention relates generally to chimeric antigen receptor cells specific for carbonic anhydrase IX (CAIX) and methods of using same for treatment of CAIX expressing cancers such as renal cell carcinoma.

BACKGROUND OF THE INVENTION

The Carbonic anhydrases are a family of zinc metalloenzymes which catalyze reversible hydration of carbon dioxide in order to maintain pH balance in living organisms. Carbonic anhydrase IX (CAIX) is a transmembrane glycoprotein with molecular weight of 54/58 kDa. Structurally, CAIX consists of four domains: an N-terminal proteoglycan-like domain (PG) (aa 53-111), a CA catalytic domain (CA) (aa 135-391), a transmembrane helical segment (aa 415-434), and a short intracytoplasmic tail (aa 434-459). In hypoxic conditions, the CAIX gene is directly activated at the transcriptional level by hypoxia inducible transcription factor HIF-1a, leading to transport of protons to the extracellular medium and lowering of pH Thus, CAIX expression can be regarded as a surrogate marker for hypoxia in various tumors. The resulting acidification of the tumor microenvironment by CA activity and the keratin sulfate unit in the O-linked glycan structure in the PG domain of CAIX are presumed to play an important role in the processes of cell adhesion and tumor progression CAIX is considered a tumor-associated antigen and its overexpression is found among several solid tumor types, particularly in clear cell type renal cell carcinomas (RCC) as well as carcinomas of several histologic types including ovarian, breast, esophageal, bladder, colon, non-small cell lung, dysplasia of the cervix and others. CAIX expression has been suggested to serve as a marker for cancer diagnosis and early detection of carcinogenesis; it is also a prognostic marker for favorable response in IL-2 treated patients of melanoma and kidney cancer, leading to high response rates and low toxicity. Immunostaining and Western blot studies have shown that a high level of CAIX expression is restricted to the majority of primary RCC (clear cell type with granular or spindle cell, papillary type of chromophilic cell and collecting duct except for chromphobic cell), cystic RCCs, and metastatic RCCs but is not observed in normal kidney tissues, benign epithelial cystic lesions, or non-renal cell clear cell adenocarcinoma.

RCC is one of two immunogenic tumor types, besides melanoma, that exhibits evidence of spontaneous regression of metastatic lesions after nephrectomy and of being responsive to immunomodulating therapies such as cancer vaccines and IL-2. Adoptive T cell therapy for metastatic melanoma and RCC patients using ex vivo expanded tumor-infiltrating lymphocytes (TIL) has shown some success. Recently, TCR-modified T cells (TCR α and β chains) were also used to provide an effective tumor targeting T-cell repertoire. However, post-targeting anti-tumor activity can be hampered by deficiencies that involve downregulation at all levels of the MHC class I-restricted antigen presentation machinery, induced allergy due to the loss of expression of costimulatory molecules on the tumor as well as shedding of molecules and secretion of cytokines with immunosuppressive activity by tumors.

SUMMARY OF THE INVENTION

In various aspects the invention provides A chimeric antigen receptor (CAR) having an intracellular signaling domain, a transmembrane domain and an extracellular domain comprising a carbonic anhydrase IX (G250)-specific receptor. In some aspects the CAR further includes a stalk region positioned between the extracellular domain and the transmembrane domain. The transmembrane domain is for example CD28. In other aspects the CAR further includes one or more addition costimulatoty molecules positioned between the transmembrane domain and the intracellular signaling domain. The costimulatory molecules is for example, CD28, 4-IBB, ICOS, or OX40. The intracellular signaling domain includes a CD3 zeta chain.

The carbonic anhydrase IX (G250)-specific receptor is an antibody such as a Fab or scFV. Preferably, the antibody has heavy chain having a CDR1 comprising an amino acid sequence SYAMS (SEQ ID NO: 55); a CDR2 comprising an amino acid sequence AISANGGTTYYADSVKG (SEQ ID NO: 67); and a CDR3 comprising an amino acid sequence NGNYRGAFDI (SEQ ID NO: 65); and a light chain with a CDR1 comprising an amino sequence TGSSSNIGAGFDVH (SEQ ID NO: 68); a CDR2 comprising an amino sequence GNTNRPS (SEQ ID NO: 69); and a CDR3 comprising an amino sequence QSYDSRLSAWV (SEQ ID NO: 70); a light chain with a CDR1 comprising an amino sequence TGSSSNIGAGYDVH (SEQ ID NO: 61); a CDR2 comprising an amino sequence GNSNRPS (SEQ ID NO: 72); and a CDR3 comprising an amino sequence QSYDRSLSWV (SEQ ID NO: 73); a light chain with a CDR1 comprising an amino sequence TGSSSNIGAGYDVH (SEQ ID NO: 61); a CDR2 comprising an amino sequence GNTNRPS (SEQ ID NO: 69); and a CDR3 comprising an amino sequence QSYDSTLRVWM (SEQ ID NO: 74); a light chain with a CDR1 comprising an amino sequence TGSSSNIGAGYDVH (SEQ ID NO: 61); a CDR2 comprising an amino sequence GNNNRPS (SEQ ID NO: 62); and a CDR3 comprising an amino sequence QSYDKSLTWV (SEQ ID NO: 76); a light chain with a CDR1 comprising an amino sequence TGTSSNIGAGYDVH (SEQ ID NO: 79); a CDR2 comprising an amino sequence GNNNRPS (SEQ ID NO: 62); and a CDR3 comprising an amino sequence QSYDKSLSWV (SEQ ID NO: 80); a light chain with a CDR1 comprising an amino sequence TGSSSNIGAGFDVH (SEQ ID NO: 81); a CDR2 comprising an amino sequence GNNNRPS (SEQ ID NO: 62); and a CDR3 comprising an amino sequence QSYDSSLSAWV (SEQ ID NO: 82); or a light chain with a CDR1 comprising an amino sequence TGSSSNIGAGYDVH (SEQ ID NO: 61); a CDR2 comprising an amino sequence GNSNRPS (SEQ ID NO: 72); and a CDR3 comprising an amino sequence QSYDSSLSAWV (SEQ ID NO: 82).

In another aspect the scFv antibody has a heavy chain comprising an amino acid sequence selected from the amino acid sequences of SEQ ID NOs 1, 3-23, and wherein said scFv antibody has a light chain comprising an amino acid sequence selected from the amino acid sequences of SEQ ID NOs: 2 and 24-44.

Further provided by the invention is a genetically engineered cell which express and bear on the cell surface membrane the chimeric antigen receptor according to the invention. The cell is a T-cell or an NK cell. The T cell is CD4+ or CD8+. In other aspects the cell is a mixed population of CD4+ and CDS cells+.

In yet a further aspect the invention provides methods of treating a subject having a carbonic anhydrase IX (G250) expressing tumor by administering the subject the genetically engineered cell according to the invention. The genetically engineered cells are derived from cells that are autologous to the subject. The tumor is a renal cancer, ovarian cancer, breast cancer, esophageal cancer, bladder cancer, colon cancer, or non-small cell lung cancer. The renal cancer is for example renal clear cell cancer. In some aspects the methods further include administering IL-2, an anti-PD-1, an anti-PDL-1 or an anti-CTL4 antibody.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 1A, CAIX+ sk-rc-09 cells, FIG. 1B, CAIX+ sk-rc-52 cells; FIG. 1C, CAIX− sk-rc-59 cells.

FIG. 2A. Construction: The 1st generation CAR scFv-CD8-TCR ζ (CD8 CAR), is composed of a specific anti-CAIX scFv that is coupled to truncated human CD8α extracellular domain, hinge (H), transmembrane (TM) and intracellular regions, then to the signaling domain of human TCRζ. The $2^{nd}$ generation CAR, scFv-CD28-TCRζ (CD28 CAR), contains anti-CAIX scFv fused with human CD28 extracellular, TM and intracellular signaling domain to TCRζ. Both anti-CAIX CARs were cloned into a bicistronic self-inactivating (SIN) lentiviral vector with expression driven by an internal eF1-α promoter. The CAR control construct contains an irrelevant anti-HIV CCR5 specific A8 scFv substitution. FIG. 2B. FACS analysis; Reporter gene ZsGreen was used to quantitate primary T cell transduction efficiency by the lentiviral CAR constructs. In addition, anti-CAIX scFv CARs were stained with CAIX-Fc fusion protein and C9-tag (TETSQVAPA) was stained with 1D4 antibody. Untransduced activated T-cells, LAK only were served as unstained cell control (i) or stained with 2nd antibody (ii. PE-anti-human IgG and iii. APC-anti-mouse IgG) were used as staining controls. FIG. 2C. Western blot: Molecular sizes of monomer/dimer structures of anti-CAIX (clone G36) CD28 and annti-CCR5 (clone A8) CD28 CARs, as well as endogenous TCRζ chain of untransduced T cells were indicated.

FIG. 3A-3C. Effector functions of CAIX-specific CARTs. FIG. 3A. Cytokine secretion. Anti-CAIX CART, irrelevant CART or activated control T cells (LAK) were cocultivated overnight with kidney cancer cell lines sk-rc-52 (CAIX+) and sk-rc-59 (CAIX−) for cytokine production. One representative out of 2-3 results is shown. FIG. 3B. ELISPOT. G36 CART or control A8 CART cells were added to tumor cells overnight. IFN-γ or granzyme B secreting T cells detected by ELISPOT. Similar results were obtained in 2-3 experiments. FIG. 3C. Specific anti-tumor cytotoxicity of CAIX-specific CART cells, control A8 CART cells or LAK cells were incubated in a 4-hour cytotoxicity assay at different amounts of target tumor cell at the ratios as indicated. One out of two experiments is shown. Clone 4-1 is a in vivo passaged subclone of sk-rc-52.

FIG. 4A-4C. Clonal expansion of CART cells after tumor contact. FIG. 4A. Proliferation. CAR-transduced T cells or untransduced T cells (LAK) were plated with irradiated tumor cells (CAIX+ sk-rc-52 & CAIX− sk-rc-59) weekly at three different ratios of tumor to T cells as indicated. Number of T cells was counted every 3-4 days in triplicate from two separate wells. Similar results were obtained in two experiments. FIG. 4B. Clonal enrichment. In tumor stimulation experiments, cultures from CART-and LAK cells were assayed on one week and two weeks by flow cytometry for expression of CART and T-cell subset. One representative of two results is shown.

FIG. 6A-6C. In vivo anti-tumor activity of CAR+ T-cells. FIG. 6A. Expression of ZsGreen by CART cells is shown in upper panel. CART cells were pre-stained with Far Red dye, cytospun and examined by fluorescent microscopy (lower panel). FIG. 6B. In situ staining of G36 CD28 CART cells in regressing tumor. CART-cells were i.v. injected into RCC established mice and tumor tissue was collected on day 1-3. Confocal microscopy was used to measure apoptosis of tumor cells by TUNNEL assay with PE-Cy5 dye (shown as red). Transduced T cells were shown by ZsGreen. Nuclei were counterstained with DPAI. Two representative slides were shown to indicate the apoptosis of tumor cells at the edge of tumor (upper panel) and inside the tumor bed (middle panel), respectively. The magnified image (lower panel) demonstrates CART cells interacted with multiple tumors while a few surrounding tumor cells were dying. FIG. 6C. Granzyme B+ T cells and tumor necrosis. After the treatment with CART cells, the regressing CAIX+ sk-rc-52 tumors were stained by granzyme B antibody (brown) and H&E. The higher magnification view (middle and lower panels of sections a and b in upper panel) shows the locations of granzyme B+ cells (shown by arrows) and the corresponding H&E slide shows the tumor necrosis (shown by n). Granzyme B+ T cells are distributed at the edge of tumor (middle panel) and inside the tumor (lower panel).

DETAILED DESCRIPTION OF THE INVENTION

Figure 1A:
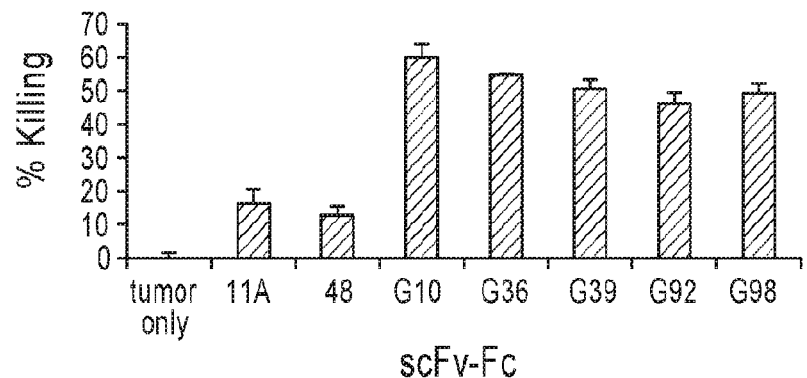
FIG. 1A-1C. ADCC of CAIX-specific Abs. 1 µg/ml CAIX-specific scFv-Fc minibodies were added to the target tumor cells in the presence of human PBMC. (E:T 25:1). Similar results were obtained in 2 experiments. Irrelevant anti-SARS scFv-Fc (11A) and anti-CCR4 scFv-Fc (48) minibodies were used as negative controls.

The present invention relates to a chimeric antigen receptor (CAR) particularly adapted to immune cells used in immunotherapy. In particular, the invention provides carbonic anhydrase IX (CAIX) specific CARs.

More specifically, the present invention is based on the surprising discovery that CAIX(G36)-CD28z CART cells possess superior anti-tumor responses as evidenced by the combined effect of stranger cytotoxic potency, increased cytokine secretion, enhanced proliferation and clonal expansion in vitro, and improved suppression of tumors in vivo with IL-2 provision compared to CAIX(G36)-CD8-TCRs CART cells.

Genetic engineering of human lymphocytes to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived. In certain embodiments of the invention there are lymphocytes that are modified to comprise at least a CAR, and in particular embodiments of the invention a single CAR targets two or more antigens.

In particular cases, the lymphocytes include a receptor that is chimeric, nonnatural and engineered at least in part by the hand of man. In particular cases, the engineered chimeric antigen receptor (CAR) has one, two, three, four, or more components, and in some embodiments the one or more components facilitate targeting or binding of the lymphocyte to one or more tumor antigen-comprising cancer cells.

The CAR according to the invention generally comprises at least one transmembrane polypeptide comprising at least one extracellular ligand-biding domain and; one transmembrane polypeptide comprising at least one intracellular signaling domain; such that the polypeptides assemble together to form a Chimeric Antigen Receptor.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. In particular, the extracellular ligand-binding domain can comprise an antigen binding domain derived from an antibody against an antigen of the target.

In particular cases the CAR is specific for carbonic anhydrase IX (G250), and in certain embodiments, the present invention provides chimeric cells specific for carbonic anhydrase IX (CAIX) by joining an extracellular antigen-binding domain derived from the CAIX-specific antibody to intracellular signaling domains derived from the T-cell receptor zeta-chain, with the endodomains of costimulatory molecules such as CD28. This CAR is expressed in human cells, such as T cells, NK cells, or NKT cells, and the targeting of CAIX positive cancers is encompassed in the invention.

Preferably the antibody has heavy chain with a CDR1 comprising an amino acid sequence SYAMS (SEQ ID NO: 55); a CDR2 comprising an amino acid sequence AISANGGTTYYADSVKG (SEQ ID NO: 67); and a CDR3 comprising an amino acid sequence NGNYRGAFDI (SEQ ID NO: 65); and a light chain with a CDR1 comprising an amino sequence TGSSSNIGAGIFDVH(SEQ ID NO: 68); a CDR2 comprising an amino sequence GNTNRPS (SEQ ID NO: 69); and a CDR3 comprising an amino sequence QSYDSRLSAWV (SEQ ID NO: 70); or a light chain with a CDR1 comprising an amino sequence TGSSSNIGAGYDVH (SEQ ID NO: 61); a CDR2 comprising an amino sequence GNSNRPS (SEQ ID NO: 72); and a CDR3 comprising an amino sequence QSYDRSLSWV (SEQ ID NO. 73); or a light chain with a CDR1 comprising an amino sequence TGSSSNIGAGYDVH (SEQ ID NO: 61); a CDR2 comprising an amino sequence GNTNRPS (SEQ ID NO: 69); and a CDR3 comprising an amino sequence QSYDSTLRVWM (SEQ ID NO: 74), or a light chain with a CDR1 comprising an amino sequence TGSSSNIGAGYDVH (SEQ ID NO: 61); a CDR2 comprising an amino sequence GNNNRPS (SEQ ID NO: 62); and a CDR3 comprising an amino sequence QSYDKSLTWV (SEQ ID NO: 76); or a light chain with a CDR1 comprising an amino sequence TGTSSNIGAGYDVH (SEQ ID NO: 79); a CDR2 comprising an amino sequence GNNNRPS (SEQ ID NO: 62); and a CDR3 comprising an amino sequence QSYDKSLSWV (SEQ ID NO: 80); or a light chain with a CDR1 comprising an amino sequence TGSSSNIGAGFDVH; a CDR2 comprising an amino sequence GNNNRPS; and a CDR3 comprising an amino sequence QSYDSSLSAWV (SEQ ID NO: 82); or a light chain with a CDR1 comprising an amino sequence TGSSSNIGAGYDVH (SEQ ID NO: 61); a CDR2 comprising an amino sequence GNSNRPS(SEQ ID NO: 72); and a CDR3 comprising an amino sequence QSYDSSLSAWV (SEQ ED NO: 82).

In some embodiments the antibody has a heavy chain comprising an amino acid sequence of SEQ ID NOs 1, 3-23, and a light chain comprising an amino acid sequence of SEQ ID NOs: 2 and 24-44. The amino acid and nucleic acid sequences are exemplified in Table 3 below.

TABLE 3

EXEMPLARY CAIX ANTIBODY SEQUENCES

CAIX G250 Heavy Chain CDR_001
SEQ ID NO: 1
QVQLVQSGGGLVQPGGSLRLSCAASGFTFSSYAMSWVRQAPGKGLEWVSAISGSGGSTYYADSVK
GRFTISRDNSKNTLYLQMNSLRAEDTAVYYCARNGNYRGSLAFDIWGQGTLVTVSS CAIX G250 Light Chain CDR_001
SEQ ID NO: 2
QSVLTQPPSVSGAPGQRVTISCTGSSSNIGAGYDVHWYQQLPGTAPKLLIYGNNNRPSGVPDRFS
GSKSGTSASLAITGLQAEDEADYYCQSYDSSLSAWVFGGGTKLTVLG CAIX G250 Heavy Chain CDR Clone 36
SEQ ID NO: 3
EVQLVQSGGGVVQPGGSLRLSCAASGFPFSSYAMSWVRQAPGKGLEWVSAISANGGTTYYADSVK
GRFTISRDNSKNTLYLQMNSLRAEDTAVYYCANNGNYRGAFDIWGQGTMVTVSS CAIX G250 Heavy Chain CDR Clone 10
SEQ ID NO: 4
QVQLVQSGGGLVQPGGSLRLSCAASGFPFSSYAMSWVRQAPGKGLEWVSAISANGGTTYYADSVK
GRFTISPDNSKNTLYLQMNSLRAEDTAVYYCANNGNYRGAFDIWGQGTMVTVSS CAIX G250 Heavy Chain CDR Clone 119
SEQ ID NO: 5
QVQLVQSGGGLVQPGGSLRLSCAASGFPFSSYAMSWVRQAPGKGLEWVSAISANGGTTYYADSVK
GRFTISRDNSKNTLYLQMNSLRAEDTAVYYCANNGNYRGAFDIWGQGTMVTVSS CAIX G250 Heavy Chain CDR Clone 6
SEQ ID NO: 6
QVQLVQSGGGLVQPGGSLRLSCAASEFTFGTYAMTWVRQAPGKGLEWVSAVSGSGGSTYYADSVK
GRFTISPDNSPNTLYLQMNSLRADDTAVYYCARGPVLRYGFDIWGQGTMVTVSS CAIX G250 Heavy Chain CDR Clone 37
SEQ ID NO: 7
QVQLVQSGGGVVQPGGSLRLSCAASGFPFSSYAMSWVRQAPGKGLEWVSAISANGGTTYYADSVK
GRFTISRDNSKNTLYLQMNSLRAEDTAVYYCANNGNYRGAFDIWGQGTMVTVSS CAIX G250 Heavy Chain CDR Clone 104
SEQ ID NO: 8
QVQLQESGGGLVQPGGSLRLSCAASGFTFSIYAMSWVRQAPGKGLEWVSAISGSGGGTYHADSVK
GRFTISRDNSKNTLYLQMNSLRAEDTAVYYCAKFSAYSGYDLWGQGTLVTVSS CAIX G250 Heavy Chain CDR Clone 62
SEQ ID NO: 9
QVQLVQSGGGLVRPGGSLRLSCAASGFPFSSYAMSWVRQAPGKGLEWVSAISANGGTTYYADSVK
GRFTISRDNSKNTLYLQMNSLRAEDTAVYYCANNGNYRGAFDIWGQGTTVTVSS CAIX G250 Heavy Chain CDR Clone 45
SEQ ID NO: 10
QVQLVQSGGGLVQPGGSLRLSCAASGFPFSSYAMSWVRAQPGKGLEWVSAISANGGTTYYADSVK
GRFTISRDNSKNTLYLQMNSLRAEDTAVYYCANNGNYRGAFDIWGQGTMVTVSS CAIX G250 Heavy Chain CDR Clone 119
SEQ ID NO: 11
EVQLVQSGGGLVQPGGSLRLSCAASGFTFSSYAMSWVRQAPGKGLEWVSAISANGGTTYYADSVK
GRFTISRDNSKNTLYLQMNSLRAEDTAVYYCANNGNYRGAFDIWGQGTTVTVSS CAIX G250 Heavy Chain CDR Clone 106
SEQ ID NO: 12
QVQLVQSGGGLVQPGGSLRLSCAASGFTFSSYAMSWVRQAPGKGLEWVSAISGSGGSTYYADSVK
GRFTISRDNSKNTLYLQMNSLRAEDTAVYYCARAAAGFDYWGQGTLVTVSS CAIX G250 Heavy Chain CDR Clone 39
SEQ ID NO: 13
QVQLQESGGGLVQPGGSLRLSCAASGFTFSSYAMSWVRQAPGKGLEWVSAISGSGGSTYYADSVK
GRFTISRDNSKNTLYLQMNSLRAEDTAVYYCAKIGRYSSSLGYWGQGTLVTVSS TABLE 3-continued

EXEMPLARY CAIX ANTIBODY SEQUENCES

CAIX G250 Heavy Chain CDR Clone 94
SEQ ID NO: 14
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAREAPYSSSLDAFDIWGQGTMVTVSS CAIX G250 Heavy Chain CDR Clone 9
SEQ ID NO: 15
QVQLQESGGGLVQPGGSLRLSCAASGFTFSSYAMSWVRQAPGKGLEWVSAISGSGGSTYYADSVK
GRFTISRDNSKNTLYLQMNSLRAEDTAVYYCARSHSSGGFDYWGQGTLVTVSS CAIX G250 Heavy Chain CDR Clone 21
SEQ ID NO: 16
QVQLQESGGGLVQPGGSLRLSCAASGFTFSSYAMSWVRQAPGKGLEWVSAISGSGGSTYYADSVK
GRFTISRDNSKNTLYLQMNSLRAEDTAVYYCARSHSSGGFDYWGQGTLVTVSS G250 Heavy Chain CDR Clone 2
SEQ ID NO: 17
QVTLKESGGGVVQPGTSLRLSCAASGFTFSNYAMTWVRQAPGKGLEWVGLISYDGSVTHYTDSVK
GRFTISRDNAKNSLYLQMNTLRADDTAVYYCARGSGYQEHWGQGTLVTVSS CAIX G250 Heavy Chain CDR Clone 40
SEQ ID NO: 18
QVQLVQSGGGLVQPGGSLRLSCAASGFTFSSYAMSWVRQAPGKGLEWVSAISGSGGSTYYADSVK
GRFTISRDNSKNTLYLQMNSLRAEDTAVYYCATYGDYGSLDYWGQGTLVTVSS CAIX G250 Heavy Chain CDR Clone 57
SEQ ID NO: 19
QVQLVQSGGGLVQPGGSLRLSCAASGFTFSSYAMSWVRQAPGKGLEWVSAISGSGVSTYYADSVK
GRFTISRDNSKNTLYLQMNSLRAEDTAVYYCAKYCSSTSCYRGMDVWGKGTLVTVSS CAIX G250 Heavy Chain CDR Clone 82
SEQ ID NO: 20
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCARGRAARPPFDYWGQGTLVTVSS CAIX G250 Heavy Chain CDR Clone 98
SEQ ID NO: 21
QVQLVQSGGGVVQPGGSLRLSCAASGFPFSSYAMSMVRQAPGKGLEWVSAISANGGTTYYADSVK
GRFTISRDNSKNTLYLQMNSLRAEDTAVYYCANNGNYRGAFDIWGQGTMVTVSS CAIX G250 Heavy Chain CDR Clone 124
SEQ ID NO: 22
QVQLVQSGGGLVQPGGSLRLSCAAPEFTFSKYAMSWVRQAPGKGLEWVSGISGSGGSTYYADSVK
GRFTISRDNSKNTLYLQMNSLRAEDTAVYYCAKSSRSGYFLPLDYWGQGTLVTVSS CAIX G250 Heavy Chain CDR Clone 125
SEQ ID NO: 23
EVQLVESGGGVVQPGRSLRLSCAASGFTFSSYGMHWVRQAPGKGLEWVSAISGSGGSTYYADSVK
GRFTISRDNAKNTLYLQMNSLRAEDTAVYYCARAAVTGGFDPWGQGTLVTVSS CAIX G250 Light Chain CDR Clone 36
SEQ ID NO: 24
QSVLTQPPSVSGAPGQRVTISCTGSSSNIGAGFDVHWYQQLPGTAPKLLIYGNTNRPSGVPDRFS
GSKSGTSASLAITGLQAEDETDYYCQSYDSRLSAWVFGGGTKLTVLG CAIX G250 Light Chain CDR Clone 10
SEQ ID NO: 25
QSVLTQPPSVSGAPGQRVTISCTGSSSNIGAGYDVHWYQQLPGTAPKLLIYGNSNRPSGVPDRFS
GSKSGSSASLAITGLQAEDEAHYYCQSYDRSLSWVFGGGTKLTVLG CAIX G250 Light Chain CDR Clone 119
SEQ ID NO: 26
QSVLTQPPSVSGAPGQRVTISCTGSSSNIGAGYDVHWYQQLPGTAPKLLIYGNTNRPSGVPDRFS
GSKSGTSASLAIIGLQADDEADYYCQSYDSTLRVWMFGGGTKLTVLG TABLE 3-continued

EXEMPLARY CAIX ANTIBODY SEQUENCES

CAIX G250 Light Chain CDR Clone 6
SEQ ID NO: 27
VLTQPPSVSGAPGQRITISCTGSRSNIGADYDVHWYQQLPGTAPKLLIYANNNRPSGVPGRFSAS

KSGTSASLAISGLQAEDEADYYCQSYDSSLRAWVFGGGTKLAVLG

CAIX G250 Light Chain CDR Clone 37
SEQ ID NO: 28
QSVLTQPPSVSGAPGQRITISCTGSRSNIGADYDVHWYQQLPGTAPKLLIYANNNRPSGVPDRFS

GSKSGTSASLAITGLQAEDETDYFCQSYDSSLSAWVFGGGTKVTVLG

CAIX G250 Light Chain CDR Clone 104
SEQ ID NO: 29
QSVLTQPPSVSGAPGQRVTISCTGSSSNIGRGYNVHWYQQLPGTAPKLLIYDNTNRPSGVPARFS

GSKSATSASLTITGLQADDEADYYCQSYDSGLRWVFGGGTKLTLLG

CAIX G250 Light Chain CDR Clone 62
SEQ ID NO: 30
QSVLTQPPSVSGAPGQRITISCTGSSSNIGAGYDVHWYQQVPGKAPKVVIYGNNNRPSGVPDRFS

GSKSGASASLAITGLQTEDEADYYCQSYDKSLTWVFGGGTKVTVLG

CAIX G250 Light Chain CDR Clone 45
SEQ ID NO: 31
QSVLTQPPSVSGAPGQRITISCTGTSSNIGAGYDVHWYQQLPGAAPRVLIYGNNNRPSGVPDRFS

GSKSGTSASLAITFLQSEDEADYYCQSYDKSLSWVFGGGTKLTVLR

CAIX G250 Light Chain CDR Clone 106
SEQ ID NO: 32
QSVLTQPPSVSGAPGQRVTISCTGSSSNIGAGFDVHWYQQLPGTAPRLLIYGNNNRPSGVPDRFS

GSKSGTSASLAITGLQAEDETDYFCQSYDSSLSAWVFGGGTKVTVLR

CAIX G250 Light Chain CDR Clone 18
SEQ ID NO: 33
QSVLTQPPSVSGAPGQRVTISCTGSSSNIGRGYNVHWYQQLPGTAPKLLIYDDTNRPSGVPHRFS

GSKSGTSASLAITGLQAEDEADYYCQSYDSSLRAWVFGGGTKLAVLG

CAIX G250 Light Chain CDR Clone 39
SEQ ID NO: 34
QSVLTQPPSVSGAPGQRVTISCTGSSSNIGRGYNVHWYQQLPGTAPKLLIYDNTNRPSGVPARFS

GSKSATSASLAITGLQADDEADYYCQSYDSGLRWVFGGGTKLTLLR

CAIX G250 Light Chain CDR Clone 94
SEQ ID NO: 35
QSVLTQPPSVSGAPGQRVTISCTGSSSNIGRGYNVHWYQQLPGTAPKLLIYGNSNRPSGVPDRFS

GSSSGNTASLTITGAQAEDEADYYCHSRDNNGHHIFGGGTKLTVLS

CAIX G250 Light Chain CDR Clone 9
SEQ ID NO: 36
QSVLTQPPSVSGAPGQRVTISCTGSSSNIGRGYNVHWYQQLPGTAPKLLIYGNTNRPSGVPDRFS

GSKSGTSASLAITGLQAEDEGDYYCQSYDSSLSAWVFGGGTKLTVLG

CAIX G250 Light Chain CDR Clone 21
SEQ ID NO: 37
QSVLTQPPSVSGAPGQRVTISCTGSSSNIGRGYNVHWYQQLPGTAPKLLIYGNTNRPSGVPDRFS

GSKSGTSASLAITGLQAXDEGDYYCQSYDSSLSAWVFGGGTKLTVLG

CAIX G250 Light Chain CDR Clone 27
SEQ ID NO: 38
LPVLTQPPSVSVAPGQTARITCGGNNIGSKSVHWYQQKPGQAPVLVIYYDSDRPSGIPERFSGSN

SGNTATLTISRVEAGDEADYYCQVWDSSSDHHVVFGGGTKLTVLG

CAIX G250 Light Chain CDR Clone 40
SEQ ID NO: 39
QSVLTQPPSVSGAPGQRVTISCTGSSSNIGAGYDVHWYQQLPGTAPKLLIYANNNRPSGVPDRFS

GSKSGTSASLAITGLQAEDEADYYCQSYDSSLRAWVFGGGTKLAVLG

TABLE 3-continued

EXEMPLARY CAIX ANTIBODY SEQUENCES

CAIX G250 Light Chain CDR Clone 57
SEQ ID NO: 40
QSVLTQPPSVSGAPGQRVTISCTGSSSNIGAGYDVHWYQQLPGTAPKLLIYANNNRPSGVPDRFS

GSKSGTSASLAITGLQAEDEADYYCQSYDSSLRAWVFGGGTKLAVLG

CAIX G250 Light Chain CDR Clone 82
SEQ ID NO: 41
QPVLTQPPSASGTPGQRVTISCSGSSSNIGSNYVYWYQQLPGTAPKLPIYRNNQRPSGVPDRFSG

SKSGTSASLAISGLRSEDEADYYCAAWDDSLNGVVFGGGTKLTVLR

CAIX G250 Light Chain CDR Clone 98
SEQ ID NO: 42
QSVLTQPPSVSGAPGQRVTISCTGSSSNIGAGYDVHWYQHLPGTAPKLLIYGNSNRPSGVPDRFS

GSKSGTSASLAITGLQAEDETDYFCQSYDSSLSAWVFGGGTKVTVLG

CAIX G250 Light Chain CDR Clone 124
SEQ ID NO: 43
SSELTQDPAVSVALGQTVRITCQGNSLRYYYPSWYQQKPGQAPVLVIYGKNNRPSGIPDRFSGSS

SGNTASLTITGTQAEDEADYYCSSRDNTDNRVVFGGGTKLTVLG

CAIX G250 Light Chain CDR Clone 125
SEQ ID NO: 44
QPGLTQPPSVSVAPGQTARITCGGDNIGRKSVHWYQQRPGQAPILVIRDDRDRPSGIPERFSGSS

SVNTATLIISRVEAGDEADYYCQVWDSSSKHYVFGPGTKVTALG

HCA IX
SEQ ID NO: 45
MAPLCPSPWLPLLIPAPAPGLTVQLLLSLLLLMPVHPQRLPRMQEDSPLGGGSSGEDDPLGEEDL

PSEEDSPREEDPPGEEDLPGEEDLPEVKPKSEEEGSLKLEDLPTVEAPGDPQEPQNNAH

RDKEGDDQSHWRYGGDPPWPRVSPACAGRFQSPVDIRPQLAAFCPALRPLELLGFQLPPLPELRL

RNNGHSVQLTLPPGLEMALGPGREYALQLHLHWGAAGRPGSEHTVEGHRFPAEIHVVHLSTAFAR

VDEALGRPGGLAVLAAFLEEGPEENSAYEQLLSRLEEIAEEGSETQVPGLDISALLPSDFSRYFQ

YEGSLTTPPCAQGVIWTVFNQTVMLSAKQLHTLSDTLWGPGDSRLQLNFRATQPLNGRVIEASFP

AGVDSSPRAAEPVQLNSCLAAGDILALVFGLLFAVTSVAFLVQMRRQHRRGTKGGVSYRPAEVAE

TGA

MCA IX
SEQ ID NO: 46
MASLGPSPWAPLSTPAPTAQLLLFLLLQVSAQPQGLSGMQGEPSLGDSSSGEDELGVDVLPSEED

APEEADPPDGEDPPEVNSEDRMEESLGLEDLSTPEAPEHSQGSHGDEKGGGHSHWSYGGTLLWPQ

VSPACAGRFQSPVDIRLERTAFCRTLQPLELLGYELQPLPELSLSNNGHTVQLTLPPGLKMALGP

GQEYRALQLHLHWGTSDHPGSEHTVNGHRFPAEIHVVHLSTAFSELHEALGRPGGLAVLAAFLQE

SPEENSAYEQLLSHLEEISEEGSKIEIPGLDVSALLPSDFSRYYRYEGSLTTPPCSQGVIWTVFN

ETVKLSAKQLHTLSVSLWGPRDSRLQLNFRATQPLNGRTIEASFPAAEDSSPEPVHVNSCFTAGD

ILALVFGLLFAVTSIAFLLQLRRQHRHRSGTKDRVSYSPAEMTETGA

G10 human anti-CAIX antibody gene
SEQ ID NO: 83
CAGGTGCAGCTGGTGCAGTCTGGGGGAGGCTTGGTACAGCCTGGGGGGTCCCTGAGACTCTCCTG

TGCAGCCTCTGGATTCCCCTTTAGCAGCTATGCCATGAGCTGGGTCCGCCAGGCTCCAGGGAAGG

GGCTGGAGTGGGTCTCAGCTATTAGTGCTAATGGTGGTACCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGAATAATGGGAACTATCGCGGTGCTTTTGATATCT

GGGGCCAAGGGACAATGGTCACCGTCTCTTCAGGTGGCGGCGGTTCCGGAGGTGGTGGTTCTGGC

TABLE 3-continued

EXEMPLARY CAIX ANTIBODY SEQUENCES

GGTGGTGGCAGCCAGTCTGTGCTGACTCAGCCACCCTCAGTGTCTGGGGCCCCAGGGCAGAGGGT

CACCATCTCCTGCACTGGGAGCAGCTCCAACATCGGGGCAGGTTATGATGTACACTGGTACCAGC

AGCTTCCAGGAACAGCCCCCAAACTCCTCATCTATGGTAACAGCAATCGGCCCTCAGGGGTCCCT

GACCGATTCTCTGGCTCCAAGTCTGGCTCCTCAGCCTCCCTGGCCATCACTGGGCTCCAGGCTGA

GGATGAGGCTCATTATTACTGCCAGTCATATGACAGAAGCCTGTCTTGGGTGTTCGGCGGAGGGA

CCAAATTGACCGTCCTAGGT

G10 human anti-CAIX partial cds

SEQ ID NO: 84

QVQLVQSGGGLVQPGGSLRLSCAASGFPFSSYAMSWVRQAPGKGLEWVSAISANGGTTYYADSVK

GRFTISRDNSKNTLYLQMNSLRAEDTAVYYCANNGNYRGAFDIWGQGTMVTVSSGGGGSGGGGSG

GGGSQSVLTQPPSVSGAPGQRVTISCTGSSSNIGAGYDVHWYQQLPGTAPKLLIYGNSNRPSGVP

DRFSGSKSGSSASLAITGLQAEDEAHYYCQSYDRSLSWVFGGGTKLTVLG

G104 human anti-CAIX antibody gene

SEQ ID NO: 85

CAGGTGCAGCTGCAGGAGTCGGGGGGAGGCTTGGTACAGCCTGGGGGGTCCCTGAGACTCTCCTG

TGCAGCCTCTGGATTCACCTTTAGCATCTATGCCATGAGCTGGGTCCGCCAGGCTCCAGGGAAGG

GGCTGGAGTGGGTCTCAGCTATTAGTGGTAGTGGTGGTGGCACATACCACGCAGACTCCGTGAAG

GGCCGGTTCACCATCTCCAGAGACAATTCCAAGAACACGCTGTATCTGCAAATGAACAGCCTGAG

AGCCGAGGACACGGCCGTCTATTACTGTGCGAAATTCTCTGCGTATAGTGGCTACGATTTGTGGG

GCCAGGGAACCCTGGTCACCGTCTCCTCAGGTGGCGGCGGTTCCGGAGGTGGTGGTTCTGGCGGT

GGTGGCAGCCAGTCTGTGCTGACTCAGCCACCCTCAGTGTCTGGGGCCCCAGGGCAGAGGGTCAC

AATCTCCTGCACTGGGAGCAGCTCCAACATCGGGAGAGGTTATAATGTACACTGGTACCAGCAGC

TTCCAGGAACAGCCCCCAAACTCCTCATCTATGATAACACGAATCGGCCCTCAGGGGTCCCTGCC

CGATTCTCTGGCTCCAAGTCTGCCACGTCAGCCTCCCTGACCATCACTGGGCTCCAGGCTGACGA

TGAGGCTGATTATTACTGCCAGTCGTATGACAGCGGCCTGAGGTGGGTGTTCGGCGGAGGGACCA

AGCTGACCCTCCTAGGT

G104 human anti-CAIX antibody partial cds

SEQ ID NO: 86

QVQLQESGGGLVQPGGSLRLSCAASGFTFSIYAMSWVRQAPGKGLEWVSAISGSGGGTYHADSVK

GRFTISRDNSKNTLYLQMNSLRAEDTAVYYCAKFSAYSGYDLWGQGTLVTVSSGGGGSGGGGSGG

GGSQSVLTQPPSVSGAPGQRVTISCTGSSSNIGRGYNVHWYQQLPGTAPKLLIYDNTNRPSGVPA

RFSGSKSATSASLTITGLQADDEADYYCQSYDSGLRWVFGGGTKLTLLG

G106 human anti-CAIX antibody gene

SEQ ID NO: 87

GAGGTGCAGCTGGTGCAGTCTGGGGGAGGCTTGGTACAGCCGGGGGGGTCCCTGAGACTCTCCTG

TGCAGCCTCTGGATTCACCTTTAGCAGCTATGCCATGAGCTGGGTCCGCCAGGCTCCAGGGAAGG

GGCTGGAGTGGGTCTCAGCTATTAGTGCTAATGGTGGTACCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGAATAATGGAACTATCGCGGTGCTTTTGATATCT

GGGGCCAAGGGACCACGGTCACCGTCTCCTCAGGTGGCGGCGGTTCCGGAGGTGGTGGTTCTGGC

GGTGGTGGCAGCCAGTCTGTGCTGACTCAGCCACCCTCAGTGTCTGGGGCCCCAGGGCAGAGGGT

CACCATCTCCTGCACTGGGAGCAGCTCCAACATCGGGGCAGGTTTTGATGTACACTGGTACCAGC

AACTTCCAGGAACAGCCCCCAGACTCCTCATCTATGGTAACAACAATCGGCCCTCAGGGGTCCCT

TABLE 3-continued

EXEMPLARY CAIX ANTIBODY SEQUENCES

```
GACCGATTCTCTGGCTCCAAGTCTGGCACCTCAGCCTCCCTGGCCATCACTGGGCTCCAGGCTGA

GGATGAGACTGATTATTTCTGCCAGTCCTATGACAGCAGCCTGAGTGCTTGGGTATTCGGCGGAG

GGACCAAGGTGACCGTCCTACGT
```

G106 human anti-CAIX antibody partial cds
SEQ ID NO: 88
```
EVQLVQSGGGLVQPGGSLRLSCAASGFTFSSYAMSWVRQAPGKGLEWVSAISANGGTTYYADSVK

GRFTISRDNSKNTLYLQMNSLRAEDTAVYYCANNGNYRGAFDIWGQGTTVTVSSGGGGSGGGGSG

GGGSQSVLTQPPSVSGAPGQRVTISCTGSSSNIGAGFDVHWYQQLPGTAPRLLIYGNNNRPSGVP

DRFSGSKSGTSASLAITGLQAEDETDYFCQSYDSSLSAWVFGGGTKVTVLR
```

G119 human anti-CAIX antibody gene
SEQ ID NO: 89
```
CAGGTGCAGCTGGTGCAGTCTGGGGGAGGCTTGGTACAGCCTGGGGGGTCCCTGAGACTCTCCTG

TGCAGCCTCTGGATTCCCCTTTAGCAGCTATGCCATGAGCTGGGTCCGCCAGGCTCCAGGGAAGG

GGCTGGAGTGGGTCTCAGCTATTAGTGCTAATGGTGGTACCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGAATAATGGGAACTATCGCGGTGCTTTTGATATCT

GGGGCCAAGGGACAATGGTCACCGTCTCTTCAGGTGGCGGCGGTTCCGGAGGTGGTGGTTCTGGC

GGTGGTGGCATCCAGTCTGTGCTGACTCAGCCACCCTCAGTGTCTGGGGCCCCAGGGCAGAGGGT

CACCATCTCCTGCACTGGGAGCAGCTCCAACATCGGGGCAGGTTATGATGTACACTGGTACCAGC

AGCTTCCAGGAACAGCCCCCAAACTCCTCATCTATGGTAACACCAATCGGCCCTCAGGGGTCCCT

GACCGATTCTCTGGCTCCAAGTCTGGCACCTCAGCCTCCCTGGCCATCATTGGGCTCCAGGCTGA

CGATGAGGCTGATTATTACTGCCAGTCCTATGACAGCACCCTGAGGGTCTGGATGTTCGGCGGAG

GGACCAAGCTGACCGTCCTTGGT
```

G119 human anti-CAIX antibody partial cds
SEQ ID NO: 90
```
QVQLVQSGGGLVQPGGSLRLSCAASGFPFSSYAMSWVRQAPGKGLEWVSAISANGGTTYYADSVK

GRFTISRDNSKNTLYLQMNSLRAEDTAVYYCANNGNYRGAFDIWGQGTMVTVSSGGGGSGGGGSG

GGGIQSVLTQPPSVSGAPGQRVTISCTGSSSNIGQGYDVHWYQQLPGTAPKLLIYGNTNRPSGVP

DRFSGSKSGTSASLAIIGLQADDEADYYCQSYDSTLRVWMFGGGTKLTVLG
```

G125 human anti-CAIX antibody gene
SEQ ID NO: 91
```
GAGGTGCAGCTGGTGGAGTCTGGGGGAGGCGTGGTCCAGCCTGGGAGGTCCCTGAGACTCTCCTG

TGCAGCCTCTGGATTCACCTTCAGTAGCTATGGCATGCACTGGGTCCGCCAGGCTCCAGGGAAGG

GGCTGGAGTGGGTCTCAGCTATTAGTGGTAGTGGTGGTAGCACATACTACGCAGACTCCGTGAAG

GGCCGATTCACCATCTCCAGAGACAACGCCAAGAACACGCTGTATCTGCAAATGAACAGTCTGAG

AGCCGAGGACACGGCTGTGTATTACTGTGCAAGAGCCGCGGTAACAGGAGGCTTCGACCCCTGGG

GCCAGGGCACCCTGGTCACCGTCTCCTCAGGTGGCGGCGGTTCCGGAGGTGGTGGTTCTGGCGGT

GGTGGCAGCCAGCCTGGGCTGACTCAGCCACCCTCGGTGTCAGTGGCCCCAGGACAGACGGCCAG

GATTACCTGTGGGGGAGACAATATTGGAAGAAAAAGTGTGCACTGGTACCAACAGAGGCCAGGCC

AGGCCCCTATTCTAGTCATCCGTGATGATAGGGATCGGCCCTCAGGGATCCCTGAGCGATTCTCT

GGCTCCAGCTCTGTGAATACGGCCACCCTGATCATCAGCAGGGTCGAAGCCGGAGATGAGGCCGA

CTATTATTGTCAGGTGTGGGATAGTAGTAGTAAACATTATGTCTTCGGACCAGGGACCAAGGTCA

CCGCCCCTAAGT
```

TABLE 3-continued

EXEMPLARY CAIX ANTIBODY SEQUENCES

G125 human anti-CAIX antibody partial cds
SEQ ID NO: 92
EVQLVESGGGVVQPGRSLRLSCAASGFTFSSYGMHWVRQAPGKGLEWVSAISGSGGSTYYADSVK
GRFTISRDNAKNTLYLQMNSLRAEDTAVYYCARAAVTGGFDPWGQGTLVTVSSGGGGSGGGGSGG
GGSQPGLTQPPSVSVAPGQTARITCGGDNIGRKSVHWYQQRPGQAPILVIRDDRDRPSGIPERFS
GSSSVNTATLIISRVEAGDEADYYCQVWDSSSKHYVFGPGTKVTALG G27 human anti-CAIX antibody gene
SEQ ID NO: 93
CAGGTCACCTTGAAGGAGTCTGGGGGAGGCGTGGTCCAGCCTGGGACGTCCCTGAGACTCTCCTG
TGCAGCCTCTGGATTCACCTTTAGCAACTATGCCATGACGTGGGTCCGCCAGGCTCCAGGGAAGG
GGCTGGAGTGGGTGGGTCTAATATCTTATGATGGAAGTGTTACACACTACACAGACTCGGTGAAG
GGCCGATTCACCATCTCCAGAGACAACGCCAAGAACTCACTGTATTTGCAAATGAACACCCTGAG
AGCCGACGACACGGCTGTGTATTATTGTGCGAGAGGCTCCGGCTACCAAGAACACTGGGGCCAGG
GAACCCTGGTCACCGTCTCCTCAGGTGGCGGCGGTTCCGGAGGTGGTGGTTCTGGCGGTGGTGGC
AGCCTGCCTGTGCTGACTCAGCCACCCTCGGTGTCAGTGGCCCCAGGACAGACGGCCAGGATTAC
CTGTGGGGGAAACAACATTGGAAGTAAAAGTGTGCACTGGTACCAGCAGAAGCCAGGCCAGGCCC
CTGTGCTGGTCATCTATTATGATAGCGACCGGCCCTCAGGGATCCCTGAGCGATTCTCTGGCTCC
AACTCTGGGAACACGGCCACCCTGACCATCAGCAGGGTCGAAGCCGGGGATGAGGCCGACTATTA
CTGTCAGGTGTGGGATAGTAGTAGTGATCATCATGTGGTATTCGGCGGAGGGACCAAGCTGACCG
TCCTAGGT G27 human anti-CAIX antibody partial cds
SEQ ID NO: 94
QVTLKESGGGVVQPGTSLRLSCAASGFTFSNYAMTWVRQAPGKGLEWVGLISYDGSVTHYTDSVK
GRFTISRDNAKNSLYLQMNTLRADDTAVYYCARGSGYQEHWGQGTLVTVSSGGGGSGGGGSGGGG
SLPVLTQPPSVSVAPGQTARITCGGNNIGSKSVHWYQQKPGQAPVLVIYYDSDRPSGIPERFSGS
NSGNTATLTISRVEAGDEADYYCQVWDSSSDHHVVFGGGTKLTVLG G36 human anti-CAIX antibody gene
SEQ ID NO: 95
GAGGTGCAGCTGGTGCAGTCTGGGGGAGGCGTGGTACAGCCTGGGGGGTCCCTGAGACTCTCCTG
TGCAGCCTCTGGATTCCCCTTTAGCAGCTATGCCATGAGCTGGGTCCGCCAGGCTCCAGGGAAGG
GGCTGGAGTGGGTCTCAGCTATTAGTGCTAATGGTGGTACCACATACTACGCAGACTCCGTGAAG
GGCCGGTTCACCATCTCCAGAGACAATTCCAAGAACACGCTGTATCTGCAAATGAACAGCCTGAG
AGCCGAGGACACGGCCGTATATTACTGTGCGAATAATGGGAACTATCGCGGTGCTTTTGATATCT
GGGGCCAAGGGACAATGGTCACCGTCTCTTCAGGTGGCGGCGGTTCCGGAGGTGGTGGTTCTGGC
GGTGGTGGCAGCCAGTCTGTGCTGACTCAGCCACCCTCAGTGTCTGGGGCCCCAGGGCAGAGGGT
CACCATCTCCTGCACTGGGAGCAGCTCCAACATCGGGGCAGGTTTTGATGTACACTGGTACCAGC
AGCTTCCAGGAACAGCCCCCAAACTCCTCATCTACGGTAACACCAATCGACCCTCAGGGGTCCCT
GACCGATTCTCTGGCTCCAAGTCTGGCACCTCAGCCTCCCTGGCCATCACTGGGCTCCAGGCTGA
GGATGAGACTGATTATTACTGCCAGTCCTATGACAGTAGACTGAGTGCTTGGGTGTTCGGCGGAG
GGACCAAGCTGACCGTCCTAGGT G36 human anti-CAIX antibody partial cds
SEQ ID NO: 96
EVQLVQSGGGVVQPGGSLRLSCAASGFPFSSYAMSWVRQAPGKGLEWVSAISANGGTTYYADSVK
GRFTISRDNSKNTLYLQMNSLRAEDTAVYYCANNGNYRGAFDIWGQGTMVTVSSGGGGSGGGGSG TABLE 3-continued

EXEMPLARY CAIX ANTIBODY SEQUENCES

GGGSQSVLTQPPSVSGAPGQRVTISCTGSSSNIGAGFDVHWYQQLPGTAPKLLIYGNTNRPSGVP

DRFSGSKSGTSASLAITGLQAEDETDYYCQSYDSRLSAWVFGGGTKLTVLG

G37 human anti-CAIX antibody gene
SEQ ID NO: 97
CAGGTGCAGCTGGTGCAGTCTGGGGGAGGCGTGGTACAGCCTGGGGGGTCCCTGAGACTCTCCTG

TGCAGCCTCTGGATTCCCCTTTAGCAGCTATGCCATGAGCTGGGTCCGCCAGGCTCCAGGGAAGG

GGCTGGAGTGGGTCTCAGCTATTAGTGCTAATGGTGGTACCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGAATAATGGGAACTATCGCGGTGCTTTTGATATCT

GGGGCCAAGGGACAATGGTCACCGTCTCTTCAGGTGGCGGCGGTTCCGGAGGTGGTGGTTCTGGC

GGTGGTGGCAGCCAGTCTGTGCTGACTCAGCCACCCTCAGTGTCTGGGGCCCCAGGGCAGAGGGT

CACCATCTCCTGCACTGGGAGCAGCTCCAACATCGGGGCAGGTTATGATGTTCACTGGTACCAGC

ACCTTCCAGGAACAGCCCCCAAACTCCTCATCTATGGTAATAGCAATCGACCCTCAGGAGTCCCT

GACCGATTCTCTGGCTCCAAGTCTGGCACCTCAGCCTCCCTGGCCATCACTGGGCTCCAGGCTGA

GGATGAGACTGATTATTTCTGCCAGTCCTATGACAGCAGCCTGAGTGCTTGGGTATTCGGCGGAG

GGACCAAGGTGACCGTCCTAGGT

G37 human anti-CAIX antibody partial cds
SEQ ID NO: 98
QVQLVQSGGGVVQPGGSLRLSCAASGFPFSSYAMSWVRQAPGKGLEWVSAISANGGTTYYADSVK

GRFTISRDNSKNTLYLQMNSLRAEDTAVYYCANNGNYRGAFDIWGQGTMVTVSSGGGGSGGGGSG

GGGSQSVLTQPPSVSGAPGQRVTISCTGSSSNIGAGYDVHWYQHLPGTAPKLLIYGNSNRPSGVP

DRFSGSKSGTSASLAITGLQAEDETDYFCQSYDSSLSAWVFGGGTKVTVLG

G39 human anti-CAIX antibody gene
SEQ ID NO: 99
CAGGTGCAGCTGCAGGAGTCGGGGGGAGGCTTGGTACAGCCTGGGGGGTCCCTGAGACTCTCCTG

TGCAGCCTCTGGATTCACCTTTAGCAGCTATGCCATGAGCTGGGTCCGCCAGGCTCCAGGGAAGG

GGCTGGAGTGGGTCTCAGCTATTAGTGGTAGTGGTGGTAGCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGAAAATTGGACGGTATAGCAGCAGCTTGGGGTACT

GGGGCCAGGGCACCCTGGTCACCGTCTCCTCAGGTGGCGGCGGTTCCGGAGGTGGTGGTTCTGGC

GGTGGTGGCAGCCAGTCTGTGCTGACTCAGCCACCCTCAGTGTCTGGGGCCCCAGGGCAGAGGGT

CACAATCTCCTGCACTGGGAGCAGCTCCAACATCGGGAGAGGTTATAATGTACACTGGTACCAGC

AGCTTCCAGGAACAGCCCCCAAACTCCTCATCTATGATAACACGAATCGGCCCTCAGGGGTCCCT

GCCCGATTCTCTGGCTCCAAGTCTGCCACGTCAGCCTCCCTGGCCATCACTGGGCTCCAGGCTGA

CGATGAGGCTGATTATTACTGCCAGTCGTATGACAGCGGCCTGAGATGGGTGTTCGGCGGGGGGA

CCAAGCTGACCCTCCTACGT

G39 human anti-CAIX antibody partial cds
SEQ ID NO: 100
QVQLQESGGGLVQPGGSLRLSCAASGFTFSSYAMSWVRQAPGKGLEWVSAISGSGGSTYYADSVK

GRFTISRDNSKNTLYLQMNSLRAEDTAVYYCAKIGRYSSSLGYWGQGTLVTVSSGGGGSGGGGSG

GGGSQSVLTQPPSVSGAPGQRVTISCTGSSSNIGRGYNVHQYQQLPGTAPKLLIYDNTNRPSGVP

ARFSGSKSATSASLAITGLQADDEADYYCQSYDSGLRWVFGGGTKLTLLR

TABLE 3-continued

EXEMPLARY CAIX ANTIBODY SEQUENCES

G40 human anti-CAIX antibody gene
SEQ ID NO: 101
CAGGTGCAGCTGGTGCAGTCTGGGGGAGGCTTGGTACAGCCTGGGGGGTCCCTGAGACTCTCCTG

TGCAGCCTCTGGATTCACCTTTAGCAGCTATGCCATGAGCTGGGTCCGCCAGGCTCCAGGGAAGG

GGCTGGAGTGGGTCTCAGCTATTAGTGGTAGTGGTGGTAGCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGACGTACGGTGACTACGGCAGCCTCGACTACTGGG

GCCAGGGCACCCTGGTCACCGTCTCCTCAGGTGGCGGCGGTTCCGGAGGTGGTGGTTCTCGCGGT

GGTGGCAGCCAGTCTGTGCTGACTCAGCCACCCTCAGTGTCTGGGGCCCCAGGGCAGAGGGTCAC

CATCTCCTGCACTGGGAGCAGCTCCAACATCGGGGCAGGTTATGATGTACACTGGTACCAGCAGC

TTCCAGGAACAGCCCCCAAACTCCTCATCTATGCTAACAACAATCGGCCCTCAGGGGTCCCTGAC

CGATTCTCTGGCTCCAAGTCTGGCACCTCAGCCTCCCTGGCCATCACTGGGCTCCAGGCTGAGGA

TGAGGCTGATTATTACTGCCAGTCCTATGACAGCAGCCTGAGGGCTTGGGTGTTCGGCGGAGGGA

CCAAGCTGGCCGTCCTGGGT

G40 human anti-CAIX antibody partial cds
SEQ ID NO: 102
QVQLVQSGGGLVQPGGSLRLSCAASGFTFSSYAMSWVRQAPGKGLEWVSAISGSGGSTYYADSVK

GRFTISRDNSKNTLYLQMNSLRAEDTAVYYCATYGDYGSLDYWGQGTLVTVSSGGGGSGGGGSRG

GGSQSVLTQPPSVSGAPGQRVTISCTGSSSNIGAGYDVHWYQQLPGTAPKLLIYANNNRPSGVPD

RFSGSKSGTSASLAITGLQAEDEADYYCQSYDSSLRAWVFGGGTKLAVLG

G45 human anti-CAIX antibody gene
SEQ ID NO: 103
CAGGTGCAGCTGGTGCAGTCTGGGGGAGGCTTGGTACAGCCTGGGGGGTCCCTGAGACTCTCCTG

TGCAGCCTCTGGATTCCCCTTTAGCAGCTATGCCATGAGCTGGGTCCGCCAGGCTCCAGGGAAGG

GGCTGGAGTGGGTCTCAGCTATTAGTGCTAATGGTGGTACCACATACTACGCAGACTCCGTGAAG

GGCCGGTTCACCATCTCCAGAGACAATTCCAAGAACACGCTGTATCTGCAAATGAACAGCCTGAG

AGCCGAGGACACGGCCGTATATTACTGTGCGAATAATGGGAACTATCGCGGTGCTTTTGATATCT

GGGGCCAAGGGACAATGGTCACCGTCTCTTCAGGTGGCGGCGGTTCCGGAGGTGGTGGTTCTGGC

GGTGGTGGCAGCCAGTCTGTGCTGACTCAGCCACCCTCAGTGTCTGGGGCCCCAGGGCAGAGGAT

CACCATCTCCTGCACTGGGACCAGCTCCAACATCGGGGCAGGTTATGATGTACACTGGTACCAGC

AACTTCCAGGAGCAGCCCCCAGAGTCCTCATCTATGGTAACAACAATCGGCCCTCAGGGGTCCCT

GACCGATTCTCTGGCTCCAAGTCTGGCACCTCAGCCTCCCTGGCCATCACTGGGCTCCAGTCTGA

GGATGAGGCTGATTATTACTGTCAGTCCTATGACAAGAGTCTGAGTTGGGTGTTCGGCGGAGGGA

CCAAGCTGACCGTCCTACGT

G45 human anti-CAIX antibody partial cds
SEQ ID NO: 104
QVQLVQSGGGLVQPGGSLRLSCAASGFPFSSYAMSWVRQAPGKGLEWVSAISANGGTTYYADSVK

GRFTISRDNSKNTLYLQMNSLRAEDTAVYYCANNGNYRGAFDIWGQGTMVTVSSGGGGSGGGGSG

GGGSQSVLTQPPSVSGAPGQRITISCTGTSSNIGAGYDVHWYQQLPGAAPRVLIYGNNNRPSGVP

DRFSGSKSGTSASLAITGLQSEDEADYYCQSYDKSLSWVFGGGTKLTVLR

G57 human anti-CAIX antibody gene
SEQ ID NO: 105
CAGGTGCAGCTGGTGCAGTCTGGGGGAGGCTTGGTACAGCCTGGGGGGTCCCTGAGACTCTCCTG

TGCAGCCTCTGGATTCACCTTTAGCAGCTATGCCATGAGCTGGGTCCGCCAGGCTCCAGGGAAGG

TABLE 3-continued

EXEMPLARY CAIX ANTIBODY SEQUENCES

GGCTGGAGTGGGTCTCAGCTATTAGTGGTAGTGGTGTTAGCACATACTACGCAGACTCCGTGAAG

GGCCGCTTCACCATCTCCAGAGACAATTCCAAGAACACGCTGTATTTGCAAATGAACAGCCTGAG

AGCCGAGGACACGGCCGTATATTACTGTGVGAAATATTGTAGTAGTACCAGCTGCTATCGCGGTA

TGGACGTCTGGGGCAAAGGCACCCTGGTCACCGTCTCCTCAGGTGGCGGCGGTTCCGGAGGTGGT

GGTTCTCGCGGTGGTGGCAGCCAGTCTGTGCTGACTCAGCCACCCTCAGTGTCTGGGCCCCAGG

GCAGAGGGTCACCATCTCCTGCACTGGGAGCAGCTCCAACATCGGGGCAGGTTATGATGTACACT

GGTACCAGCAGCTTCCAGGAACAGCCCCCAAACTCCTCATCTATGCTAACAACAATCGGCCCTCA

GGGGTCCCTGACCGATTCTCTGGCTCCAAGTCTGGCACCTCAGCCTCCCTGGCCATCACTGGGCT

CCAGGCTGAGGATGAGGCTGATTATTACTGCCAGTCCTATGACAGCAGCCTGAGGGCTTGGGTGT

TCGGCGGAGGGACCAAGCTGGCCGTCCTGGGT

G57 human anti-CAIX antibody partial cds

SEQ ID NO: 106

QVQLVQSGGGLVQPGGSLRLSCAASGFTFSSYAMSWVRQAPGKGLEWVSAISGSGVSTYYADSVK

GRFTISRDNSKNTLYLQMNSLRAEDTAVYYCAKYCSSTSCYRGMDVWGKGTLVTVSSGGGGSGGG

GSRGGGSQSVLTQPPSVSGAPGQRVTISCTGSSSNIGAGYDVHWYQQLPGTAPKLLIYANNNRPS

GVPDRFSGSKSGTSASLAITGLQAEDEADYYCQSYDSSLRAWVFGGGTKLAVLG

G6 human anti-CAIX antibody gene

SEQ ID NO: 107

CAGGTGCAGCTGGTGCAGTCTGGGGGAGGCTTGGTACAGCCTGGGGGGTCCCTGAGACTCTCCTG

TGCAGCCTCTGAATTCACCTTTGGTACCTATGCCATGACCTGGGTCCGCCAGGCTCCAGGGAAGG

GGCTGGAGTGGGTCTCGGCTGTTAGTGGTAGTGGTGGTAGCACATACTACGCAGACTCCGTGAAG

GGCCGGTTCACCATCTCCAGAGACAATTCCAGGAACACGCTGTATCTGCAAATGAACAGCCTGAG

AGCCGATGACACGGCCGTGTATTACTGTGCAAGAGGCCCGGTATTACGATATGGCTTTGATATCT

GGGGCCAAGGGACAATGGTCACCGTCTCTTCAGGTGGCGGCGGTTCCGGAGGTGGTGGTTCTGGC

GGTGGTGGCAGCCAGTCTGTGCTGACTCAGCCACCCCTCAGTCTCTGGGCCCCAGGGCAGAGGAT

CACCATCTCCTGCACTGGGAGCAGGTCCAACATCGGGGCAGATTATGATGTACATGGTACCAGC

AGCTTCCAGGAACAGCCCCCAAACTCCTCATCTATGCTAACAACAATCGGCCCTCAGGGGTCCCT

GGTCGATTCTCTGCCTCCAAGTCTGGCACCTCAGCCTCCCTGGCCATCAGTGGGCTCCAGGCTGA

GGATGAGGCTGATTATTACTGCCAGTCGTATGACAGCAGCCTGAGGGCTTGGGTGTTCGGCGGAG

GGACCAAGCTGGCCGTCCTGGGT

G6 human anti-CAIX antibody partial cds

SEQ ID NO: 108

QVQLVQSGGGLVQPGGSLRLSCAASEFTFGTYAMTWVRQAPGKGLEWVSAVSGSGGSTYYADSVK

GRFTISRDNSRNTLYLQMNSLRADDTAVYYCARGPVLRYGFDIWGQTMVTVSSGGGGSGGGGSG

GGSQSVLTQPPSVSGAPGQRITISCTGSRSNIGADYDVHWYQQLPGTAPKLLIYANNNRPSGVP

GRFSASKSGTSASLAISGLQAEDEADYYCQSYDSSLRAWVFGGGTKLAVLG

G9 human anti-CAIX antibody gene

SEQ ID NO: 109

CAGGTGCAGCTGCAGGAGTCGGGGGGAGGCTTGGTCCAGCCTGGGGGGTCCCTGAGACTCTCCTG

TGCAGCCTCTGGATTCACCTTTAGCAGCTATGCCATGAGCTGGGTCCGCCAGGCTCCAGGGAAGG

GGCTGGAGTGGGTCTCAGCTATTAGTGGTAGTGGTGGTAGCACATACTACGCAGACTCCGTGAAG

GGCCGGTTCACCATCTCCAGAGACAATTCCAAGAACACGCTGTATCRGCAAATGAACAGCCTGAG

AGCCGAGGACACGGCCGTATATTACTGTGCGAGGTCCCATAGCAGTGGAGGATTTGACTACTGGG

TABLE 3-continued

EXEMPLARY CAIX ANTIBODY SEQUENCES

GCCAGGGAACCCTGGTCACCGTCTCCTCAGGTGGCGGCGGTTCCGGAGGTGGTGGTTCTGGCGGT

GGTGGCAGCCAGTCTGTGCTGACTCAGCCACCCTCAGTGTCTGGGGCCCCAGGGCAGAGGGTCAC

AATCTCCTGCACTGGGAGCAGCTCCAACATCGGGAGAGGTTATAATGTACACTGGTACCAGCAGC

TTCCAGGAACAGCCCCCAAACTCCTCATCTATGGTAACACCAATCGGCCCTCAGGGGTCCCTGAC

CGATTCTCTGGCTCCAAGTCTGGCACCTCAGCCTCCCTGGCCATCACTGGGCTCCAGGCTGAGGA

TGAGGGTGATTATTACTGCCAGTCCTATGACAGCAGCCTGAGTGCTTGGGTGTTCGGCGGGGGA

CCAAGCTGACCGTCCTAGGT

G9 human anti-CAIX antibody gene partial cds
                                                      SEQ ID NO: 110
QVQLQESGGGLVQPGGSLRLSCAASGFTFSSYAMSWVRQAPGKGLEWVSAISGSGGSTYYADSVK

GRFTISRDNSKNTLYLQMNSLRAEDTAVYYCARSHSSGGFDYWGQGTLVTVSSGGGGSGGGGSGG

GGSQSVLTQPPSVSGAPGQRVTISCTGSSSNIGRGYNVHWYQQLPGTAPKLLIYGNTNRPSGVPD

RFSGSKSGTSASLAITGLQAEDEGDYYCQSYDSSLSAWVFGGGTKLTVLG

In a preferred embodiment, said extracellular ligand-binding domain is a single chain antibody fragment (scFv) comprising the light ($V_L$) and the heavy ($V_H$) variable fragment of a target antigen specific monoclonal antibody joined by a flexible linker.

In a more preferred embodiment, said scFv is an anti-carbonic anhydrase IX scFV, preferably scFV-G36 (WO2007/065027 VH: SEQ ID NO: 1 and VL: SEQ ID NO: 2). The contents of WO2007/065027 are hereby incorporated by reference in their entirety.

Other binding domain than scFv can also be used for predefined targeting of lymphocytes, such as camelid single-domain antibody fragments or receptor ligands, antibody binding domains, antibody hypervariable loops or CDRs as non limiting examples.

In a preferred embodiment said transmembrane domain further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a cell can be a cytolytic activity or helper activity including the secretion of cytokines. Thus, the term "signal transducing domain" refers to the portion of a protein which transduces the effector signal function signal and directs the cell to perform a specialized function.

Signal transduction domain comprises two distinct classes of cytoplasmic signaling sequence, those that initiate antigen-dependent primary activation, and those that act in an antigen-independent manner to provide a secondary or co-stimulator signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCR zeta, FcR gamma, FcR beta, FcR epsilon, CD3 gamma, CD3 delta, CD3 epsilon, CD5, CD22, CD79a, CD79b and CD66d. In a preferred embodiment, the signaling transducing domain of the CAR can comprise the CD3 zeta signaling domain, or the intracytoplasmic domain of the Fc epsilon. R1 beta or gamma chains. In another preferred embodiment, the signaling is provided by CD3 zeta together with co-stimulation provided by CD28 and a tumor necrosis factor receptor (TNFr), such as 4-1BB or OX40, for example.

In particular embodiment the intracellular signaling domain of the CAR of the present invention comprises a co-stimulatory signal molecule. In some embodiments the intracellular signaling domain contains 2, 3, 4 or more co-stimulatory molecules in tandem. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatoty ligand (ICOS-L), intercellular adhesion molecule (ICAM, CD30L, CD40, CD70, CD83, HLA-G, MICA, MICB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-I (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to MHC class 1 molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. The In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

The term "a part of" used herein refers to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the CAR of the invention within a host cell is detectable in an assay suitable for demonstrating the signaling potential of said CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon gamma., GM-CSF, IL-3, IL-4 production thus effected.

Cells

Embodiments of the invention include cells that express a CAR. The cell may be of any kind, including an immune cell capable of expressing the CAR for cancer therapy or a cell, such as a bacterial cell, that harbors an expression vector that encodes the CAR. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T-cells or killer T cell); NK cells and NKT cells are also encompassed in the invention.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells.

In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

Introduction of Constructs into CTLs

Expression vectors that encode the CARs can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example,) can knock-out an endogenous gene and replace it (at the same locus or elsewhere) with the gene encoded for by the construct using materials and methods as are known in the art for homologous recombination. For homologous recombination, one may use either .OMEGA. or O-vectors. See, for example, Thomas and Capecchi, Cell (1987) 51, 503-512; Mansour, et al., Nature (1988) 336, 348-352; and Joyner, et al., Nature (1989) 338, 153-156.

The constructs may be introduced as a single DNA molecule encoding at least the CAR and optionally another gene, or different DNA molecules having one or more genes. Other genes include genes that encode therapeutic molecules or suicide genes, for example. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

Methods of Use

The cells according to the invention can be used for treating cancer in a patient in need thereof. In another embodiment, said isolated cell according to the invention can be used in the manufacture of a medicament for treatment of a cancer, in a patient in need thereof.

The present invention relies on methods for treating patients in need thereof, said method comprising at least one of the following steps: (a) providing a chimeric antigen receptor cells according to the invention and (b) administrating the cells to said patient.

The patient is a cancer patient or a patient susceptible to cancer or suspected of having cancer. The cancer is a CAIX expressing cancer such as renal cancer, ovarian cancer, breast cancer, esophageal cancer, bladder cancer, colon cancer, or non-small cell lung cancer. In some embodiments the renal cancer is renal clear cell cancer.

Administration of Cells

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Depending upon the nature of the cells, the cells may be introduced into a host organism, e.g. a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

In some embodiments, the cells are encapsulated to inhibit immune recognition and placed at the site of the tumor.

The cells may be administered as desired. Depending upon the response desired, the manner of administration, the life of the cells, the number of cells present, various protocols may be employed. The number of administrations will depend upon the factors described above at least in part.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaly, intratumorally, intranodally, intramedullar, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$~$10^9$ cells per kg body weight, preferably $10^5$ to $10^6$ cells/kg body weight including all integer values of cell numbers within those ranges. The cells or population of cells can be administered in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

Nucleic Acid-Based Expression Systems

The CARs of the present invention may be expressed from an expression vector. Recombinant techniques to generate such expression vectors are well known in the art.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5 prime' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR TM., in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al, 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals In certain embodiments of the invention, the use of internal ribosome entry sites (IRES) elements are used to create multigene, or polycistronic, messages, and these may be used in the invention.

Vectors can include a multiple Cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coil species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM.TM. 11 may be utilized in making a recombinant phage vector which can be used to transform host cells, such as, for example, E. coli LE392.

Further useful plasmid vectors include pIN vectors (Inouye of al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, E. coli, comprising, the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs of the invention. Non-limiting examples of virus vectors that may be used to deliver a nucleic acid of the present invention are described below.

Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996, Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,1,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Harwich et al., 1990).

Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids of the present invention. In particular aspects, the transplanted cells or tissues may be placed into an organism. In preferred facets, a nucleic acid is expressed in the transplanted cells.

Kits of the Invention

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dray powder, the powder can be reconstituted by the addition of a suitable solvent. It is envisioned that the solvent may also be provided in another container means. The kits may also comprise a second container means for containing a sterile, pharmaceutically acceptable buffer and/or other diluent.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapies. In the context of the present invention, it is contemplated that cell therapy could be used similarly in conjunction with chemotherapeutic, radiotherapeutic, or immunotherapeutic intervention, as well as pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

In specific embodiments, chemotherapy for the individual is employed in conjunction with the invention, for example before, during and/or after administration of the invention.

Radiotherapy

Other factors that cause DNA damage and have been used extensively include what are commonly known as gamma.-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described. herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include PD-1, PD-L1, CTLA4, carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mobs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, even 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatoly agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

EXAMPLES

Example 1: Materials and Methods

Cells, culture media and reagents. Human CAIX+ renal cell carcinoma cell lines sk-rc-52 (also referred to herein as Skrc52), sk-rc-09 and CAIX− sk-rc-59 (also referred to herein as Skrc59) were obtained from Dr. Gerd Ritter, Memorial Sloan-Kettering Cancer Center, New York. They were cultured at 37° C. with 5% $CO_2$ in R-10 complete medium containing RPMI 1640 medium (Life Technologies) supplemented with 10% FCS, 2 mmol/L L-glutamine, 100 U/ml penicillin, and 100 μg/ml streptomycin (Sigma). Primary human T cells were maintained in R-10 with 10% human serum and 100 IU/ml recombinant human interleukin 2 (IL-2) (Chiron). Human embryonic kidney cell line 293T (ATCC) and mouse fibroblast NIH3T3 cells (ATCC) were grown in D-10 complete medium (Life Technologies) containing DMEM medium with 10% FCS, 100 U/ml penicillin, and 100 μg/ml streptomycin (Sigma). Leukopacks obtained from the blood bank of the Children's Hospital Boston were collected from healthy volunteers with written informed consent.

scFv isolation and conversion of scFv to scFv-Fc. CAIX-specific scFv antibodies were isolated from a non-immune human scFv phage library as previously reported and submitted to GenBank with accession numbers of GQ903548-GQ903561[23], the contents of which is hereby incorporated herein by reference in their entireties. scFv-coding DNA fragments from the pFarber phagemid were digested with SfiI/NotI sites and subcloned into the mammalian expression vector pcDNA3.1-F105L-hinge-stuffer which has a human IgG1 F105 leader sequence and the human IgG1 hinge-CH2-CH3 Fc portion to express scFv-Fc antibodies. Plasmids of scFv-Fc were transiently transfected into 293T cells by lipofectamine 2000 (Invitrogen), and expressed antibodies were purified using Sepharose protein A beads (Amersham Bioscience). Specific binding to CAIX was tested by staining with phage scFv antibodies or scFv converted into scFv-Fc format antibodies by incubation with CAIX-expressing 293T and sk-rc-52 cell lines, and with CAIX negative 293T and sk-rc-59 cell lines. In these experiments, irrelevant anti-HIV CCR5 antibody (clone A8)[25] or anti- SARS antibody (11A)[24] and fluorescently conjugated secondary antibodies alone were used as negative controls.

In one embodiment, Human ccRCC cell lines, Skrc52, originally CAIX+PD-L1−, and Skrc59, originally CAIX−/PD-L1+, were obtained from Dr. Gerd Ritter (Memorial Sloan-Kettering Cancer Center, New York). These cells were cultivated in RPM 1640 Medium (Life Technologies) supplemented with 10% (v/v) heat-inactivated fetal bovine serum (FBS, Gibco™), 100 IU/ml penicillin and 10 µg/ml streptomycin. 293T (CRL-11268, ATCC) and Lenti-X 293T (Clontech) cells were grown in DMEM Medium (Life Technologies™) supplemented with 10% FBS, 100 IU/ml penicillin and 100 µg/ml streptomycin. All cell lines used in this project were transduced with luciferase through lentiviral transduction and maintained at 37° C. with 5% CO2. The Skrc52 cells were selected for CAIX−/PD-L1− and CAIX+/PD-L1− cell populations by Fluorescence activated cell sorting (FACS) sorting. Skrc59 cells were engineered to express high levels of human CAIX and CAIX+/PD-L1+ were selected by FACS sorting.

Construction of scFv-CD8-TCRζ and scFv-CD28-TCRζ constructs. Pz1, scFv-CD8-TCRζ, and P28z, scFv-CD28-TCRζ, DNA constructs in phagemid vector pSL1180 were obtained from Dr. Michel Sadelain, Memorial Sloan-Kettering Cancer Center, New York. In Pz1, the scFv and TCRζ intracellular domain are appended to N- and C-terminus of human CD8α chain, respectively. Similarly, in P28z, the scFv and TCRζ sequences are appended to the N- and C-terminus of human CD29, respectively. The amino acid sequence of human CD8α is 71 residues in length, consisting of 47 (aa 137-183), 23 (aa 184-206), and 2 (aa 207-208) residues of the CD8α extracellular and hinge, transmembrane, and cytoplasmic domains, respectively. The CD28 sequence in P28z is 107 residues in length, consisting of 40 (aa 114-153), 23 (aa 154-176), and 44 (aa 177-220) residues of the CD28 extracellular, transmembrane, and cytoplasmic domains respectively. The human CD3ζ intracellular domain common to both CARs consists of 112 amino acids (aa 52-163).

The nucleic acid sequence encoding an internal C9-tag (a nine-amino acid peptide of human rhodopsin, TETSQVAPA) with a GGGGS linker was amplified by PCR and was fused upstream with CD8-TCRζ and CD28-TCRζ sequences with 5' NotI site and 3' PacI sites. The primers used for cloning chimeric TCRζ constructs are 5' TAG GGC GCG GCC GCa acc gag acc agc cag gtg gcg ccc gcc GGG GGA GGA GGC AGC CCC ACC ACG ACG CCA GCC CCG CGA 3' (SEQ ID NO: 71) (forward primer for CD8 construct where italic is the NotI site, upper case is the C9 tag sequence, and underlining indicates the GGGGS linker), 5' TAG GGC GCG GCC GCa acc gag acc agc cag gtg gcg ccc gcc GGC GGA GGA GGC AGC ATT GAA GTT ATG TAT CCT CCT CCT 3" (SEQ ID NO: 75) (forward primer for CD28 construct) and reverse primer for both constructs CTA GCC TT AAT TAA, TTA GCG AGG AGG GGG CAG GGC CTG CAT (SEQ ID NO: 77), italic is Pac I site. These DNA fragments encoded functional features which are arranged in accordance with the following sequence: NotI-C9tag (TETSQVQPQ)-GGGGS-CD8 or CD28-TCRζ-PacI. The sequence TETSQVQPQ has SEQ ID NO: 78). The Sequence GGGGS has SEQ ID NO: 79) The chimeric TCR constructs tagged with internal C9 peptide were cloned into the pcDNA3.1-F105L-hinge stuffer vector containing anti-CXCR4 scFv-Fc, clone 48, using NotI and PacI restriction sites. This design allowed us to insert chimeric TCR receptor constructs to replace Fc portion fragment. Later, anti-CAIX scFv (clone G36) and anti-CCR5 scFv (clone A8, as irrelevant scFv control) antibody fragments were cloned to replace anti-CXCR4 scFv at SfiI/NotI sites to create CAIX-specific chimeric TCR constructs.

The lentivirus vector pHAGE-CMV-DsRed-1RES-Zs-Green, and four HIV helper plasmids pHDM-Hgpm2 (HIV gag-pol), pMD-tat, pRC/CMV-rev, and an Env VSV-G pseudotype were obtained from Dr. Richard Mulligan, of the Virus Production Core at The Harvard Gene Therapy Initiative in Boston. The CMV promoter in pHAGE-CMV-IRES-ZsGreen was replaced by an EF1α promoter derived from the pSIN lentivirus vector at SpeI/NotI sites. One of the 5 scFv-Fc antibodies, G36, which possess high affinity to CAIX+ cells and high ADCC only against CAIX+ tumor cells, was cloned into pHAGE-EE1α lentivirus vector at AscI/BamHI to replace the first cassette of the DsRed protein.

Production of lentivirus and transduction of human primary T cells. Lentivirus was produced by five plasmid transient transfection into 293T cells using lipofectamine 2000 as per the manufacturer's instructions (Invitrogen). Cells were prepared for 80% confluence in 15 cm Petri dishes (Nalge Nunc) and transfected with 30 µg of total plasmid DNA. The ratio of vector plasmids (pHDM-Hgpm2 (HIV gag-pol): pMD-tat: pRC/CMVrev: Env VSV-G pseudotype) was 20:1:1:1:2. After changing to D-10 medium, virus supernatant was harvested on day 3, filtrated through a 0.45 µm filter, and concentrated by ultracentrifugation (Beckman Coulter, Fullerton, CA) for 90 minutes at 16,500 rpm (48,960× g, Beckman SW28 rotor) and 4° C. The virus pellets were resuspended in R-10 medium and kept frozen at −80° C.

In one embodiment, Lentiviruses were produced by transient transfection of five plasmids into 293T cells using Polyethyleneimine (PEI). Briefly, each 80% confluent 293T cells in 15 cm plate (Nalge Nunc) was transfected with 30 µg of total five plasmids, being 5 µg of each structural plasmid pHDH-Hgpm2 (HIV gag-pol), pMD-tat; pRC/CMV-rev and Env VSV-G, and 10 µg of the main plasmid codifying the CAR (anti-CAIX/anti-PD-L1 IgG1, anti-CAIX/anti-PD-L1 IgG4, anti-CAIX/anti SARS IgG1 or anti-BCMA/anti SARS IgG1). The virus supernatant was concentrated using Lenti-X Concentrator (Clontech), following the manufacturer instructions, and kept frozen at −80° C.

Human PBMCs were isolated by ficoll density gradient separation and were activated with 2 µg/ml PHA (Sigma) plus 100 IU/ml human IL-2 for 4 days. The cells were infected with two or three rounds of lentivirus transduction at multiplicity of infection (MOI) of 10-20 in the presence of 10 µg/ml DEAE. Three days after transduction, transduced T cells were collected for phenotypic and functional analyses in vitro, or were expanded for in vivo experiments.

Flow cytometric analysis. Transduction efficiency of human primary T cells was assessed by expression of a reporter gene (ZsGreen). The CAIX-Fc protein was expressed from a pcDNA3.1 plasmid that encoded amino acids 38-397 of CAIX followed by human IgG1 hinge, CH12 and CH3 domains, the CAIX signal peptide (aa 1-37) was replaced with Ig leader sequence. Expression of scFv (G250) on transduced T cells was tested by staining the cells with 1 µg CAIX-Fc protein, and then APC-conjugated mouse anti-human IgG antibody (Jackson ImmunoResearch). Additionally, expression of the internal rhodopsin nonapeptide (TETSQVAPA) C9 tag of the scFv domain of TCR constructs on transduced T cells was detected by staining with 5 µg mouse 1D4 antibody followed by APC-conjugated goat anti-mouse IgG antibody (Jackson ImmunoResearch). For analysis, the subsets of human cells in culture during clonal expansion experiment were stained with fluorescence conjugated mouse anti-human antibodies (Invitrogen™) against CD3 (clone S4.1). CD4 (clone S3.5) or CD8 (clone 3B5). In all cell staining, five hundred thousand cells were stained with antibodies at recommended concentration according to company's instruction. The matched isotype control antibodies for each sample were used and the cells were analyzed using a FACSCalibur cytometer (Becton-Dickinson).

In one embodiment, transduction of 293T cells or CD8+ T cells was confirmed by FACS analysis of the anti-CAIX or anti-BCMA expression. The cells were stained with 10 µg/mL of human CAIX-Fc produced n our lab or human BCMA-mouse-Fc (AB Bioscience) and then developed with 1:250 APC-conjugated mouse anti-human IgG Ab (Southern Biotech) or goat-anti mouse IgG Ab (Biolegend), respectively. CountBright™ Absolute Counting Beads (Molecular Probes) was used for the proliferation and clonal expansion assays. All samples were analyzed with an LSR Fortessa or with a FACSCalibur (BD Bioscience) and data were analyzed using FlowJo software. To analyze the status of T cell exhaustion of the CART cells they were cultured in the presence of IL-21 50 U/mL (Peprotech™) and Dynabeads Human T Activator CD3/CD28 for five days. After this period the CART cells were co-cultured with Skrc-59 CAIX+PD-L1+ cells for 2 days in order to stimulate exhaustion, 1×106 CART cells from this assay and Tumor-infiltrating Lymphocytes (TIL) collected from the in vivo assay were stained with FITC-conjugated anti-human PD-1, PE-conjugated anti-human Tim3. PerCP/Cy5.5-conjugated anti-human Lag3 antibodies (Biolegend) and Pacific Blue-conjugated anti-human CD45 and analyzed by FACS. To verify the expression levels of CAIX and PD-L1 in the different RCC cell lineages used in this project, we used 10 µg/mL of the anti-human CAIX mAb (Clone G36), produced in our laboratory, and 10 µg/mL of the biotinylated mouse anti-human PD-L1 (Biolegend). The primary antibodies were detected using 1:250 APC-conjugated anti-human Ab and PE-conjugated avidin, respectively, and analyzed by FACS.

ADCC and cytotoxicity assay of lentivirus transduced T cells. Cytotoxicity assays were performed using the DEL-FIA EuTDA Cytotoxicity kit (Perkin Elmer™, Boston, Mass.) in accordance with the manufacturer's instructions. Briefly, target tumor cells were labeled with a fluorescent ligand (BATDA) for 30 minutes at 37° C. and 1×104 labeled cells were loaded per well in 96-well U-bottom plate. For antibody-dependent cellular cytotoxicity (ADCC) assay, a panel of anti-CAIX scFv-Fc antibodies or irrelevant scFv-Fc antibody at a concentration of 1 µg/ml or 5 µg/ml was added separately. The assay was set up with ratios of effector cells (human PBMC) to target cells (E:T) at 50:1, 25:1 and 12.5:1. For the T cell cytotoxicity assay, different ratios of effector cells (nontransduced or transduced T cells) to target cells (E:T) were prepared (100:1, 50:1 and 25:1). The culture was incubated for 4 hours in humidified 5% CO2 at 37° C. After the plate was spun for 5 minutes at 500×g, 20 µl of supernatant was transferred to a flat-bottom plate. 200 µl of Europium solution was added and the fluorescence released from the cells was read by fluorometer (Victor™, PerkinElmer™). The control for spontaneous release was prepared by culturing the labeling cells only and the control for maximum release was made by adding lysis buffer (kit provided) to the labeling cells.

ELISA, ELISPOT assays and Western blot. For cytokine secretion, RCC cell lines sk-rc-52 (CAIX+) or sk-rc-59 (CAIX−) were seeded overnight at 1×106 per well in a 24-well plate, followed by 1×106 untransduced or transduced T cells. Before coculture with tumor cells, T cells were washed with PBS twice to remove human IL-2. After overnight incubation, the supernatant was harvested and analyzed for IL-2 and IFN-γ by ELISA (e-Bioscience™). In detecting T cells for the IFN-γ ELISPOT assay (e-Bioscience™), a membrane was developed using AEC substrate solution and the number of spots was counted by ELISPOT plate reader (C.T.L. Cellular Technology).

For Western blot, preparation of untransduced and transduced T cells was described50. One million cells were prepared in non-reducing and reducing buffer (0.1 M dithiothreitol) and run on a 10-20% polyacrylamide gradient gel (Invitrogen™). Proteins were transferred to polyvinylidene fluoride transfer membrane (NEN Life Science Products, Boston, Mass.) at 100 V, 4° C. overnight. The membrane was incubated with 1:2000 primary antibody, anti-human ζ-chain monoclonal antibody 8D3 (BD Pharmingen, San Diego, Calif.) and then with 1:3000 secondary antibody horseradish peroxidase (Caltag). Immunodetection was performed using the ECL Plus Western blotting detection system (GE Healthcare, Piscataway, N.J.) and x-ray film exposure.

Proliferation, clonal expansion and cytokine secretion after tumor cell contact. Tumor cells were irradiated (3,000 rads) and seeded at $2.5 \times 10^5$ per well. T cells were added at $1 \times 10^6$ in culture medium containing R-10 plus 100 IU/ml human IL-2 for a week culture. T cells were split to maintain suitable density and re-stimulated with tumor cells weekly. The number of T cells was counted every 3 or 4 days for 2 weeks. The percentage expression of ZsGreen by transduced T cells and T cell subsets were determined weekly by fluorescence-activated cell sorting (FACS). For cytokine secretion studies after tumor cell contact, T cells that were in contact with irradiated tumor cells for one or two weeks were washed, incubated with fresh tumor cells overnight and culture supernatants were collected after 24 hrs for analysis.

Tumor establishment and T cell therapy. In one embodiment, due to immune-rejection of sk-rc-52 in 6-8 week-old female BALB/c nude mice and to accelerate in vivo growth properties, five million cells were subcutaneously inoculated into the mice, harvested, and expanded in vitro. The cell line was then passaged two more times in nude mice and the passaged cells were expanded for further experiments (subclone 4-1). For the therapeutic experiments, 5 million sk-rc-59 and 7.5 million passaged sk-rc-52 cells were subcutaneously inoculated on opposing flanks into nude mice to yield comparable tumor growth rates. After 7 days, tumors grew to the size of ~6 mm, and 50 million nontransduced or transduced T cells were injected intravenously. The mice were also treated with 20,000 IU human IL-2 by peritoneal injection every two days. Tumor size was measured by caliper in two dimensions and the mean of two tumor diameter was reported here. Animal experiments were performed in accordance with the guidelines of the Dana Farber Cancer Institute Animal Care Committee. Mice were sacrificed when tumors reached 15-mm diameter or 2,000 mm³ and tumors were harvested.

Immunohistochemistry and immunofluorescence staining. For in vitro examination of transduced T cells, the cultured T cells were washed twice using PBS and resuspended in 2µM Far Red DDAO-SE CellTrace dye (Molecular Probe) in PBS for 15 minutes at 37° C. Then the cells were washed with culture medium twice and cytospun on the glass slide. Far red pre-stained CART cells with ZsGreen coexpression were visualized using confocal microscopy (Zeiss) at the Optical Imaging Core facility, Harvard NeuroDiscovery Center.

To examine the killing effect of transduced T cells in tumor bed in situ, tumors were prepared for frozen sections for ApopTag Peroxidase In Situ Apoptosis Detection kit (Millipore). Cryosections were incubated with TdT enzyme (Millipore) for 1 hour. Rabbit anti-DIG (Dako) was added and incubated for 30 minutes and then Cy3-conjugated anti-rabbit antibody (Invitrogen) was added and incubated for 30 minutes. Sections were mounted with DAPI antifade mounting medium and fluorescent images were examined using confocal microscopy.

Xenograft tumors and mouse spleens were harvested, fixed in 10% formalin/PBS solution, and submitted to the Harvard Medical. School, Rodent Histopathology Core Facility. Paraffin-embedded sections were dewaxed with xylene and rehydrated through graded alcohols before staining. Immunohistochemistry staining was performed by incubating with anti-human granzyme B antibody (Dako, clone GrB-7 (1:200)) as a primary antibody for 1 hour followed by secondary anti-rabbit antibody (Pierce) or anti-mouse antibody (Dako) for 30 minutes. Sections were developed using DAB substrate and counterstained with hematoxylin.

In one embodiment, the fixed tumors were paraffin-embedded, sectioned at four-micrometer, placed on slides and prepared for IHQ. The tissues were stained with the anti human: Ki67 (Vector, VP-K451), PD-L1 (Clone 405.9A11, produced in Dr. Gordon Freeman's lab), granzyme B (Abcam, ab4059) or NCAM (CD56) (Abcam, ab133345) antibodies, followed by secondary HRP conjugated anti-rabbit Ab or HRP-Avidin. The slides were developed using DAB and counterstained with hematoxylin. The images were obtained in an Olympus BX51 microscopy using a DP71 digital camera (Olympus) and analyzed in the DP Controller Software (Olympus). The image quantification was performed using the IHC Profiler Plugin of ImageJ Software as described in Varghese F, Bukhari A B, Malhotra R, De A. IHC Profiler: an open source plugin for the quantitative evaluation and automated scoring of immunohistochemistry images of human tissue samples, PloS one, 2014;9:e96801.

Statistical analyses.

Statistical significance was determined using the two-tailed Student's t-test.

In one embodiment, the statistical significance of the data was evaluated using ANOVA and Tukey posttest. $P<0.05$ was considered significant. The statistical analysis was performed using the IBM SPSS Statistics software version 20.

Figure 1B:
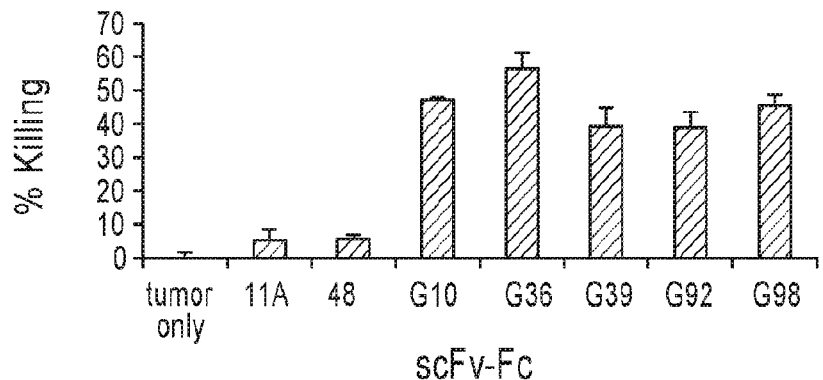
Figure 1C:

Example 2: ADCC Mediated Killing of Anti-CAIX Antibodies and Choice of CAR Targeting Moiety We have previously reported on a panel of high affinity human anti-CAIX antibodies that differed in their epitope mapping, expression levels and ability to internalize CAIX[23]. Our first aim was to investigate the anti-tumor activity of five of these anti-CAIX single-chain antibodies as candidates for CAR construction. To test for anti-CAIX mAb mediated ADCC, the scFvs were converted to scFv-Fc (hIgG1) minibodies[23]. We found that all scFv-Fcs exhibited antigen-specific tumor lysis. For tumor cell line sk-rc-09 with high CAIX+ expression, specific lysis ranged from 40-57% and for sk-rc-52 with moderate CAIX+ expression, specific lysis ranged from 46-60%, with background of lysis of <5% for the CAIXp– tumor cell line sk-rc-59. For negative control scFv-Fcs such as anti-CXCR4 48-Fc[23] and anti-SARS 11A-Fc[24], only background levels of cell lysis were seen (FIG. 1). Based on ADCC killing and other published analyses, scFvG36 was chosen for further evaluation as the CAR targeting moiety.

Figure 2A:
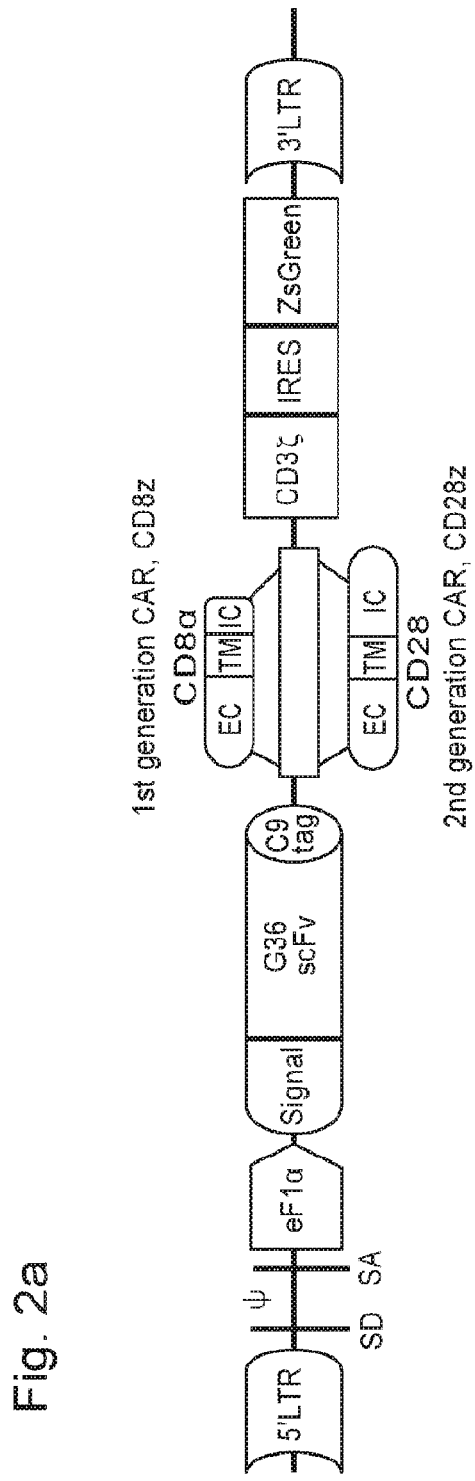
FIG. 2A-2C. Construction and expression of CAIX-specific CARs.

Construction and expression of CAIX-specific chimeric receptors. Two generations of anti-CAIX CARs were constructed: $1^{st}$ generation G36 CD8 CAR, with scFvG36 linked to CD8, truncated extracellular, hinge, and transmembrane domains plus signaling domain of TCRζ (G36-CD8z). To deliver costimulatory signals, $2^{nd}$ generation CD28 CAR was generated, consisting of scFvG36 fused to truncated extracellular, transmembrane and intracellular domains of CD28 plus signaling domain of TCRζ (G36-CD28z) (FIG. 2A). Irrelevant $2^{nd}$ generation CD28 CAR was made by using anti-HIV CCR5 (clone A8) scFv instead[25]. In order to detect the expression of these constructs, human rhodopsin C9 tag were inserted between the scFv and CD8 or CD28 domains, respectively and ZsGreen was expressed after the IRES sequence. High concentrations of viral stocks were obtained at comparable levels among the different constructs that were tested by cotransfection of vector plasmids into 293T cells (data not shown).

Figure 2B:
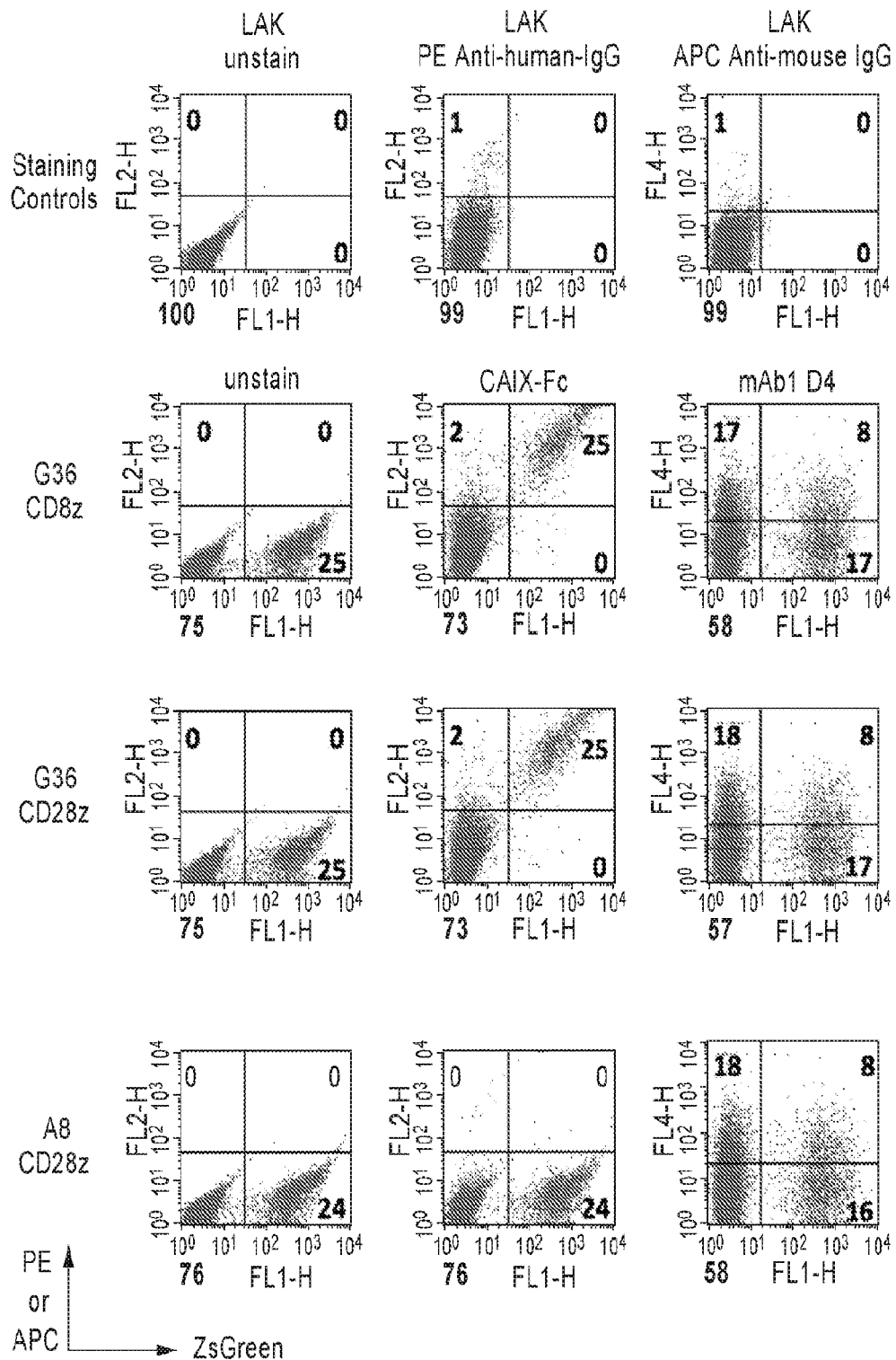

For transduction, PHA mitogen was used to stimulate peripheral blood lymphocytes for 3 days. Concentrated lentivirus supernatants were used to infect human primary T cells in the presence of cationic reagent DEAE as it increased the transduction rate of 1.5-2× fold as compared with polybrene (data not shown). The transduction rate of priinary T cells ranged from 17% to 45% by ZsGreen expression in FACS analysis. A representative experiment showing ZsGreen expression in circa 25% by primary CART cells following lentivirus transduction is shown in FIG. 2B, left column. CAIX-Fc fusion protein can bind to the G36-CD8z and -CD28z CART cells but not to control A8-CD28z CART cells (FIG. 2B, middle column). C9-tag expression was only detected at circa one-third the level of the CAIX-Fc protein (FIG. 2B, right column) which is likely related to the finding that mAb 1D4 preferentially recognizes the rhodopsin nonapeptide C9 when presented as a carboxy-terminal verses internal polypeptide sequence (data not shown). Transduced cells that were cultured in vitro for 6 weeks maintained their expression of ZsGreen.

Figure 2C:
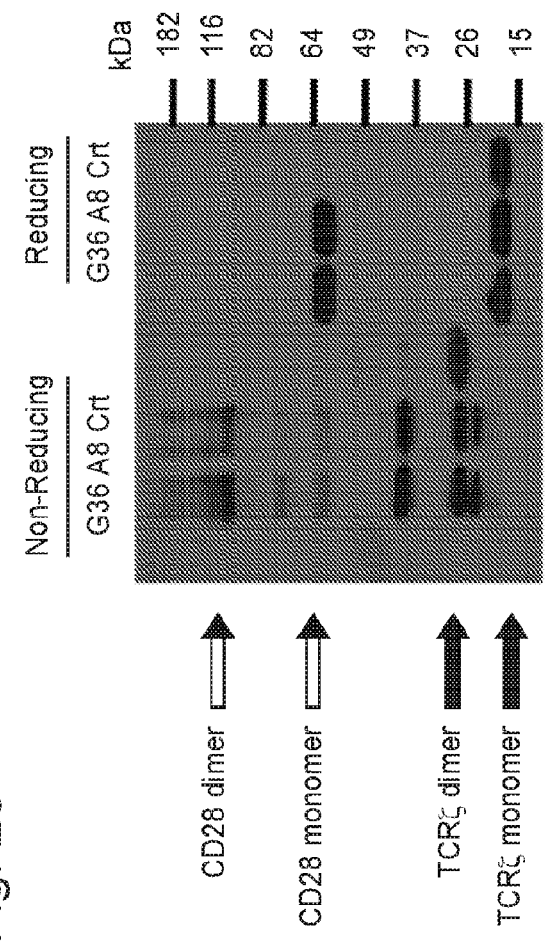

On Western blot under reducing conditions, G36 and A8 CD28z CARs migrated with a mol wt of circa 53 kD whereas endogenous TCRζ was 16 kDa. G36-CD8z CAR migrated with a mol wt of circa 48 kD. Under nonreducing conditions, these two CD28z CARs formed homodimers (FIG. 2C, data of CD8z CAR not shown).

Figure 3A:
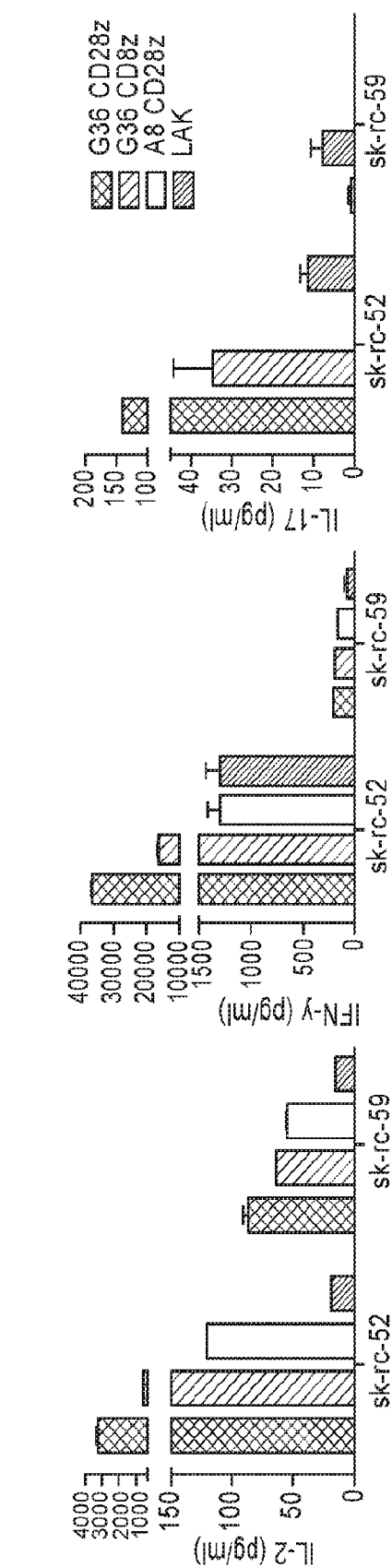

Example 3: Enhanced Cytokine Secretion by Transduced T Cells on Contact with CAIX+ Tumor A study was performed to compare the reported superior effects of using $2^{nd}$ generation G36-CD28z CART cells that incorporate signaling components of the costimulatory molecule CD28 to bypass MHC presentation and enhance T cell effector functions verses $1^{st}$ generation G36-CD8z CART cells. As seen in FIG. 3A, after incubation with CAIX+ sk-rc-52 cells overnight, only low levels of type I cytokines IL-2, IFNγ and IL-17 secretion were seen with control A8 CD28z CART cells or LAK cells alone. In contrast, both $1^{st}$ and $2^{nd}$ generation G36 expressing CART cells showed elevated levels of cytokine secretion with $2^{nd}$ generation G36-CD28z CART cells secreting higher amounts of type I cytokines which reflects their higher activation status compared to $1^{st}$ generation G36-CD8z CART cells. Specifically, G36-CD28z CART cells secreted 6.5×, 2.3× and 4× more IL-2, IFNγ and IL-17, respectively than G36-CD8z CART cells. Specificity of cytokine secretion induction by the two G36 CART cells is seen by their minimal stimulation with CAIX− sk-rc-59 cells.

In an Elispot study, after interaction with CAIX+ sk-rc-52 tumors, G36-CD28z CART cells became high capacity IFN-γ producing cells (FIG. 3B). G36-CD28z CART cells produced 6 times more spots than seen for G36-CD8z CART cells upon interaction with CAIX+ sk-rc 52 tumor cells and 12 times more spots than seen after interaction with CAIX− sk-rc-59 tumor cells. Similarly, G36-CD28z CART cells had a higher amount of granzyme B-secreting spots after contact with CAIX+ tumors as compared with G36-CD8z CART cells and control T cells. PMA and ionomycin stimulated T cells yielded the highest amount of IFN-γ and granzyme B secreting T cells. These studies demonstrate both specificity and high capacity of G36-CD28z CART cells to be activated by contact with CAIX+ tumor cells.

Example 4: Specific Cytotoxicity via CAR Signaling in Transduced T Cells

An in vitro cytotomcity assay was established to further evaluate the killing activity of the different G36 CART cells. Using different ratios of effector-to-target, G36-CD28z CART cells and its' twice in vivo passaged subclone 4-1 exhibited the highest amount of cytolysis of CAIX+ tumor sk-rc-52 (FIG. 3C). With high ratio of more than 25:1, G36-CD28z CART cells showed 2-3 fold higher cytotoxicity than G36-CD8z CART cells and with low ratio of 5:1, G36-CD28z CART cells showed 8-9 fold higher lysis than G36-CD8z CART cells. However, G36-CD8z CART cells still exhibited good cytotoxicity with up to more than 60% tumor lysis using 1.00:1 of E:T ratio. Irrelevant A8-CD28z CART cells and control T cell LAK showed the background non-specific tumor lysis with around 20% lysis when using the highest 100:1 of E:T ratio. In all cases of using CAIX− tumor sk-rc-59, transduced and untransduced T cells showed background lysis.

Figure 4A:
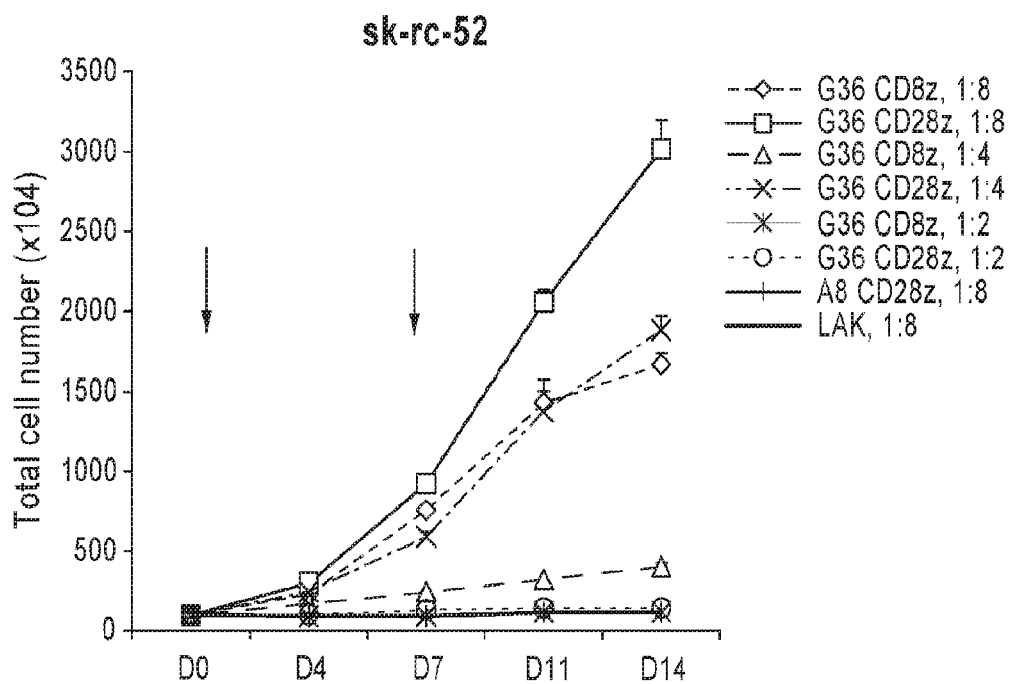
Figure 4A:
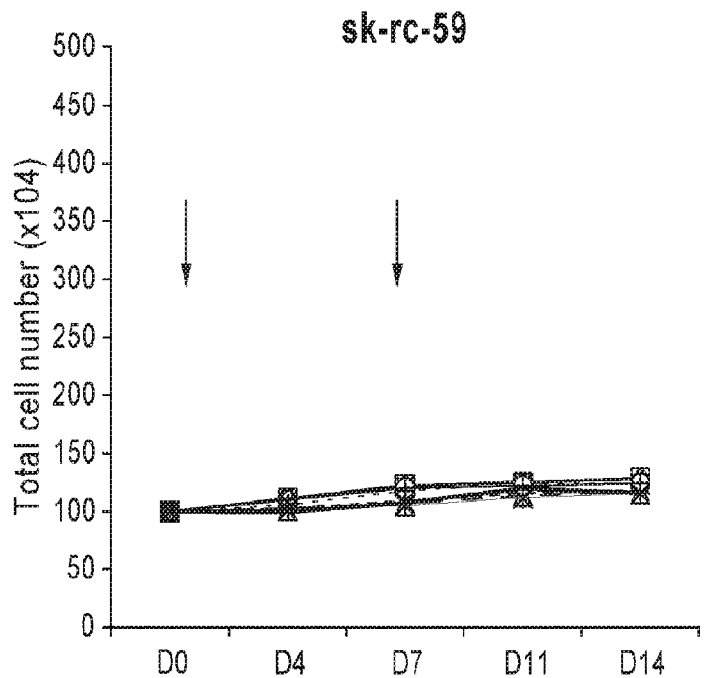

Example 5: Improved in vitro Proliferation in CART Cells With Prolonged CAIX+ Tumor Besides enhanced cytokine secretion and cytotoxicity on short term CAIX+ tumor cell contact, incorporation of the CD28 costimulatory molecule into the CAR construct demonstrated improved proliferation upon prolonged contact with antigen-specific tumor cells. Untransduced and transduced (around 20%) cells were mixed with freshly irradiated tumor cells weekly in the presence of 100 units/ml human IL-2. To test the different levels of antigen stimulation to a fixed amount of T cells, we used tumor cell to T cell ratios of 1:8, 1:4 and 1:2. T cell numbers were counted by trypan exclusion and CART cell fractions were examined by flow cytometry. Under culture with CAIX− sk-rc-59 tumor cells, the number of transduced and untransduced T cells as maintained (FIG. 4A bottom). The lack of basal level of proliferation of control T cells might be due to the high amount of suppressive cytokines secreted by the tumor cell line. In contrast. after two weeks of culture with CAIX+ sk-rc-52 tumor cells, at ratio 1:8, the population of G36-CD28z CART cells increased to 30-fold and G36-CD8z CART cells proliferated up to 17-fold whereas at a ratio of 1:4, the number of G36-CD28z CART cells increased 19-fold and G36-CD8z CART cells proliferated 4-fold. With higher amounts of tumor cells, neither G36-CD28z or G36-CD8z CART cells could proliferate. Irrelevant A8-CD28z CART cells and control T cell LAK showed no proliferation with tumor cells (FIG. 4A top).

Proliferating T cells were also harvested to examine their enrichment on CAIX+ tumor cell contact. On CAIX− tumor contact, there was no change in the percentage of any CART cells within the population. However on contact with CAIX+ sk-rc-52 tumor cells, there was enrichment in both populations of G36 CART cells. For G36-CD28z CART cells, the positive population was enriched from 18% on day 0 to 52% on day 8 to 88% on day 16. Expression of G36-CD8z CART cells was enriched from 19% on day 0 (same levels at T cells only) to 32% on day 8, and to 72% on day 16. No expansion of A8-CD28z CART cells was seen over the two week study (FIG. 4B). The percentage of CD8 cells remained constant throughout the 16 day study under all conditions (FIG. 4C).

Example 6: Persistent Effector Function of CART Cells After Re-Contact with Tumor Transduced T cells that were in contact with irradiated tumor cells for one or two weeks were also tested for cytokine secretion after 24 hours of contact with fresh non-irradiated tumor cells. Upon contact with CAIX+ tumor (sk-rc-52) for one or two weeks, G36-CD28z and G36-CD8z CART cells showed similar IFN-γ secretion levels although costimulatory signaling through G36-CD28z CAR yielding 2× to 2.5× more IFN-γ secretion than seen for G36-CD8z CAR (Table 1). For IL-2 secretion, two weeks of tumor contact for G36-CD28z and G36-CD8z CART cells exhibited more IL-2 secretion than one week of contact. G36-CD28z CART cells yielding 5× more IL2 than G36-CD8z CART cell on one week of contact and 2.5× more on contact for two weeks. In addition, G36-CD28z CART cells in contact with tumor cells for two weeks secreted 3.3× more IL-2 than one time tumor contact whereas G36-CD8z CART gave 6.8× more IL-2 secretion after two weeks compared to after one week of tumor contact. These results indicate that the transduced CART cells did not become exhausted and maintained functional activity after a second tumor stimulation. Only background levels of INF-γ and IL-2 secretion were seen with A8-CD28z, LAK and G36 CART cell treatments on contact with CAIX− sk-rc59 cells.

Example 7: Suppression of Established Tumor by CART Cells

We next tested CART cells to inhibit established tumor cell growth in nude mice that were inoculated with sk-rc-52 tumor cells on left flank and sk-rc-59 tumor cells on right flank that had been established to yield similar tumor curves. On day 7 after tumor implantation, with typical tumor size of ~6×6 mm, 50 million G36-CD28z CART cells. A8-CD28z CART cell or untransduced T cells (LAK) were injected intravenously. Adoptive T-cell therapy was performed in two separate experiments with group sizes of n=7 in the first trial and n=8 in the second trial, in the presence of high dose IL-2 ($2\times10^5$ IU) via intraperitoneal injection. No T-cell treatment was included in order to compare the growth of tumor and the effect of cell-therapy.

Figure 5:
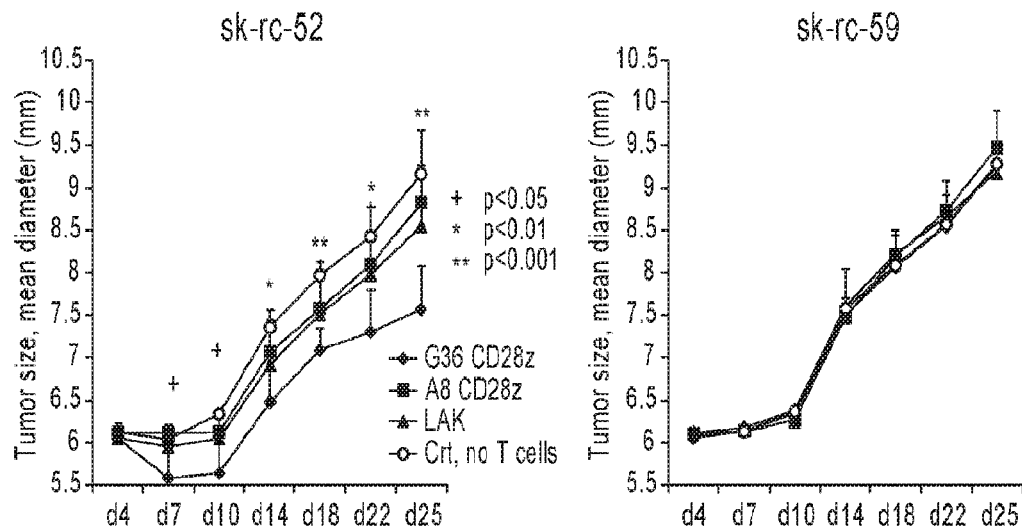
FIG. 5. Regression of established human RCC xenografts by CART cells. Athymic null mice were inoculated subcutaneously with 7.5×106 sk-rc-52 and 5×106 sk-rc-59 RCC tumor cells at left and right flank respectively. After 6 days of tumor implantation, mice were injected i.v. with 50×106 G36 CD28 CART cells, A8 CD28 CART cells (≥20% CAR+), LAK, or PBS alone. High dose of IL-2 (1×105 U/ml) was injected every 2-3 days. Tumor size was measured by caliper every 2-3 days. Experiment 1, n=7 & Experiment 2, n=8. Tumor size of these two experiments was shown separately, +, p<0.05; *,p<0.01; **,p<0.001 in groups of G36 Tandem treated mice versus control no T cell treated mice in these two trials. Other statistic calculations are reported in the text.
Figure 5:
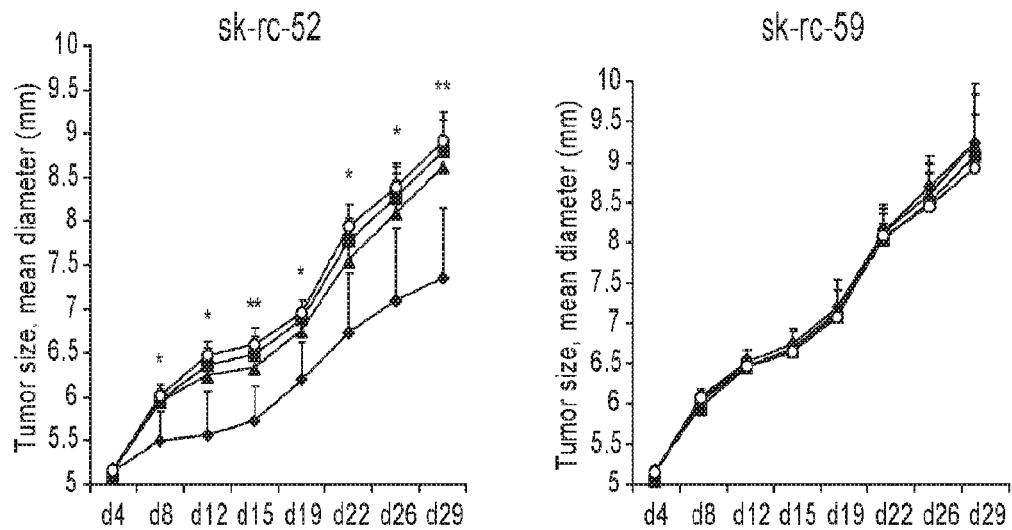

In trial one, treated and untreated CAIX− sk-rc-59 tumors had average size of 6.09±0.02 mm on day 4 and 9.29±0.12 mm on day 25 (within four tested groups). They exhibited the same tumor growth rate in control groups and T-cell treated groups. Untreated CAIX+ tumors that received no T cells showed similar tumor size as CAIX− tumors, with an average size of 6.09±0.13 mm on day 4 and 9.15±0.11 mm on day 25. However, the tumor size of G36-CD28z CART cell treated mice showed statistically significant reduction in size compared to no T-cell treated mice at every time point that was examined over the 25 day study (FIG. 5). G36-CD28z CART treatment also led to a greater reduction in tumor size than seen with A8-CD28z CART cell and LAK treated mice on day 7 (p<0.05) and on day 25 (p<0.001), as calculated by two-tailed t test. In trial two, tumor size of G36-CD28z CART cell treated mice was significant smaller than that of no T-cell treated mice through the 29 day experiment. G36-CD28z CART cell treated mice also had smaller tumors than were seen with A8 CD28z CART cell and LAK treated mice on day 8 to day 26 with p<0.01 and on day 29 with p<0.001 (FIG. 5).

Partial regression of CAIX+ tumor was considered when the tumor size was smaller than 30% volume of control CAIX− tumor in a same mouse receiving the same T-cell. Partial tumor regression was observed in a high percentage of cases using G36-CD28z CART cells (10 out of 15, (67%)), but only infrequently in irrelevant target A8-CD28z CART cells (1 out of 15, (7%)) and in activated T cell LAKs (2 out of 15, (13%)) (Table 2). Frequency of partial regression response was found to be statistically significant for mice treated with G36-CD28z CART cells versus control A8-CD28z CART cells and LAKs at p<0.001 and p<0.005, respectively by Fisher test.

Example 8: In Situ Cytotoxicity by CART Cells

A sample of the whole population of transduced T cells used for the in vivo study were pre-stained with Far red dye and the CART cells expressing ZsGreen protein within the population were analyzed by confocal microscopy. These results demonstrated circa 30% transduction efficiency which is in agreement with our FACS analysis (FIG. 6A).

Figure 6B:
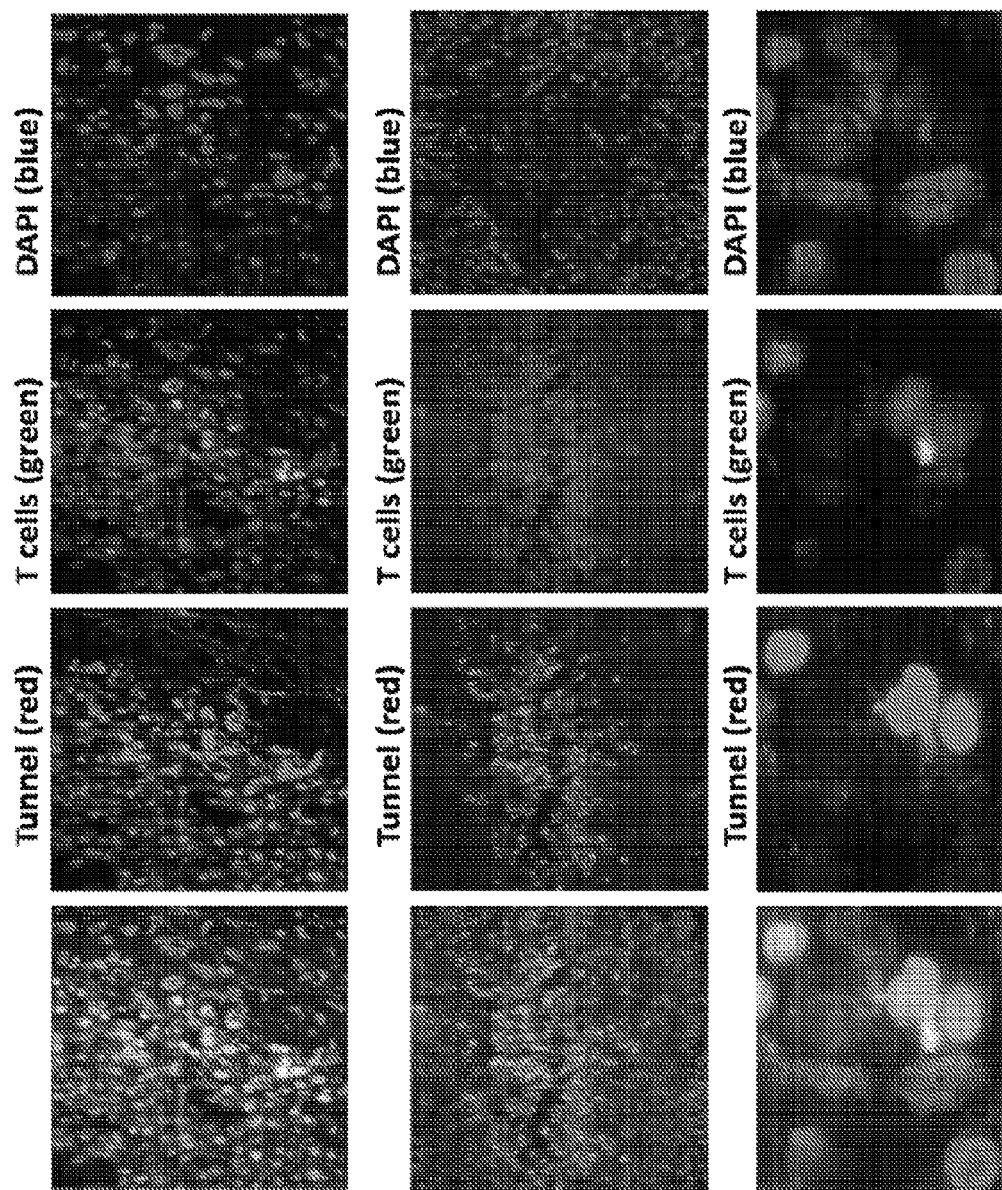

To provide evidence that G36-CD28z CART cell treatment of CAIX+ sk-rc-52 tumor cells in vivo resulted in killing by apoptosis, tumor sections were stained by Tunnel assay. On day 3 after adoptive T cell treatment, Tunnel staining identified apoptotic tumor cells (red) at the edge of tumor (FIG. 6B upper row) and inside the tumor bed (FIG. 6B middle row). The apoptotic tumor cells lost the DAPI nuclear staining. Shown in the enlarged graph (FIG. 6B bottom row) is a ZsGreen expressing CART cell interacting with two tumor cells that were going apoptosis.

Figure 6C:
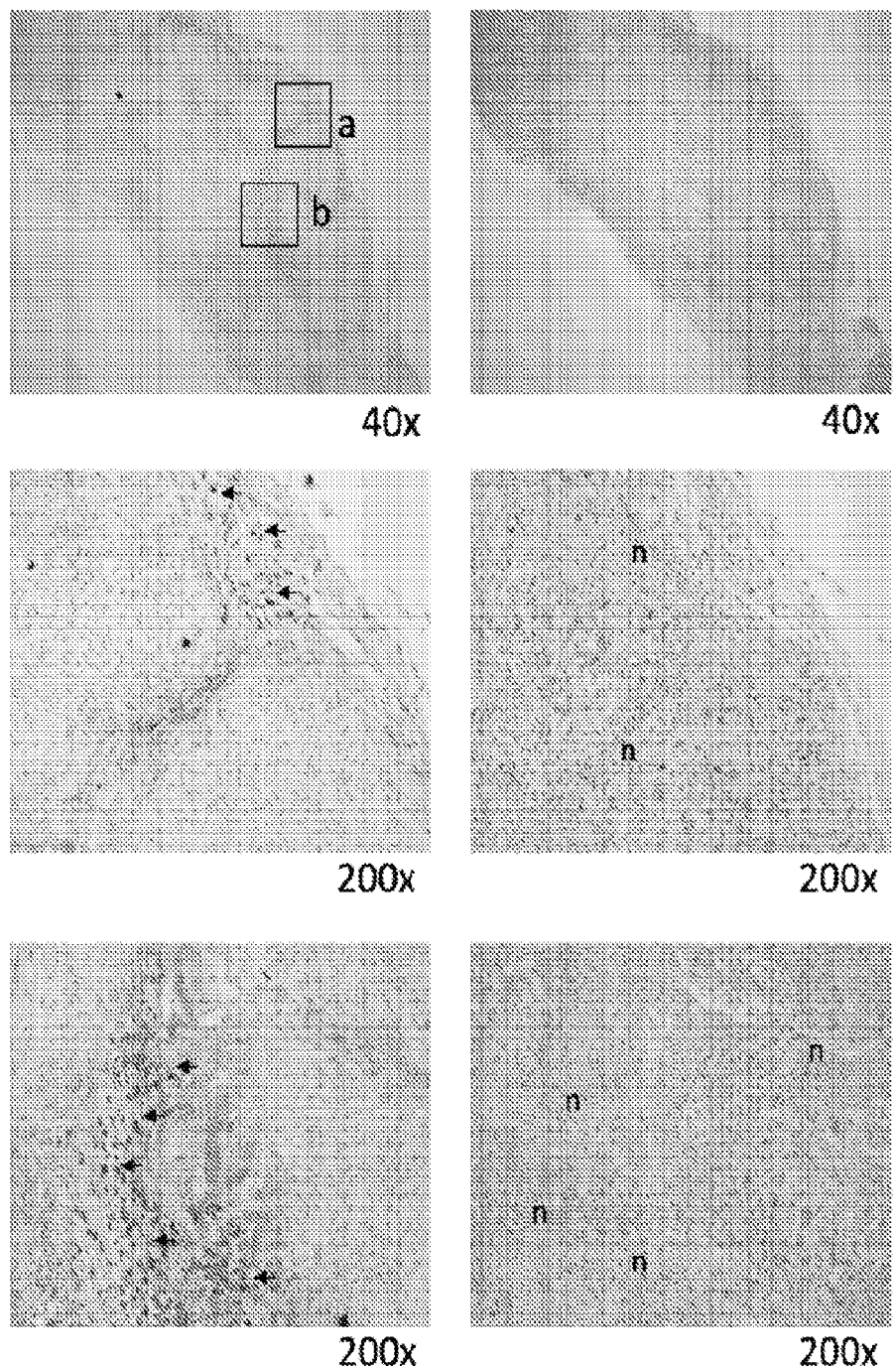
Figure 7:
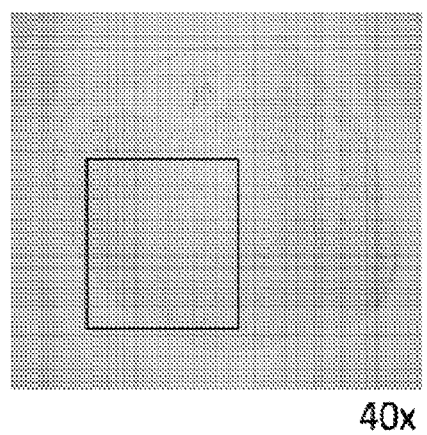
FIG. 7. CAIX-sk-rc-52 tumors treated with control LAK cells showed negative granzyme B staining (left) (upper panel) and the corresponding histology was shown in H&E (right).
Figure 7:
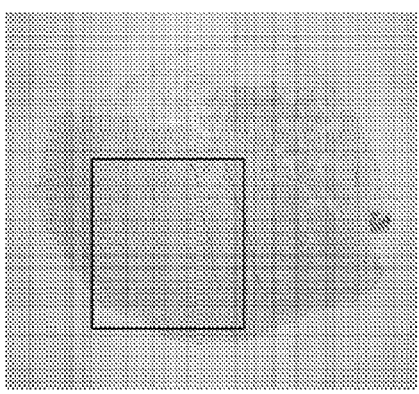
Figure 7:
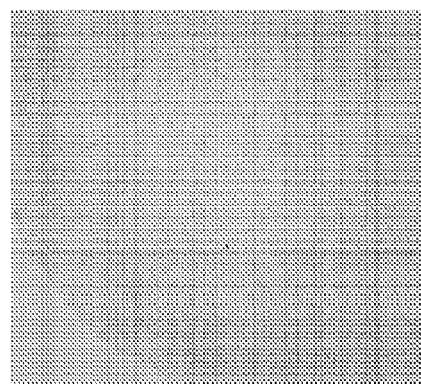
Figure 7:
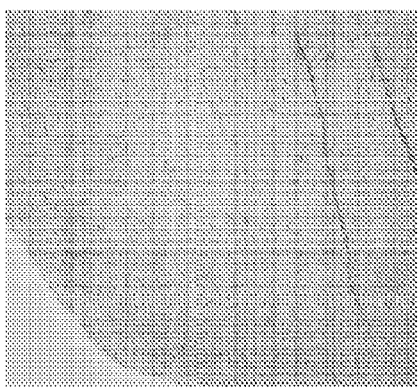
Figure 8:
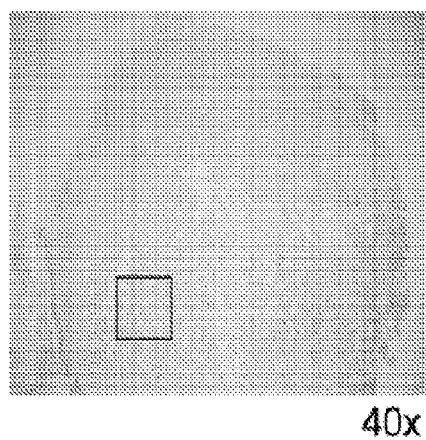
FIG. 8. Low background staining of granzyme B in CAIX− sk-rc-59 tumors treated with G36 CD28z CART cells FIG. 9. Low background staining of granzyme B in CAIX− sk-rc-59 tumors treated with LAK cells.
Figure 8:
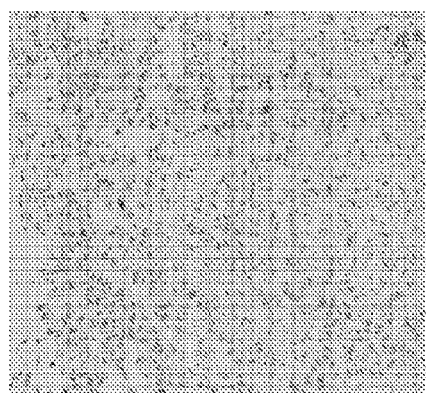
Figure 9:
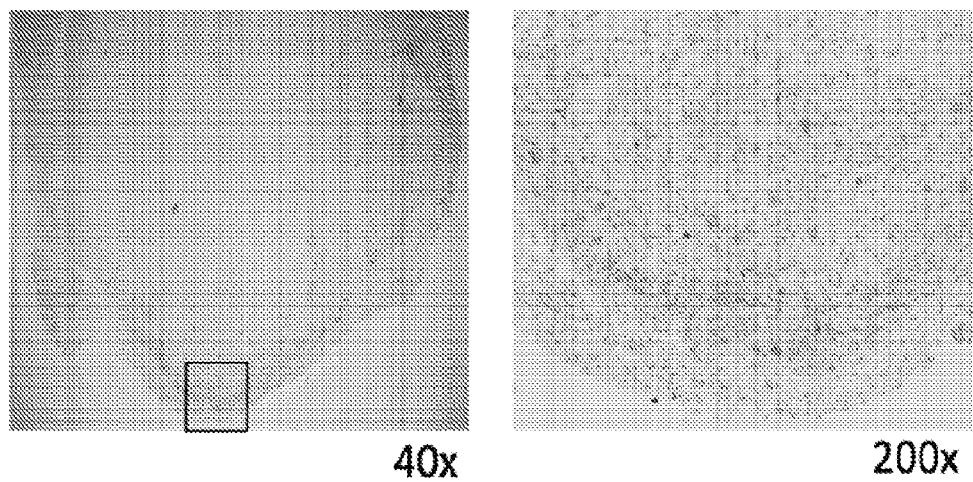
Figure 10:
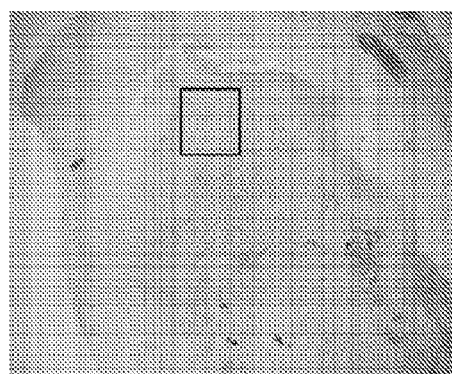
FIG. 10. Positive control of granzyme B staining was performed on sk-rc-52 tumors which was local injected with G36 CD28z CART cells (left) and tumor morphology was shown in H&E (right).
Figure 10:
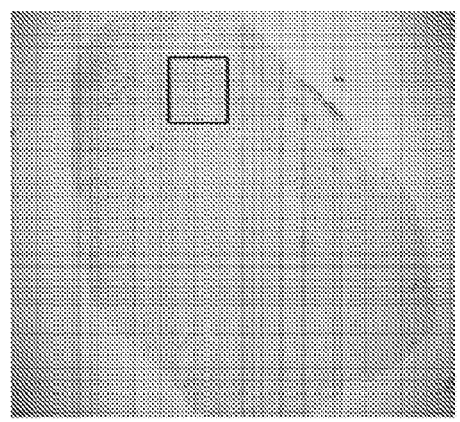
Figure 10:
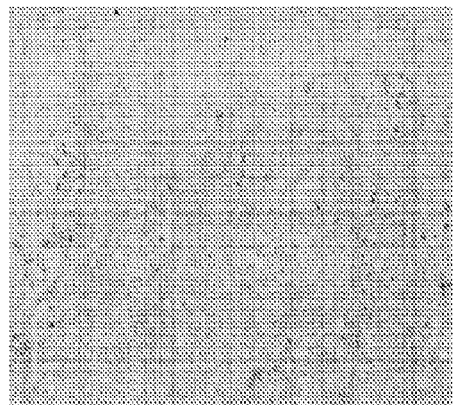
Figure 10:
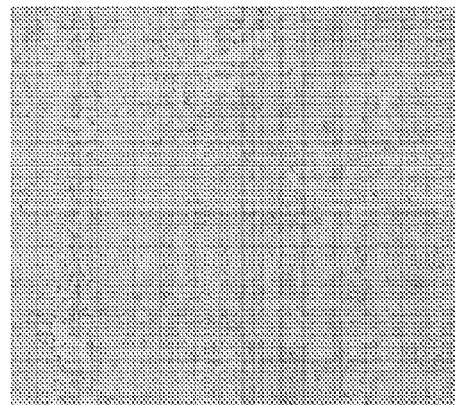

Due to the limitation of fluorescent signal, ZsGreen expressing CART cells could not be observed from the whole tissue section. Therefore on day 3 after G36-CD28z CART cell or LAK treatment, the tumors were harvested and sections were also stained with granzyme B antibody to locate the activated T cells. In FIG. 6C, the dark brown areas of staining show granzyme B+ T cells that are seen infiltrating into the CAIX+ sk-rc-52 tumor sections (FIG. 6C upper left). These granzyme B+ T cells were seen surrounding the tumor (FIG. 6C upper left (a) and middle) and inside the tumor (FIG. 6C upper left (b) and lower). Tumors with necrotic areas were shown in H&E stained slides (labeled as n inside FIG. 6C right middle and lower) and lie at locations near to the granzyme B+ T cells. In contrast, the CAIX+ sk-rc-52 tumors treated with control activated T cells (LAK) (FIG. 7) did not show any granzyme B+ T cells. Similarly, CAIX− sk-rc-59 treated with G36-CD28z CART cells (FIG. 8) or treated with LAK (FIG. 9) showed a low background staining while tumor was proliferating. For positive control of granzyme B staining, CART cells was locally injected into the established sk-rc-52 tumor in mice. After one day, the mice was sacrificed and tumor tissue was sectioned for this staining (FIG. 10).

TABLE 1

Cytokine Secretion After One or Two Weeks of Contact with Tumor Cells*

| CART cells | IFN-γ (pg/ml) | | IL-2 (pg/ml) | |
|---|---|---|---|---|
| | One week | Two weeks | One week | Two weeks |
| RC-SK-52 (CAIX+) Cells | | | | |
| G36-CD28z | 25,788 | 28,192 | 7,524 | 24,937 |
| G36-CD8z | 13,096 | 10,961 | 1,470 | 10,029 |
| A8-CD28z | 55 | 55 | 9 | 13 |
| LAK | 68 | 58 | 9 | 13 |
| RC-SK-59 (CAIX−) Cells | | | | |
| G36-CD28z | 31 | 29 | 5 | 4 |
| G36-CD8z | 27 | 38 | 8 | 10 |
| A8CD28z | 56 | 55 | 7 | 8 |
| LAK | 49 | 56 | 10 | 8 |

*Transduced T cells were incubated with irradiated tumor cells for one or two weeks then harvested, washed and incubated with fresh non-irradiated tumor cells overnight and supernatants collected after 24 hrs for cytokine analysis. For T cell cultures that did not interact with tumor cells, only background level of cytokines were detected at levels <50 pg/ml IFN-γ and <10 pg/ml IL-2.

TABLE 2

Frequency of Partial Regression of CAIX+ Tumors by G36-CD28z CART cells

| Gene construct | LAK | A8-CD28z | G36-CD28z | Statistics |
|---|---|---|---|---|
| Target antigen | none | irrelevant | specific | |
| Co-stimulatory | none | 2 signals | 2 signals | |
| Partial response | 2 | 1 | 10 | p < 0.005*; p < 0.001** |
| Non-partial response | 13 | 14 | 5 | N.S. |

Mice from experiments reported in FIG. 5 (experiment 1, n = 7 & experiment 2, n = 8) were scored for response at day 10. Partial response is defined as the regression of tumor to smaller than 30% volume of control tumor (same T-cell treatment in the same mouse bearing left flank of sk-rc-52 and right flank of control tumor sk-rc-59).
Fisher test results -
*G36-CD28z verses LAK;
**G36-CD28z verses A8-CD28z;
N.S.—no statistically significant relationship between number of tumors and partial response between T cells transduced with LAK and with A8-CD28z.

REFERENCES

1. Ivanov S, Liao S Y, Ivanova A, Danilkovitch-Miagkova A, Tarasova N, Weirich G et al Expression of hypoxia-inducible cell-surface transmembrane carbonic anhydrases in human cancer. *Am J Pathol* 2001; 158(3): 905-19.
2. Loncaster J A, Harris A L, Davidson S E, Logue J P, Hunter R D, Wycoff C C et al. Carbonic anhydrase (CA IX) expression, a potential new intrinsic marker of hypoxia: correlations with tumor oxygen :measurements and prognosis in locally advanced carcinoma of the cervix. *Cancer research* 2001; 61(17): 6394-9.
3. Hilvo M, Baranauskiene L, Salzano A M, Scaloni A, Matulis D, Innocenti A et al. Biochemical characterization of CAIX, one of the most active carbonic anhydrase isozymes. *J Biol Chem* 2008; 283(41): 27799-809.
4. Oosterwijk E, Ruiter D J, Hoedemaeker P J, Pauwels E K, Jonas U, Zwartendijk J et al. Monoclonal antibody G 250 recognizes a determinant present in renal-cell carcinoma and absent from normal kidney. International journal of cancer. *Journal international du cancer* 1986; 38(4): 489-94.

5. Liao S Y, Brewer C, Zavada J, Pastorek J, Pastorekova S, Marietta A et al. Identification of the MN antigen as a diagnostic biomarker of cervical intraepithelial squamous and glandular neoplasia and cervical carcinomas. *Am J Pathol* 1994; 145(3): 598-609.

6. Liao S Y, Aurelio O N, Jan K, Zavada J, Stanbridge E J. Identification of the MN/CA9 protein as a reliable diagnostic biomarker of clear cell carcinoma of the kidney. *Cancer research* 1997; 57(14): 2827-31.

7. Atkins M, Regan M, McDermott D, Mier J, Stanbridge E, Youmans A et al. Carbonic anhydrase IX expression predicts outcome of interleukin 2 therapy for renal cancer. *Clin Cancer Res* 2005; 11(10): 3714-21.

8. Lokich J. Spontaneous regression of metastatic renal cancer. Case report and literature reveiw. *Am J Clin Oncol* 1997; 20(4): 416-8.

9. Chaang A E, Li Q, Jiang G, Sayre D M, Braun T M, Redman B G, Phase II trial of autologous tumor vaccination, anti-CD3-activated vaccine-primed lymphocytes, and interleukin-2 in stage IV renal cell cancer. *J Clin Oncol* 2003; 21(5): 884-90.

10. Dudley M E, Wunderlich J R, Robbins P F, Yang J C, Hwu P, Schwartzentruber D J et al. Cancer regression and autoimmunity in patients after clonal repopulation with antitumor lymphocytes. *Science* 2002; 298(5594): 850-4.

11. Schaft N, Willemsen R A, de Vries J, Lankiewicz B, Essers B W, Gratama J W et al. Peptide fine specificity of anti-glycoprotein 100 CTL is preserved following transfer of engineered TcR alpha beta genes into primary human T lymphocytes. *J Immunol* 2003; 170(4), 2186-94.

12. Bubenik J. MHC class I down-regulation: tumour escape from immune surveillance? (review). *International journal of oncology* 2004; 25(2): 487-91.

13. Gajewski T F, Meng Y, Blank C, Brown I, Kacha A, Kline J et al. Immune resistance orchestrated by the tumor microenvironment. *Immunological reviews* 2006; 213: 131-45.

14. Frigola X, Inman B A, Lobse C M, Krco C J, Cheville J C, Thompson R H et al. Identification of a soluble form of B7-H1 that retains immunosuppressive activity and is associated with aggressive renal cell carcinoma. *Clin Cancer Res* 2011; 17(7): 1915-23.

15. Grepin R. Guyot M, Giuliano S, Boncompagni M, Ambrosetti D, Chamorey E et al. The CXCL7/CXCR1/2 axis is a key driver in the growth of clear cell renal cell carcinoma. *Cancer research* 2014; 74(3): 873-83.

16. Sadelain M, Brentjens R, Riviere I. The promise and potential pitfalls of chimeric antigen receptors, *Curr Opin Immunol* 2009; 21(2): 215-23.

17. Lamers C H, Sleijfer S, van Steenbergen S, van Elzakker P, van Krimpen B, Groot C et al. Treatment of metastatic renal cell carcinoma with CAIX CAR-engineered T cells: clinical evaluation and management of on-target toxicity. *Molecular therapy: the journal of the American Society of Gene Therapy* 2013; 21(4): 904-12.

18. Milone M C, Fish J D, Carpenito C, Carroll R G, Binder G K, Teachey D et al. Chimeric receptors containing CD137 signal transduction domains mediate enhanced survival of T cells and increased antileukemic efficacy in vivo. *Molecular therapy: the journal of the American Society of Gene Therapy* 2009; 17(5): 1453-64.

19. Wilkie S, Picco G, Foster J, Davies D M. Julien S, Cooper L et al. Retargeting of human T cells to tumor-associated MUC1: the evolution of a chimeric antigen receptor. *J Immunol* 2008; 180(7): 4901-9.

20. Lo A S, Ma Q, Litt D L, Junghans R P. Anti-GD3 chimeric sFv-CD28/T-cell receptor zeta designer T cells for treatment of metastatic melanoma and other neuroectodermal tumors. *Clin Cancer Res* 2010; 16(10): 2769-80.

21. Kalos M, Levine B L, Porter D L, Katz S. Grupp S A, Bagg A et al. T cells with chimeric antigen receptors have potent antitumor effects and can establish memory in patients with advanced leukemia. *Science translation medicine* 2011; 3(95): 95ra73.

22. Pegram H J, Park J H, Brentjens R J. CD28z CARs and armored CARs. *Cancer J* 2014, 20(2): 127-33.

23. xu C, Lo A, Yammanuru A, Tallarico A S, Brady K, Murakami A et al. Unique biological properties of catalytic domain directed human anti-CAIX antibodies discovered through phage-display technology. *PLoS one* 2010; 5(3): e9625.

24. Sui J, Aird D R, Tamin A. Murakami A, Yan M. Yammanuru A et al. Broadening of neutralization activity to directly block a dominant antibody-driven SARS-coronavirus evolution pathway. *PLoS pathogens* 2008: 4(11): e1000197.

25. Mirzabekov T, Kontos H, Farzan M, Marasco W, Sodroski J. Paramagnetic proteoliposomes containing a pure, native, and oriented seven-transmembrane segment protein, CCR5. *Nat Biotechnol* 2000; 18(6): 649-54.

26. Wald O, Weiss I D, Wald H, Shoham H, Bar-Shavit Y, Beider K et al. IFN-gamma acts on T cells to induce NK cell mobilization and accumulation in target organs. *J Immunol* 2006: 176(8): 4716-29.

27. Zeytin H, Reali E, Zaharoff D A, Rogers C J, Schlom J, Greiner J W. Targeted delivery of murine IFN-gamma using a recombinant fowlpox virus: NK cell recruitment to regional lymph nodes and priming of tumor-specific host immunity. *Journal of interferon & cytokine research: the official journal of the International Society for Interferon and Cytokine Research* 2008; 28(2): 73-87.

28. Murugaiyan G, Saha B. Protumor vs antitumor functions of IL-17. *J. Immunol* 2009; 183(7): 4169-75.

29. Bar E, Whitney P G, Moor K, Reis e Sousa C, LeibundGut-Landmann S. IL-17 regulates systemic fungal immunity by controlling the functional competence of NK cells. *Immunity* 2014; 40(1): 117-27.

30. Hinrichs C S, Kaiser A. Paulos C M, Cassard L, Sanchez-Perez L, Heemskerk B et al. Type 17 CD8+ T cells display enhanced antitumor immunity. *Blood* 2009; 114(3): 596-9.

31. Hombach A A, Rappl G, Abken H. Arming cytokine-induced killer cells with chimeric antigen receptors: CD28 outperforms combined CD28-OX40 "super-stimulation". *Molecular therapy: the journal of the American Society of Gene Therapy* 2013: 21(12): 2268-77.

32. Mor F, Cohen I R. IL-2 rescues antigen-specific T cells from radiation or dexamethasone-induced apoptosis. Correlation with induction of Bcl-2. *J Immunol* 1996; 156(2): 515-22.

33. Isakov N, Altman A. PKC-theta-mediated signal delivery from the TCR/CD28 surface receptors. *Frontiers in immunology* 2012; 3: 273.

34. Loskog A, Giandomenico V, Rossig C, Pule M, Dotti Brenner M K. Addition of the CD28 signaling domain to chimeric T-cell receptors enhances chimeric T-cell resistance to T regulatory cells. *Leukemia* 2006; 20(10): 1819-28.

35. Schwarzer A, Wolf B, Fisher J L, Schwaab T, Olek S, Baron U et al. Regulatory T-cells and associated pathsways in metastatic renal cell carcinoma (mRCC) patients undergoing DC-vaccination and cytokine-therapy. *PloS one* 2012; 7(10): e46600.

36. Lamers C H, Willemsen R, Elzakker P, van Steenbergen-Langeveld S, Broertjes M, Oosterwijk-Wakka J el al.

Immune responses to transgene and retroviral vector in patients treated with ex vivo-engineered T cells. *Blood* 2011; 117(1): 72-82.

37. Miotti S, Negri D R, Valota O, Calabrese M, Bolhuis R L, Gratama J W et al. Level of anti-mouse-antibody response induced by bi-specific monoclonal antibody OC/TR in ovarian-carcinoma patients is associated with longer survival. *International journal of cancer. Journal international du cancer* 1999; 84(1): 62-8.

38. Kershaw M H, Westwood J A, Parker L L, Wang G, Eshhar Z, Mavroukakis S A et al. A phase I study on adoptive immunotherapy using gene-modified T cells for ovarian cancer. *Clin Cancer Res* 2006; 12(20 Pt 1): 6106-15.

39. Pastorekova S. Carbonic anhydrase IX (CAIX) as a potential target for cancer therapy. *Cancer Therapy* 2004, 2: 245-262.

40. Pastorekova S, Parkkila S, Parkkila A K, Opavsky R, Zelnik V. Saarnio J et al. Carbonic anhydrase IX, MN/CA IX: analysis of stomach complementary DNA sequence and expression in human and rat alimentary tracts. *Gastroenterology* 1997; 112(2): 398-408.

41. Saarnio J, Parkkila S, Parkkila A K, Waheed A, Casey M C, Zhou X Y et al, Immunohistochemistry of carbonic anhydrase isozyme IX (MN/CA IX) in human gut reveals polarized expression in the epithelial cells with the highest proliferative capacity. *The journal of histochemistry and cytochemistry: official journal of the Histochemistry Socity* 1998; 46(4): 497-504.

42. Zavada J, Zavadova Z, Zat'ovicova M, Hyrsl L, Kawaciuk I. Soluble form of carbonic anhydrase IX (CA IX) in the serum and urine of renal carcinoma patients. *Br J Cancer* 2003; 89(6): 1007-71.

43. Hombach A, Koch D, Sircar R, Heuser C, Diehl V, Kruis W et al. A chimeric receptor that selectively targets membrane-bound carcinoembryonic antigen (mCEA) in the presence of soluble CEA, *Gene Ther* 1999; 6(2): 300-4.

44. Carpenito C, Milone M C, Hassan R, Simonet J C, Lakhal M, Suhoski M M et al. Control of large, established tumor xenografts with genetically retargeted human T cells containing CD28 and CD137 domains. *Proceedings of the National Academy of Sciences of the United States of America* 2009; 106(9): 3360-5.

45. Gill S, Tasian S K, Ruella M, Shestova O, Li Y, Porter D L et al. Efficacy against human acute myeloid leukemia and myeloablation of normal hematopoiesis in a mouse model using chimeric antigen receptor-modified T cells, *Blood* 2014.

46. Hombach A A, Heiders J, Foppe M, Chmielewski M, Abken H. OX40 costimulation by a chimeric antigen receptor abrogates CD28 and IL-2 induced IL-10 secretion by redirected CD4(+) T cells. *Oncoimmunology* 2012; 1(4): 458-466.

47. Song D G, Ye Q, Carpenito C, Poussin M, Wang L P, Ji C et al. In vivo persistence, tumor localization, and antitumor activity of CAR-engineered T cells is enhanced by costimulatory signaling through CD137 (4-1BB). *Cancer research* 2011; 71(13): 4617-27.

48. Bedke J, Stenzl A. Immunotherapeutic strategies for the treatment of renal cell carcinoma: where are we now? *Expert review of anticancer therapy* 2013; 13(12): 1399-408.

49. Bailey A, McDermott D F. Immune checkpoint inhibitors as novel targets for renal cell carcinoma therapeutics. *Cancer J* 2013; 19(4): 348-52.

50. Maher J, Brentjens R J, Gunset G, Riviere I, Sadelain M. Human T-lymphocyte cytotoxicity and proliferation directed by a single chimeric TCRzeta /CD28 receptor. *Nat Biotechnol* 2002, 20(I): 70-5.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A method of treating a G250-expressing tumor in a subject comprising administering to said subject a genetically engineered cell which expresses and bears on the cell surface membrane a chimeric antigen receptor (CAR) comprising an intracellular signaling domain, a transmembrane domain and an extracellular domain, wherein the extracellular domain comprises a carbonic anhydrase IX (G250)-specific antibody or fragment thereof, wherein the transmembrane domain comprises CD28, wherein the intracellular signaling domain comprises a CD3 zeta chain, and wherein the genetically engineered cell is a T-cell or an NK cell.

2. The method of claim 1, wherein the genetically engineered cells are derived from cells that are autologous to the subject.

3. The method of claim 1, wherein the tumor is a renal cancer, ovarian cancer, breast cancer, esophageal cancer, bladder cancer, colon cancer, or non-small cell lung cancer.

4. The method of claim 3, wherein the renal cancer is renal clear cell cancer.

5. The method of claim 1, further comprising administering IL-2.

6. The method of claim 1, further comprising administering an anti-PD-1, an anti-PDL-1 or an anti-CTL4 antibody.

7. The method of claim 1, wherein the transmembrane domain further comprises a stalk region positioned between the extracellular domain and the transmembrane domain.

8. The method of claim 1, further comprising one or more costimulatory molecules positioned between the transmembrane domain and the intracellular signaling domain.

9. The method of claim 8, wherein the costimulatory molecule is CD28, 4-1BB, ICOS, or OX40.

10. The method of claim 1, wherein the antibody is a Fab or scFV.

11. The method of claim 1, wherein the antibody has heavy chain comprising
a CDR1 comprising an amino acid sequence SYAMS (SEQ ID NO: 55);
a CDR2 comprising an amino acid sequence AISANGGT-TYYADSVKG (SEQ ID NO: 67); and
a CDR3 comprising an amino acid sequence NGNYR-GAFDI (SEQ ID NO: 65); and
a light chain with a CDR1 comprising an amino acid sequence TGSSSNIGAGFDVH (SEQ ID NO: 68), an amino acid sequence TGSSSNIGAGYDVH (SEQ ID NO: 61), or an amino acid sequence TGTSSNI-GAGYDVH (SEQ ID NO: 81); a CDR2 comprising an amino acid sequence GNTNRPS (SEQ ID NO: 69), an amino acid sequence GNSNRPS (SEQ ID NO: 72), or an amino acid sequence GNNNRPS (SEQ ID NO: 62); and
a CDR3 comprising an amino acid sequence QSYDSRL-SAWV (SEQ ID NO: 70), an amino acid sequence QSYDRSLSWV (SEQ ID NO: 73), an amino acid sequence QSYDSTLRVWM (SEQ ID NO: 74), an amino acid sequence QSYDKSLTWV (SEQ ID NO: 76), an acid amino sequence QSYDKSLSWV (SEQ ID NO: 80), or an amino sequence QSYDSSLSAWV (SEQ ID NO: 82).

12. The method of claim 1, wherein the antibody has a heavy chain comprising an amino acid sequence selected from the group consisting of the amino acid sequences of SEQ ID NOs 1, 3-23, and wherein the antibody has a light chain comprising an amino acid sequence selected from the group consisting of the amino acid sequences of SEQ ID NOs: 2 and 24-44.

13. The method of claim 1, wherein the T cell is CD4$^+$ or CD8$^+$.

14. The method of claim 13, which comprises a mixed population of CD4$^+$ and CD8$^+$ cells.

* * * * *